US009023816B2

(12) United States Patent
Sloth Weidner et al.

(10) Patent No.: US 9,023,816 B2
(45) Date of Patent: May 5, 2015

(54) BIOACTIVE ALKALOID COMPOSITIONS AND THEIR MEDICAL USES

(71) Applicant: Asiros A/S, Skovlunde (DK)

(72) Inventors: Morten Sloth Weidner, Virum (DK); Ida Sloth Weidner, Virum (DK)

(73) Assignee: Asiros A/S, Skovlunde (DK)

( * ) Notice: Subject to any disclaimer, the term of this patent is extended or adjusted under 35 U.S.C. 154(b) by 0 days.

(21) Appl. No.: 14/330,174

(22) Filed: Jul. 14, 2014

(65) Prior Publication Data

US 2015/0018292 A1    Jan. 15, 2015

(30) Foreign Application Priority Data

Jul. 14, 2013 (DK) .................................. 2013 00427

(51) Int. Cl.

| | | |
|---|---|---|
| A61K 31/7032 | (2006.01) | |
| A61K 36/185 | (2006.01) | |
| C07H 19/04 | (2006.01) | |
| C07H 15/18 | (2006.01) | |
| A23L 1/30 | (2006.01) | |
| A61K 31/185 | (2006.01) | |
| C07H 7/04 | (2006.01) | |
| C07H 19/044 | (2006.01) | |
| C07H 15/10 | (2006.01) | |

(52) U.S. Cl.
CPC ............... *C07H 19/04* (2013.01); *C07H 15/18* (2013.01); *A23L 1/3002* (2013.01); *A23V 2002/00* (2013.01); *A61K 31/185* (2013.01); *A61K 31/7032* (2013.01); *A61K 36/185* (2013.01); *C07H 7/04* (2013.01); *C07H 19/044* (2013.01); *C07H 15/10* (2013.01)

(58) Field of Classification Search
CPC ...... C07H 15/10; C07H 15/18; C07H 19/044; A61K 31/7032; A61K 31/7056
See application file for complete search history.

(56) References Cited

U.S. PATENT DOCUMENTS

| | | | |
|---|---|---|---|
| 5,011,855 A | 4/1991 | Traitler et al. | |
| 2002/0018821 A1 | 2/2002 | Soulier et al. | |

FOREIGN PATENT DOCUMENTS

| | | | | |
|---|---|---|---|---|
| EP | 0531155 A1 | 3/1993 | | |
| JP | 2002-212059 | * | 7/2002 | ............... A61K 7/50 |
| WO | 2007143631 A2 | 12/2007 | | |
| WO | 2010037213 A1 | 4/2010 | | |
| WO | 2010051814 A1 | 5/2010 | | |
| WO | 2013035072 A1 | 3/2013 | | |
| WO | WO2013/037859 | * | 3/2013 | ............... A61K 36/28 |

OTHER PUBLICATIONS

Lyall et al., "Short-term blackcurrant extract consumption modulates exercise-induced oxidative stress and lipopolysaccharide-stimulated inflammatory responses" Am J Physiol Regul Integr Comp Physiol (2009) vol. 297 pp. R70-R81.*
English language abstract and machine translation for JP2002-212059 (published Jul. 2002), machine translation from http://worldwide.espacenet.com/.*
Godevac et al., Chemical Composition of Currant Seed Extracts and Their Protective Effect on Human Lymphocytes DNA (2012) voo. 77 No. 7 pp. C779-C783.*
Bagger-Jorgensen et al., "Effects of different enzymatic pre-press maceration treatments on the release of phenols into blackcurrant juice" Eur Food Res Technol (2004) vol. 219 pp. 620-629.*
Botusan et al. "Stabilization of HIF-1α is critical to improve wound healing in diabetic mice," PNAS, 2008, pp. 19426-19431, vol. 105(49).
Montesinos et al. "Wound Healing is Accelerated by Agonists of Adenosine A2 (Gαs-linked) Receptors," Journal of Experimental Medicine, 1997, pp. 1615-1620, vol. 186(9), The Rockefeller University Press.
Daggy et al. "Additive hypocholesterolemic effect of psyllium and cholestyramine in the hamster: influence on fecal sterol and bile acid profiles," Journal of Lipid Research, 1997, pp. 491-502, vol. 38.
Bensch et al. "Effects of LY295427, a Low-Density Lipoprotein (LDL) Receptor Up-Regulator, on LDL Receptor Gene Transcription and Cholesterol Metabolism in Normal and Hypercholesterolemic Hamsters," Journal of Pharmacology and Experimental Therapeutics, 1999, pp. 85-92, vol. 289(1).
Johnson et al. "Antioxidant With Marked Lipid- and Glucose-Lowering Activity in Diabetic Rats and Mice," Diabetes, 1993, pp. 1179-1186, vol. 42.
Van Heek et al. "Ezetimibe, a Potent Cholesterol Absorption Inhibitor, Normalizes Combined Dyslipidemia in Obese Hyperinsulinemic Hamsters," Diabetes, 2001, pp. 1330-1335, vol. 50.

(Continued)

*Primary Examiner* — Eric Olson
(74) *Attorney, Agent, or Firm* — McLane, Graf, Raulerson & Middleton, PA

(57) ABSTRACT

The present invention relates to a novel alkaloid and novel bioactive alkaloid fractions derivable from *Ribes* preferably selected among *Ribes Rubrum* and *Ribes nigrum*; methods of manufacturing such bioactive *Ribes* alkaloid fractions and their use for the inhibition of IKK-β, PDE4 and/or PDE5 and in addition their promoting effect on mitochondrial biogenesis and function; their therapeutic or non-therapeutic applications as nutritive or medicinal products in the management of conditions associated with impaired mitochondrial function or IKK-β, PDE4 and/or PDE5 activity, such as inflammation, neurodegeneration, dyslipidemia, type 2 diabetes mellitus, impaired wound healing, sarcopenia and other conditions associated with muscle dysfunction or tiredness and fatigue, or where optimization of muscular or cognitive function is desired; extracts, juices or concentrates of *Ribes* comprising such alkaloids; compstions comprising such alkaloids, including pharmaceutical compositions, nutritive product such as functional foods and nutraceutical compositions, and cosmetic compositions and medical devices.

17 Claims, 3 Drawing Sheets

(56) References Cited

OTHER PUBLICATIONS

Aoki et al. "Cholesterol-lowering Effect of NK-104, a 3-Hydroxy-3-methylglutaryl-coenzyme A Reductase Inhibitor, in Guinea Pig Model of Hyperlipidemia," Arzneim.-Forsch./Drug Research, 2001, pp. 197-203, vol. 51.

Maurice et al. "Cyclic nucleotide phosphodiesterase-mediated integration of cGMP and cAMP signaling in cells of the cardiovascular system," Frontiers in Bioscience, 2005, pp. 1221-1228, vol. 10.

Goldhoff et al. "Targeted Inhibition of Cyclic AMP Phosphodiesterase-4 Promotes Brain Tumor Regression," Clinical Cancer Research, 2008, pp. 7717-7725, vol. 14(23).

Chijiwa et al. "Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells," Journal of Biological Chemistry, 1990, pp. 5267-5272, vol. 265(9).

Davies et al. "Specificity and mechanism of action of some commonly used protein kinase inhibitors," Biochemical Journal, 2000, pp. 95-105, vol. 351.

Zhang et al. "A Simple Statistical Parameter for Use in Evaluation and Validation of High Throughput Screening Assays," Journal of Biomolecular Screening, 1999, pp. 67-73, vol. 4(2).

Kleman-Leyer et al. "From Need to Screen Flexible methodology addresses the kinase and phosphatase assay development bottleneck," Drug Discovery & Development, 2003, pp. 81-82, vol. 6(3).

Rodems et al. "A FRET-Based Assay Platform for Ultra-High Density Drug Screening of Protein Kinases and Phosphatases," ASSAY and Drug Development Technologies, 2002, pp. 9-19, vol. 1(1).

Lu et al. "Nigrumin-5-p-coumarate and nigrum-5-ferulate, two unusual nitrile-containing metabolites from black currant (*Ribes nigrum*) seed," Phytochemistry, Feb. 2002, pp. 465-468, vol. 59(4), Elsevier B. V.

Schwarz et al. "Sensory-Guided Decomposition of Red Currant Juice (*Ribes rubrum*) and Structure Determination of Key Astringent Compounds," Journal of Agricultural and Food Chemistry, Feb. 2007, pp. 1394-1404, vol. 55(4), Elsevier B. V.

Schwarz et al. "Isolation, Structure Determination, and Sensory Activity of Mouth-Drying and Astringent Nitrogen-Containing Phytochemicals Isolated from Red Currants (*Ribes rubrum*)," Journal of Agricultural and Food Chemistry, Feb. 2007, pp. 1405-1410, vol. 55(4), Elsevier B. V.

Yoshikawa et al. "Rhodiocyanosides A and B, new antiallergic cyanoglycosides from Chinese natural medicine 'Si Lie Hong Jing Tian', the underground part of *Rhodiola* Quadrifida (Pall.) Fisch. et Mey.," Chemical and Pharmaceutical Bulletin, 1995, pp. 1245-1247, vol. 43(7).

Sójka et al. "Composition and properties of purified phenolics preparations obtained from an extract of industrial blackcurrant et al. (*Ribes nigrum* L. ) pomace," Journal of Horticultural Science & Biotechnology, 2009, pp. 100-106, ISAFRUIT special issue.

Godevac et al. "Chemical Composition of Currant Seed Extracts and Their Protective Effect on Human Lymphocytes DNA," Journal of Food Science, 2012, pp. C779-C783, vol. 77(7).

Kähkönen et al. "Berry Phenolics and Their Antioxidant Activity," Journal of Agricultural and Food Chemistry, 2001, pp. 4076-4082, vol. 49(8).

Wang et al. "Constituents from *Chimonanthus praecox* (wintersweet)," Phytochemistry Letters, 2011, pp. 271-274, vol. 4(3).

Fitzmaurice et al. "Antioxidant Therapies for Wound Healing: A Clinical Guide to Currently Commercially Available Products," Skin Pharmacology and Physiology, 2011, pp. 113-126, vol. 24(3).

Bhatnagar et al. "Hypercholesterolaemia and Its Management," British Medical Journal, 2008, pp. 503-508, vol. 337 (7668).

Bäumer et al. "Highly selective phosphodiesterase 4 inhibitors for the treatment of allergic skin diseases and psoriasis," Inflammation and Allergy—Drug Targets, 2007, pp. 17-26, vol. 6(1).

Sinno et al., "Complements and the Wound Healing Cascade: An Updated Review," Plastic Surgery International, 2013, pp. 1-7.

Ikari et al. "Phosphodiesterase-4 Inhibition Augments Human Lung Fibroblast Vascular Endothelial Growth Factor Production Induced by Prostaglandin E2," American Journal of Respiratory Cell and Molecular Biology, 2013, pp. 571-581, vol. 49(4).

Nakamura et al. "Enhanced wound healing by topical administration of mesenchymal stem cells transfected with stromal cell-derived factor-1," Biomaterials, 2013, pp. 9393-9400, vol. 34.

Bitto et al. "Relaxin improves multiple markers of wound healing and ameliorates the disturbed healing pattern of genetically diabetic mice," Clinical Science, 2013, pp. 575-585, vol. 125.

Bermudez et al. "Inhibition of stromal cell-derived factor-1α further impairs diabetic wound healing," Journal of Vascular Surgery, 2011, pp. 774-784, vol. 53(3).

Asai et al. "Dibutyryl cAMP influences endothelial progenitor cell recruitment during wound neovascularization," Journal of Investigative Dermatology, 2006, pp. 1159-1167, vol. 126.

Ishii et al. "Antipruritic effect of the topical phosphodiesterase 4 inhibitor E6005 ameliorates skin lesions in a mouse atopic dermatitis model," Journal of Pharmacology and Experimental Therapeutics, 2013, pp. 105-112, vol. 346.

Rundfeldt et al. The stable cyclic adenosine monophosphate analogue, dibutyryl cyclo-adenosine monophosphate (bucladesine), is active in a model of acute skin inflammation, Archives of Dermatological Research, 2012, pp. 313-317, vol. 304.

Farsaei et al. "An Old Drug for a New Application: Potential Benefits of Sildenafil in Wound Healing," Journal of Pharmacy & Pharmaceutical Sciences, 2012, pp. 483-498, vol. 15(4).

Witte et al. L-Arginine supplementation enhances diabetic wound healing: involvement of the nitric oxide synthase and arginase pathways, Metabolism, 2002, pp. 1269-1273, vol. 51(10).

Foresta et al. "Phosphodiesterase-5 inhibitor tadalafil acts on endothelial progenitor cells by CXCR4 signalling," Current Drug Delivery, 2010, pp. 274-282, vol. 7(4).

Foresta et al. "PDE-5 inhibitor, Vardenafil, increases circulating progenitor cells in humans," International Journal of Impotence Research, 2005, pp. 377-380, vol. 17.

Foresta et al. "Effect of vardenafil on endothelial progenitor cells in hypogonadotrophic hypogonadal patients: role of testosterone treatment," Clinical Endocrinology, 2009, pp. 412-416, vol. 71.

Kim et al. "High glucose condition induces autophagy in endothelial progenitor cells contributing to angiogenic impairment," Biological & Pharmaceutical Bulletin, 2014, pp. 1248-1252, vol. 37(7).

Schett et al. "Apremilast: a novel PDE4 inhibitor in the treatment of autoimmune and inflammatory diseases," Therapeutic Advances in Musculoskeletal Disease, 2010, pp. 271-278, vol. 2(5).

Towler et al. "AMP-activated protein kinase in metabolic control and insulin signaling," Circulation Research, 2007, pp. 328-341, vol. 100.

Van Diepen et al. "Hepatocyte-specific IKK-β activation enhances VLDL-triglyceride production in APOE*3-Leiden mice," Journal of Lipid Research, 2011, pp. 942-950, vol. 52.

Yuan et al. "Reversal of Obesity- and Diet-Induced Insulin Resistance with Salicylates or Targeted Disruption of IKKβ," Science, 2001, pp. 1673-1677, vol. 293(5535).

Nisoli et al. "Mitochondrial biogenesis in mammals: the role of endogenous nitric oxide," Science, 2003, pp. 896-899, vol. 299(5608).

Sheffield-Moore et al. "Sildenafil Increases Muscle Protein Synthesis and Reduces Muscle Fatigue," Clin. Trans. Sci., 2013, pp. 463-468, vol. 6(6).

* cited by examiner

BIOACTIVE ALKALOID COMPOSITIONS AND THEIR MEDICAL USES

CROSS-REFERENCE TO RELATED APPLICATIONS

This application claims the benefit under 35 U.S.C. §119 (a) of Danish Application No. PA 2013 00427, filed Jul. 14, 2013, entitled Novel Bioactive Alkaloids and Alkaloid Fractions Derivable From *Ribes* Species, the disclosure of which is incorporated by reference herein in its entirety.

BACKGROUND OF THE INVENTION

The present invention relates to a novel alkaloid and novel bioactive alkaloid fractions derivable from *Ribes* preferably selected among *Ribes Rubrum* and *Ribes nigrum*; methods of manufacturing such bioactive *Ribes* alkaloid fractions and their use for the inhibition of IKK-β, PDE4 and/or PDE5 and in addition to their promoting effect on mitochondrial biogenesis and function; their therapeutic or non-therapeutic applications as nutritive or medicinal products in the management of conditions associated with impaired mitochondrial function or IKK-β, PDE4 and/or PDE5 activity, such as inflammation, neurodegeneration, dyslipidemia, type 2 diabetes mellitus, impaired wound healing, sarcopenia and other conditions associated with muscle dysfunction or tiredness and fatigue, or where optimization of muscular or cognitive function is desired; extracts, juices or concentrates of *Ribes* comprising such alkaloids; compostions comprising such alkaloids, including pharmaceutical compositions, nutritive products such as functional foods and nutraceutical compositions, cosmetic compositions and medical devices.

The global community is facing a serious challenge with the growing burden of lifestyle-related diseases like type 2 diabetes mellitus (DM2) and atherosclerotic cardiovascular disease (CVD). Binding together DM2 and CVD is the metabolic syndrome. Metabolic syndrome is characterized by a cluster of risk factors including atherogenic dyslipidemia, abdominal obesity, raised blood pressure, insulin resistance±glucose intolerance, a proinflammatory state and a prothrombotic state [Scott 2004, Circulation; 109:433-438]. The American Heart Association defines the metabolic syndrome as the combination of dyslipidemia, abdominal obesity, hypertension, and insulin resistance, a constellation of disorders that bestow a cardiovascular risk far greater than any of its individual components [Grundy 2004, Circulation; 109:433-438]. CVDs are the number one cause of death globally: more people die annually from CVDs than from any other cause. An estimated 17.3 million people died from CVDs in 2008, representing 30% of all global deaths. Of these deaths, an estimated 7.3 million were due to coronary heart disease and 6.2 million were due to stroke. By 2030, almost 23.6 million people will die from CVDs, mainly from heart disease and stroke. These are projected to remain the single leading causes of death [WHO Fact sheet No 317, September 2011]. CVD is associated with dyslipidemia leading to arterial plaque formation forming the basis for coronary heart disease and stroke. Of the 346 million people worldwide with diabetes, 90% have DM2. In 2004, an estimated 3.4 million people died from consequences of high blood sugar. WHO projects that diabetes deaths will double between 2005 and 2030 [WHO Fact sheet No 312, August 2011]. DM2 is characterized by insulin resistance and increased blood sugar levels and is highly associated with CVD [Moller 2001, Nature; 414, 821-27]. More and more attention is now being paid to combined atherogenic dyslipidemia which is typically presented in patients with DM2 and metabolic syndrome.

A fundamental treatment of CVD as well as DM2 is the reduction of the blood cholesterol, especially the LDL. Treatments for dyslipidemia includes statins, fibrates, inhibition of cholesterol absortion, inhibition of liver cholesterol synthesis, increased excretion of cholesterol and inhibition of free fatty acid release [Bhatnagar 2008, BMJ; 337:503-8]. Such existing treatments are associated with a number of adverse effects including muscle pain and damage which may be life threatening (rhambodmyolysis), as well as associated with liver damage and gastrointestinal side effects. Consequently, there is a strong need for effective therapeutic principles suitable for application in the broader population.

The wound healing process is complex and dynamic, restoring cellular structures and tissue layers. Acute wounds are either traumatic or surgical and move through the healing process at a predictable rate from insult to closure. Non-healing, or chronic wounds, are complex wounds that do not progress through the usual phases of healing. In non-healing wounds, changes occur within the molecular environment of a chronic wound that are not conducive to healing, such as high levels of inflammatory cytokines, and low levels of growth factors. These changes terminate the healing process and increase the potential for bacterial infections. Addressing the issues that might be responsible for the physiological wound changes may restart healing and diminish the risk of further complications, and a faster wound healing diminshes the time of exposure to bacteria and subsequent infections.

Treatment of various types of wounds represents a huge burden on health care systems and patients worldwide and an immense therapeutic challenge due to lack of effective treatment of chronic wounds.

71.5 million surgical procedures were performed in the United States alone in 2000. Unhealed acute wounds are open to infectious agents and infection occurs in approximately 10% of surgical wounds making a faster wound healing generally advantageous. Furthermore, many surgical patients are obese or have chronic diseases that cause an impaired wound healing, creating a great need for improved wound healing. An additional burden of acute wound healing is the challenge of scarring that may have long lasting functional, cosmetic as well as psychological consequences for the patient. A scar represents the sum of the injury, the reparative process and subsequent interventions to improve the scarring process. Both normal and hypertrophic scars remain difficult to treat and impossible to prevent and there is a great need for therapeutic principles that advance wound healing without problematic scarring.

Chronic non-healing wounds represent a silent epidemic that affects a large fraction of the world population and poses a major threat to the public health. In the United States alone, chronic wounds affect 6.5 million patients. In the Scandinavian countries, the associated costs account for 2-4% of the total health care expenses. The major chronic wound types are diabetic ulcers, pressure ulcers and venous ulcers.

It is estimated that there are over 7.4 million pressure ulcers in the world where estimation was possible i.e. excluding the vast number of developing countries. During the first two weeks of admission, hospital acquired pressure ulcers occur in approximately 9% of hospitalized patients and nearly 60,000 deaths occur annually in the United States from hospital-acquired pressure ulcers. Pressure ulcers can be a major source of infection and lead to complications such as septicemia, osteomyelitis and, even death. The healing of pressure ulcers take a long time and are costly and time-consuming to treat.

It is estimated that up to 25% of all diabetics will develop a diabetic foot ulcer and it is estimated that 12% of individuals with a foot ulcer will require amputation. About 71,000 non-traumatic lower-limb amputations were performed in the United States in people with diabetes in 2004. Treatment of diabetic foot ulcers is often a specialist task and represents a huge unsolved challenge in modern wound care.

Venous ulcers account for 70%-90% of ulcers found on the lower leg. Venous leg ulcerations present a common and recurring problem in older people creating discomfort and distress for the patient and a great cost to the health care services. In individuals 65 years and older, venous leg ulcers affect approximately 1.69% of the population. Up to one-third of treated patients experience four or more episodes of recurrence. The mainstay of treatment includes local wound care and continuous compression therapy by bandaging by trained personnel or by graduated compression stockings. However, compression therapy is contraindicated in those with occlusive arterial disease, it requires a trained staff to apply the compression bandages and patient compliance with compression stockings is often poor.

Many topical agents are available that are meant to improve the wound healing environment. Wound debridement removes devitalized tissue and accumulated debris and includes irrigation, excisional debridement, enzymatic debridement and biological debridement with maggot therapy. Topical therapy includes hyperbaric oxygen therapy, negative pressure wound therapy, application of growth factors such as platelet-derived growth factor, epidermal growth factor and granulocyte-macrophage colony stimulating factor, topical preparations with antiseptics and antimicrobials, including iodine, chlorhexidine, silver and antibiotics. Various wound dressings are used to manage the moisture level in and around the wound, including gauze bandages, fine mesh gauze impregnated with petroleum, paraffin wax, or other ointments, films, foams, alginates, hydrocolloids, hydrogels and hydroactive dressings. Due to the very nature of topical treatments, these address only the superficial aspects of wound healing and have proved insufficient for effective treatment. No effective oral therapy that improves wound healing is available. Therefore, there is a huge need for effective oral treatment that promotes wound healing from within.

To promote wound healing from within, various aspects of the wound healing process may be addressed. Healing is traditionally explained in terms of 4 overlapping phases: hemostasis, inflammation, proliferation, and maturation. During hemostasis, platelets play a crucial role in clot formation and the initial inflammatory aspect of tissue healing by secreting inflammatory cytokines and chemokines which subsequently attract leukocytes and macrophages to the site of injury. These cells débride injured tissue and secrete proteases, cytokines and growth factors that propagate various aspects of healing. During the proliferative phase, epithelialization, fibroplasia, and angiogenesis occur, forming granulation tissue, which includes inflammatory cells, fibroblasts, and neovasculature in a matrix of fibronectin, collagen, glycosaminoglycans, and proteoglycans. Finally, during the maturation phase, collagen forms tight cross-links to other collagen and with protein molecules, increasing the tensile strength of the scar. The entire wound healing process is highly complex and the cellular events that lead from open wound to scar formation overlap. A rich blood supply is vital to sustain newly formed tissue and angiogenesis is a key aspect of wound healing. It involves the release of numerous angiogenic molecules among which vascular endothelial growth factor (VEGF) secreted by macrophages and epidermal cells is critical for angiogenesis.

In relation to wound healing, phosphodiesterase 4 (PDE4) inhibition is a highly promising therapeutic strategy. cAMP is a second messenger involved in the cytokine production of inflammatory cells, in angiogenesis, and in the functional properties keratinocytes which are all relevant in the process of wound healing. The intracellular levels of cAMP are determined by the activities of adenylate cyclase which synthesize cAMP from ATP and PDE4, which hydrolyzes cAMP to AMP. PDE4 is expressed in a variety of cells including inflammatory cells, smooth muscle cells, fibroblasts, endothelial cells and keratinocytes [Bäumer 2007, Inflamm Allergy Drug Targets, March; 6(1):17-26] which are all present in the skin.

The effects of cAMP are transduced by two ubiquitously expressed intracellular cAMP receptors, protein kinase A (PKA) and exchange protein directly activated by cAMP (EPAC) [Whittmann 2013, P. Dermatol Ther, April 27; 3(1): 1-15]. The cAMP/PKA signaling pathway has been demonstrated to promote endothelial cell sprouting and tube formation [Aslam 2013, Acta Physiologica; 207(694):O10] and cAMP acts as a second messenger in the release of VEGF, mediated by prostaglandin E2 (PGE2) through the cAMP/PKA signaling pathway [Ikari 2013, Am J Respir Cell Mol Biol, October; 49(4):571-81]. Activation of Epac through the cAMP/Epac signaling pathway has been demonstrated to attenuate thrombin-induced hyperpermeability in endothelial cells [Aslam 2013, Acta Physiologica 2013; 207(694):O10]. Endothelial progenitor cells (EPC) are centrally involved in angiogenesis in regenerating vasculature and the recruitment of these cells is in part mediated by a hypoxic gradient in the wound stimulating epidermal cells to enhanced expression of pro-angiogenic factors like stromal cell-derived factor-1α (SDF-1α) and VEGF [Ceradini 2004, Nat Med, August; 10(8):858-64], [Tepper 2005, Blood, February 1; 105(3):1068-77] which, subsequently, mobilize EPC from the bone marrow to the ischemic sites. Under hypoxic conditions such as in wounds, EPC are stimulated to form organized cell clusters, which then form cord-like vascular structures that undergo canalization and connect to existing vessels.

In chronic wounds, the process of angiogenesis is impaired, resulting in defective granulation tissue formation, which eventually causes failure of the wound healing to progress through the proliferation phase. For example, diabetic wounds are characterized by impaired wound healing associated with of decreased angiogenesis and VEGF expression in the wound [Bitto 2013, Clin Sci, December; 125(12): 575-85], [Gu 2013, Diabetes Res Clin Pract; October; 102(1): 53-9], [Asai 2006, J Invest Dermatol, May; 126(5): 1159-67] and it has been demonstrated that topical VEGF induces a significantly accelerated repair in experimental wounds in diabetic mice, and exogenous application of VEGF can increase early angiogenesis and tensile strength in the ischemic wounds in rats [Sinno 2013, Plast Surg Int; 2013:1-7]. Phosphodiesterase-4 inhibition augments human lung fibroblast VEGF production induced by prostaglandin E2 [Ikari 2013, Am J Respir Cell Mol Biol, October; 49(4):571-81] and topical administration of Sodium N-6,20-O-dibutyryl adenosine-30,50-cyclic phosphate (DBcAMP), a stabilized analog of cAMP in diabetic wounds enhances wound healing significantly [Asai 2006, J Invest Dermatol, May; 126(5): 1159-67]. It is therefore highly likely that inhibition of PDE4 may increase local VEGF-secretion and promote wound healing, in particular impaired wound healing.

Another important factor in the granulation phase is stromal cell-derived factor (SDF)-1α. SDF-1α plays a critical and multifaceted role in the wound-healing process in both normal and diabetic environments. It is a chemotactic factor regulating the migration of EPCs and angiogenesis. Hence upregulation of SDF-1α enhances wound healing [Nakamura 2013, Biomaterials, December; 34(37):9393-400] and decreased levels of SDF-1α impair healing by decreasing cellular migration and angiogenesis. Diabetic wounds are deficient in SDF-1α and increasing the level of SDF-1α increases diabetic wound healing [Bitto 2013, Clin Sci, December; 125(12):575-85], [Bermudez 2011, J Vasc Surg; 53:774-84]. Elevation of cAMP by local administration of DBcAMP in diabetic wounds has been demonstrated to increase the transcription and production of SDF-1α by macrophages and mesenchymal cells and significantly accelerate the wound healing [Asai 2006, J Invest Dermatol, May; 126 (5):1159-67].

The proliferation of epidermal basal cells is another key aspect of wound healing. cAMP has long been regarded as a second messenger and a regulator of human keratinocyte proliferation. cAMP signaling regulates keratinocyte proliferation by modulating mitogen-activated protein kinase (MAPK) activity. DBcAMP has been demonstrated to promote the production of transforming growth factor-β by keratinocytes and fibroblasts, as well as the proliferation and migration of keratinocytes [Zhou 2000, Br J Dermatol, September; 143(3):506-12], [Onuma 2001, Arch Dermatol Res, March; 293(3):133-8], [Iwasaki 1994, J Invest Dermatol, June; 102(6):891-7] and accelerate healing and re-epithelialization of full-thickness wounds [Balakrishnan 2006, Biomaterials, March; 27(8):1355-61]. Similarly, elevation of cAMP by PDE4 inhibition may therefore enhance epithelialization in the process of wound healing.

PDE4 is expressed in cells such as endothelial cells, keratinocytes and fibroblasts [Bäumer 2007, Inflamm Allergy Drug Targets, March; 6(1):17-26] which are all present in the wound bed during wound healing. Topical application of a PDE4-inhibitor has been demonstrated to exert anti-inflammatory effects with reduced expression of cytokines and adhesion molecules [Ishii 2013, J Pharmacol Exp Ther, July; 346(1):105-12]. Topical administration of DBcAMP, another way to increase local cAMP, has been demonstrated to significantly reduce the inflammatory oedema in the arachidonic acid induced ear oedema model in mice [Rundfeldt 2012, Arch Dermatol Res, February 3(304):313-317]. The role of antiinflammatory effects elicited by PDE4 inhibition in supporting the wound healing may be most pronounced in chronic wounds where chronic inflammation is an important facet of the non-healing state of the wound and decreased inflammation is associated with increased wound healing [Eming 2007, J Invest Dermatol, March; 127(3):514-25]. Hence, modulation of pro-inflammatory mediators by PDE4 inhibition may add to the wound healing effects exerted by PDE4 inhibition through propagation of angiogenesis and enhanced epithelialization.

In conclusion, cAMP signaling is involved in the regulation of several functions of importance to wound healing including angiogenesis, inflammation and epithelialization. Elevation of cAMP through inhibition of PDE4 therefore is a highly relevant therapeutic strategy for enhancement of acute and chronic wound healing through modulation of pro-inflammatory mediators, propagation of angiogenesis and enhanced epithelialization.

In relation to enhanced wound healing, phosphodiesterase 5 (PDE5) inhibition is another highly promising therapeutic strategy. PDE5 is a phosphodiesterase capable of degrading cGMP to 5'-GMP thereby inhibiting the activity of cGMP. PDE5 inhibition prevents the degradation of cGMP, thereby enhancing and/or prolonging its effects. cGMP is a second messenger which may be synthesized as a result of nitric oxide (NO) activation of soluble guanylyl cyclase. It is involved in various physiological processes through the activation of protein kinase G (PKG). Conversion of cGMP to 5'-GMP by PDE5 effectively inhibits NO/cGMP signaling whereas PDE5 inhibition restores NO/cGMP signaling. NO is a small radical, formed from the amino acid L-arginine by three distinct isoforms of nitric oxide synthase. The inducible isoform (iNOS) is synthesized in the early phase of wound healing by inflammatory cells, mainly macrophages. However, many cells participate in NO synthesis during the proliferative phase after wounding. Beneficial effects of NO have been repetitiously demonstrated in wound healing, and may act through several mechanisms also including vasodilation, scavenging of oxidative stress components, improvement of angiogenesis and promotion of endothelial cell proliferation [Farsaei 2012, J Pharm Pharmaceut Sci; 15(4):483-498]. NO serves as an important mediator that regulates gene expression and proliferation in keratinocytes, regulation of fibroblast migration and collagen deposition in wounded tissue [Han et al 2012, Am J Pathol, April; 180(4):1465-73], [Frank et al 2002, Kidney International; 61: 882-888]. NO released through iNOS was shown to regulate collagen formation, cell proliferation and wound contraction in animal models of wound healing [Witte 2002, Metabolism, October; 51(10): 1269-73]. Accordingly, protection and enhancement of the NO-cGMP-PKG signaling pathway by inhibition of PDE5-conversion of cGMP is indeed beneficial to wound healing as confirmed by the significantly improved wound-healing with the peroral PDE5 inhibitor Sildenafil in 15 different animal studies and 2 clinical human studies on hard-to-heal-wounds [Farsaei 2012, J Pharm Pharmaceut Sci; 15(4): 483-498]. Furthermore, PDE5 inhibition as a strategy for promoting angiogenesis has been demonstrated in relation to the PDE5 inhibitor Vardenafil, which upregulates protein expression of VEGF and enhance mobilization of EPC in peripheral blood and bone marrow, contributing to neovascularization in a model of unilateral hindlimb ischemia in mice [Sahara 2010, Arterioscler Thromb Vasc Biol, July; 30(7):1315-24]). This finding is supported by the in vitro and in vivo findings that endothelial progenitor cells express PDE5; that the PDE5 inhibitor tadalafil induces a significant increase in EPC number mediated by increased CXCR4 expression, and that prolonged therapy with PDE5 inhibitors in humans increases circulating EPC, supporting the notion of an involvement of cGMP second messenger system in both EPC release from the bone marrow and EPC-mediated peripheral re-endothelization. [Foresta et al 2005, Int J Impot Res, July-August; 17(4):377-80], [Foresta et al 2009, Clin Endocrinol, September; 71(3):412-6], [Foresta et al 2010, Curr Drug Deliv, October; 7(4):274-82]. In conclusion, PDE5 inhibition has been convincingly demonstrated to be a highly relevant therapeutic strategy in relation to enhancement of wound healing.

Another promising therapeutic target in wound healing is the mitochondria. EPCs are dysfunctional under diabetic conditions resulting in impaired peripheral circulation and delayed wound healing. It has been demonstrated that mitochondrial autophagy and mitochondrial impairment is induced in EPCs under high glucose condition, thus linking diabetic cardiovascular complications including impaired wound healing with dysfunctional mitochondria. Optimizing mitochondrial function could therefore also improve diabetic wound healing [Kim 2014, Biol Pharm Bull; 37(7):1248-52].

In relation to inflammatory disorders and conditions, PDE4 and IkappaB kinase β (IKK-β) inhibition are highly promising therapeutic strategies. PDE4 is the predominant cAMP degrading enzyme in a variety of inflammatory cells including eosinophils, neutrophils, macrophages, T cells and monocytes, and may increase the production of pro-inflammatory mediators such as TNF-α, IL-17, IL-22, and IFN-γ, and decrease anti-inflammatory mediators such as IL-10. Inhibition of PDE4 results in an elevation of cAMP in these cells, which in turn down-regulates the inflammatory response. The antiinflammatory effects of PDE4 inhibitors have been well documented both in vitro and in vivo and is mediated partly through PKA but is also associated with Epac, which appears to play a key role in suppressing unwanted inflammation [Parnell 2012, Br J Pharmacol; 166 (2):434-46]. The PDE4 inhibitor Apremilast has profound anti-inflammatory properties in animal models of inflammatory disease, as well as human chronic inflammatory diseases such as psoriasis and psoriatic arthritis. It reduces complex inflammatory processes and interferes with the production of leukotriene B4, inducible nitric oxide synthase, matrix metalloproteinase and blocks the synthesis of several pro-inflammatory cytokines and chemokines, such as tumor necrosis factor alpha, interleukin 23, CXCL9, and CXCL10 in multiple cell types [Schett 2010, Ther Adv Musculoskelet Dis, October; 2(5):271-8], supporting the high relevance of PDE4 inhibition in various chronic inflammatory conditions of the skin, joints, lungs and intestines such as arthritis, psoriasis, chronic obstructive lung disease and inflammatory bowel diseases. Of further relevance to targeting PDE4, PDE4 deficiency suppresses macrophage infiltration in white adipose tissue and reduces adiposity, suggesting that PDE4 inhibitors could have utility in treatment of obesity and for suppression of obesity-induced inflammation in white adipose tissue [Ren 2009, Endocrinology; 150:3076-3082]. Inhibitors of cAMP-specific PDE4 has been shown to increase apolipoprotein A-I (apoA-I)-mediated cholesterol efflux up to 80 and 140% in human THP-1 and mouse J774.A1 macrophages, respectively, concomitant with an elevation of cAMP levels and may provide a novel strategy for the treatment of CVD by mobilizing cholesterol from atherosclerotic lesions [Lin 2002, Biochem Biophys Res Commun, January 18; 290(2):663-9]. PDE4 regulates cAMP pools that affect the activation/phosphorylation state of AMPK and PDE4 inhibition has been shown to activate AMPK [Omar 2009, Cell Signal, May; 21(5):760-6] [Park 2012, Cell, February 3; 148(3):421-33]. AMPK is a pivotal serine/threonine kinase participating in the regulation of glucose, lipid as well as protein metabolism and maintenance of energy homeostasis. Recent studies demonstrated that AMPK can also inhibit NF-κB, suppress the expression of inflammatory genes and attenuate inflammatory injury [Yao 2012, Sheng Li Xue Bao, June 25; 64(3): 341-5]. In the liver, activation of AMPK results in enhanced fatty acid oxidation as well as decreased glucose production. The AMPK system may be partly responsible for the health benefits of exercise and is the target for the antidiabetic drug metformin. It is a key player in the development of new treatments for obesity, DM2, and the metabolic syndrome [Towler 2007, Circ Res, February 16; 100(3):328-41]. Thus, inhibition of PDE4 represents a promising therapeutic strategy in improving inflammatory conditions as well as metabolic conditions.

IKK-β is part of the upstream NF-κB signal transduction cascade of inflammation. IKK-β phosphorylates the inhibitory IκB protein resulting in dissociation of IκB from NF-κB. NF-κB is now free to migrate into the nucleus and activate the transcription of a cascade of proinflammatory cytokines [Häcker 2006, Sci. STKE; 357: 13]. Low-grade inflammation in different tissues is involved in metabolic disorders such as DM2 and CVD. In obesity, free fatty acid overload, endoplasmatic reticulum-overload and excessive glucose levels along with inflammatory macrophage infiltration in visceral fat resulting in chronic inflammation, activates IKK-β, leading to a viscious circle of continuous inflammation, induction of insulin resistance and enhanced VLDL-tricglyceride and lipoprotein production. The outcome on a macrophysiological level is hyperglycemia and hypertriglycerdemia [Meshkani 2009, Clin Biochem; 42 (13-14):1331-46], [Tsai 2009, Am J Physiol Gastrointest Liver Physiol; 296(6):G1287-98], [vDiepen 2011, J Lipid Res; 52:942-950], [Solinas, 2010, J Lipid Res; 24:2596-2611]. IKK-β has been found to serve as a critical molecular link between obesity, metabolic inflammation, and disorders of glucose homeostasis. IKK-β is activated by almost all forms of metabolic stress that have been implicated in insulin resistance or islet dysfunction. Furthermore, IKK-β is critically involved in the promotion of diet-induced obesity, metabolic inflammation, insulin resistance, and beta-cell dysfunction. Hypertriglyceridemia is caused by accumulation of VLDL particles in the plasma as a consequence of changes in lipid metabolism that are associated with obesity. The accumulation of lipids in numerous tissues is accompanied by increased inflammatory processes such as macrophage infiltration and production of inflammatory mediators in white adipose tissue. In liver, fat accumulation increases the activity of the pro-inflammatory NF-κB and liver-specific activation of NF-κB induces metabolic disturbances [Cai 2005, Nat Med; 11:183-90], [Arkan, 2005, Nat Med; 11:191-98]. Proinflammatory cytokines can cause hypertriglyceridemia and, conversely, suppression of inflammation may reduce hypertriglyceridemia [Goldfine 2008, Clin Transl Sci; 1:36-43] suggesting a direct causal role for inflammatory pathways in the development of hypertriglyceridemia. Specific activation of inflammatory pathways exclusively within hepatocytes induces hypertriglyceridemia and the hepatocytic IKK-β pathway has been identified as a possible target to treat hypertriglyceridemia. [Janna 2011, J Lipid Res; 52:942-50]. Furthermore, it has been shown that IKK-β inhibition reverses insulin resistance [Minsheng 2001, Science, August 31; 293(5535):1673-7] and inhibition of the IKK-β pathway enhances degradation of hepatic apoB100, revealing important links between modulation of the inflammatory IKK-β mediated signaling cascade and hepatic synthesis and secretion of apoB100-containing lipoproteins [Tsai 2009, Am J Physiol Gastrointest Liver Physiol, June; 296(6):G1287-98]. Thus, inhibition of IKK-β represents a promising therapeutic strategy in improving inflammatory conditions as well as hypertriglyceridemia and metabolic conditions.

Mitochondria are organelles in eukaryotic cells with their own genome that consume oxygen and substrates to generate ATP necessary for energy demanding processes. In aerobic cells the majority of ATP is produced by oxidative phosphorylation. In the mitochondria, electrons that are donated from the Krebs cycle are passed through the four complexes (complex I-IV) comprising the electron transport chain, eventually reducing oxygen and producing water. The flux of electrons creates an electrochemical potential between the intermembrane space and the matrix of the mitochondria. This potential is utilized by the ATP synthase to phosphorylate ADP producing ATP (oxidative phosphorylation). Mitochondria also participate in a wide range of other cellular processes, including signal transduction, cell cycle regulation, thermogenesis, and apoptosis. They are highly dynamic organelles that are continuously remodeling through fission, fusion, autophagy and biogenesis. Mitochondrial biogenesis is the expansion of existing mitochondrial content, whether through growth of the mitochondrial network (increase in mitochondrial mass) or division of preexisting mitochondria (increases in mitochondrial number). Mitochondrial biogenesis is triggered when the energy demand exceeds respiratory capacity e.g. in response to exercise, stress, hypoxia, nutrient availability, hormones including insulin, reactive oxygen production and temperature.

Spare respiratory capacity is the difference between ATP produced by oxidative phosphorylation at basal and that at maximal activity. Under certain conditions a tissue can require a sudden burst of additional cellular energy in response to stress or increased workload. If the spare respiratory capacity of the cells is not sufficient to provide the required ATP, affected cells risk being driven into senescence or cell death. Exhaustion of the reserve respiratory capacity has been correlated with a variety of pathologies including heart diseases, neurodegenerative disorders and cell death in smooth muscle [Desler 2012, Journal of Aging Research; 2012:p 1-9].

Peroxisome proliferator-activated receptor-γ coactivator 1α (PGC-1α) is widely recognized as a principal regulator of mitochondrial biogenesis and function and therefor represents a highly interesting therapeutic direct or indirect target in relation to modulationg mitochondrial function. PGC-1α coactivates transcription factors that regulate expression of nuclear genes that encode mitochondrial proteins and also of the nuclear gene that encodes mitochondrial transcription factor A (TFAM), which regulates mitochondrial DNA transcription. Thus, PGC-1α regulates the coordinated expression of mitochondrial proteins encoded in both nuclear and mitochondrial genes, activating an array of transcription factors including activation of Nuclear Respiratory Factors 1 and 2 (NRF-1 and NRF-2) which regulate transcription of proteins in the respiratory chain, activation of PPAR-α which regulates enzymes for fatty acid oxidation (β-oxidation), activation of mitochondrial transcription factor A which activates expression of the mitochondrial genome leading to mitochondrial biogenesis, and coactivation of myocyte-enhancing factor 2A (MEF2A) which leads to increased insulin sensitivity by translocation of the glucose transporter to membrane leading to an improved glucose uptake.

Activation of PGC-1 α has been linked to the NO/cGMP signaling pathway which therefore represents a highly relevant strategy for modulating mitochondrial function [Nisoli 2004, Proc Natl Acad Sci, November 23; 101(47):16507-12] through the inhibition of PDE5. Long-term exposure to low concentrations of NO induces mitochondrial biogenesis mediated by cGMP, and involves increased expression of PGC-1α, NRF-1 and mitochondrial transcription factor A. [Nisoli 2003, Science, February 7; 299(5608):896-9.]. NO/cGMP dependent mitochondrial biogenesis furthermore yields functionally active mitochondria, in terms of respiratory function and metabolic activity [Nisoli 2004, Proc Natl Acad Sci, November 23; 101(47):16507-12]. Therefore, inhibition of PDE5, which results in increased levels of cGMP is a very interesting target for stimulation of mitochondrial biogenesis and functionality. This is supported by the finding that cGMP-selective phosphodiesterase inhibitors stimulate mitochondrial biogenesis in kidney tissue [Whitaker 2013, J Pharmacol Exp Ther, December; 347(3): 626-34] and short term PDE5-inhibition with the PDE5 inhibitor Sildenafil has been shown to reduce muscle fatigue and increase skeletal muscle protein synthesis [Sheffield More et al 2013, Clin Transl Sci, December; 6(6):463-8].

Like PDE5 inhibition, inhibition of PDE4, has also been linked to activation of PGC-1α and to stimulation of mitochondrial biogenesis and increased endurance, though through different pathways. Hence, the PDE4 inhibitor Rolipram has been demonstrated to induce mitochondrial biogenesis and increase the expression of PGC-1α, as well as inducing a significantly greater distance on a treadmill before exhaustion in Rolipram treated mice than control mice [Park 2012, Cell, February 3; 148(3):421-33].

It is well established that endurance exercise training induce large increases in mitochondria and even a single bout of exercise induces a rapid increase in mitochondrial biogenesis that is mediated both by activation and by increased expression of PGC-1α [Hollzy 2011, Compr Physiol, April; 1(2):921-40], [Holloszy 2008, J Physiol Pharmacol, December; 59 Suppl 7:5-18][Bartlett 2012, J Appl Physiol, April; 112(7): 1135-43]. PGC-1α signaling controls mitochondrial biogenesis and angiogenesis in response to endurance exercise in skeletal muscle and PGC-1α has been shown to increases exercise performance [Tadaishi et al 2011, PLoS ONE, December, Vol 6, Issue 12:1-13] and to a large degree, the adaptive changes in skeletal muscles such as fiber type transformation, mitochondrial biogenesis, angiogenesis, improved insulin sensitivity and metabolic flexibility induced by endurance training is regulated by PGC-1α [Lira 2010, Am J Physiol Endocrinol Metab, August; 299(2):E145-61], [Calvo et al 2008, J Appl Physiol 2008 May; 104(5):1304-12]. Thus, increasing mitochondrial function and biogenesis is a highly relevant strategy for improving exercise and endurance performance in relation to sport.

Aging is an inevitable biological process characterized by the progressive deterioration of a variety of physiological functions, rendering the aging person increasingly frail and susceptible to diseases. The aging process is linked to increasingly dysfunctional mitochondria by a decrease in the rate of mitochondrial oxidative phosphorylation, increase in the capacity of mitochondria to produce ROS, and impairment of the mitochondrial oxidation of specific substrates. As a result, these age-induced alterations in mitochondrial function impair energy production as well as increase the production of toxic reactive oxygen intermediates [Marcovina 2013, Transl Res. February; 161(2):73-84]. The age-related decline of mitochondrial capacity for oxidative phosphorylation and accumulation of mitochondrial DNA mutations has been linked to the pathogenesis of a range of age-related pathological alterations including alopecia, osteoporosis, kyphosis, cardiomyopathy, anemia, gonadal atrophy and sarcopeniea [Desler 2012, Journal of Aging Research, 2012:1-9], and mitochondria dysfunction has been linked to most age-related diseases such as neurodegeneration, cardiovascular disease and diabetes.

Reductions in skeletal muscle function occur during the course of healthy aging as well as with bed rest or diverse diseases such as cancer, muscular dystrophy, and heart failure. Muscle fatigue as symptom of reduced muscle function is a common symptom during sport and exercise activities, but is also increasingly observed as a secondary outcome in many diseases and health conditions during performance of everyday activities. However, there are no accepted pharmacologic therapies to improve impaired skeletal muscle function. Thus, within aged or sedentary skeletal muscle, there is a significant loss in the number of fibres and demonstrable biochemical and morphological abnormalities. Several large-scale studies on skeletal muscle biopsies from humans of ages ranging from 17 to 91 years have shown a significant age-related decline in mitochondrial respiratory capacity. The substantial fall in mitochondrial respiratory capacity in ageing muscle may contribute to the reduced exercise capacity in elderly people and the associated increased risk of diseases associated with an increasingly sedentary life style. Also, mitochondrial changes may underlie not only a loss of muscle function with age, but also other common age-associated pathologies increasing the risk of disease such as ectopic lipid infiltration, systemic inflammation, and insulin resistance. [Desler 2012, Journal of Aging Research, 2012:1-9], [Scheibye-Knudsen et al. 2013, Aging, March, Vol. 5 No. 3:192-208], [Peterson et al 2012, Journal of Aging Research, p 1-20], [Boffoli et al 1994, Biochim Biophys Acta., April 12; 1226(1):73-82]. As previously mentioned, PGC-1α is a key regulator of mitochondrial biogenesis and function, and it has been shown that lifelong training preserves mitochondrial DNA and PGC-1α whereas lifelong sedentary behavior reduces such markers of mitochondrial content. Furthermore, it has been shown that despite the mitochondrial dysfunction observed with sedentary ageing, muscles from sedentary elderly individuals retain the capacity to activate the acute signaling pathways associated with regulating the early processes of mitochondrial biogenesis [Cobley 2012, Biogerontology. 13(6):621-631]. Hence, improvement of mitochondrial biogenesis and function for instance through activation of PGC-1α by inhibition of PDE4 and PDE5 in the elderly as well as during bed rest or diseases or conditions that impairs muscular function, is highly relevant.

The central nervous system is particularly prone to mitochondrial dysfunction and augmentation of mitochondrial function may play a pivotal role in a range of CNS-disorders. Exhausting the reserve respiratory capacity of a neuron can have fatal consequences. Resting neurons utilize approximately 6% of its maximal respiratory capacity, while firing neurons utilize up to 80%. Therefore, subtle aging-related decreases in spare respiratory capacity increase neuronal vulnerability towards bioenergetic exhaustion, predisposing the tissue for diseases. Hence, mitochondrial abnormalities occur in persons with various neurodegenerative diseases and distinct mitochondrial abnormalities are characteristic of particular disorders. This is the case for common age-related disorders such as Alzheimer's disease. Alzheimer's disease is a major problem in the global aging population with more than 25 million people affected by dementia, most suffering from Alzheimer's disease. In the United States alone, Alzheimer's disease affects approximately 5.4 million people and the number is projected to reach 12-16 million by the year 2050. In the United States in 2011, the cost of health care, long-term care, and hospice services for people aged 65 years and older with Alzheimer's disease and other dementias was expected to be $183 billion. Increasing evidence links Alzheimer's disease with mitochondrial dysfunction. Rodent models of the neurodegenerative Alzheimer's disease show that deficiency in mitochondrial respiration precedes the pathology of the disease. Alzheimer's disease is also accompanied by decreased expression and activity of enzymes involved in mitochondrial bioenergetics. Correspondingly, a decline of brain metabolism is detectable in Alzheimer's disease patients as early as a decade before diagnosis. Besides functional changes, extensive literature indicates mitochondrial structural dynamics are also altered in Alzheimer's disease patients. Other neurodegenerative diseases also linked to mitochondrial dysfunction are Parkinson's disease, ALS motor neuron degeneration and Huntington's disease [Lezi 2012, Adv Exp Med Biol; 942:269-286], [Desler 2012, Journal of Aging Research; 2012:1-9].

Ribes is a genus of about 150 species of flowering plants native throughout the temperate regions of the Northern Hemisphere. It is usually treated as the only genus in the family Grossulariaceae. The species *Ribes rubrum* and *Ribes nigrum* are widely cultivated due to their production of the edible redcurrants, blackcurrants, greencurrants and whitecurrants. A variety of subspecies and numerous cultivars are recognized. These berries have a widespread utility in the food and beverages industries, e.g. in the form of juice.

In 2002 Lu et al discovered the two nitrile alkaloids nigrumin-5-p-coumarate [systematic name (E)-(E)-2-cyano-4-(β-D-glucopyranosyloxy)but-2-en-1-yl 3-(4-hydroxyphenyl)acrylate] and nigrumin-5-ferulate [systematic name (E)-(E)-2-cyano-4-(β-D-glucopyranosyloxy)but-2-en-1-yl 3-(4-hydroxy-3-methoxyphenyl)acrylate] in the seeds of *Ribes nigrum* [Lu 2002, Phytochemistry; 59(4):465-8].

In 2007 Schwartz et al discovered the two nitrile alkaloids with the systematic names (E)-2-cyano-4-(β-D-glucopyranosyloxy)but-2-en-1-yl 4-hydroxy-3-methoxybenzoate and (E)-2-cyano-4-(β-D-glucopyranosyloxy)but-2-en-1-yl'4-hydroxybenzoate together with the indole alkaloids with the systematic names 1-β-D-glucopyranosyl-1H-indole-3-acetic acid and 1-β-D-glucopyranosyl-1H-indole-3-acetic acid methyl ester, which were all observed to contribute to the bitter taste of redcurrants [Schwarz 2007, J Agric Food Chem; 55:1405-1410].

None of the alkaloids found in the mentioned *Ribes* species have been attributed to any medicinal properties.

SUMMARY OF THE INVENTION

The present invention relates to the discovery of a novel highly bioactive nitrile alkaloid with the systematic name (E)-(E)-2-cyano-4-(((2R,3R,4S,5S,6R)-3,4,5-trihydroxy-6-(hydroxymethyl)tetrahydro-2H-pyran-2-yl)oxy)but-2-en-1-yl 3-(3,4-dihydroxyphenyl)acrylate (in the following referred to as "Ribetril A"):

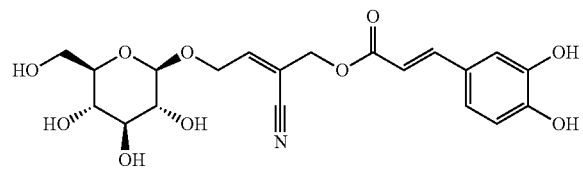 [SMILES: N#C/C(=C\CO[C@@H]1O[C@H](CO)[C@@H](O)[C@H](O)[C@H]1O)COC(=O)/C=C/c1ccc(O)c(O)c1]

The inventors have isolated the compound from several species of *Ribes*.

The novel alkaloid Ribetril A displays a surprisingly strong bioactivity and as demonstrated in example 3 it displays a 48 and 118 times lower active concentration (IC-50) as compared to the two known structural analogs with the same phenyl-acrylic acid backbone.

The present invention further relates to the surprising discovery that highly bioactive alkaloid fractions can be obtained from the berries and leaves of *Ribes*, e.g. *Ribes rubrum* and *Ribes nigrum*. Such alkaloid fractions obtainable from *Ribes* display strong inhibitory effects on IKK-β, PDE4 and PDE5 in-vitro at low concentrations as demonstrated in example 3, example 4 and example 5. In addition, cellular experiments have demonstrated a highly surprising stimulating effect on mitochondrial biogenesis and spare respiratory capacity as demonstrated in example 6, 7 and 8.

Besides, or instead of, Ribetril A the bioactive alkaloid fractions of the invention optionally comprise the previously described 4 nitrile alkaloids:

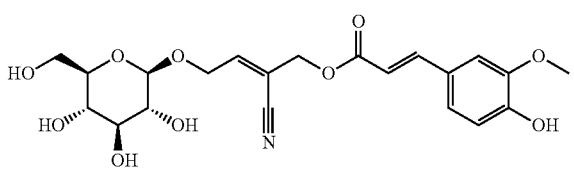 [SMILES: COc1cc(/C=C/C(=O)OC/C(C#N)=C/CO[C@@H]2O[C@H](CO)[C@@H](O)[C@H](O)[C@H]2O)ccc1O]

Systematic name: (E)-(E)-2-cyano-4-(beta-D-glucopyranosyloxy)but-2-en-1-yl 3-(4-hydroxy-3-methoxyphenyl)acrylate (in the following referred to as "Ribetril B")

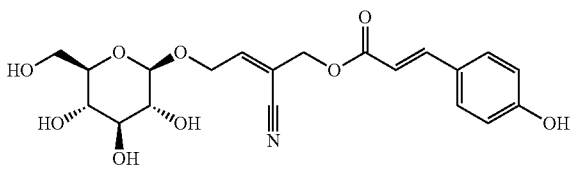

Systematic name: (E)-(E)-2-cyano-4-(beta-D-glucopyranosyloxy)but-2-en-1-yl 3-(4-hydroxyphenyl)acrylate (in the following referred to as "Ribetril C")

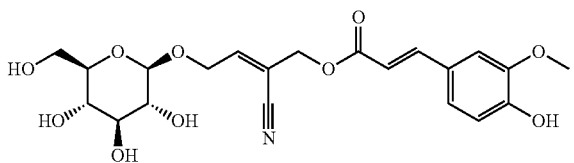 [SMILES: COc1cc(/C=C/C(=O)OC/C(C#N)=C/CO[C@@H]2O[C@H](CO)[C@@H](O)[C@H](O)[C@H]2O)ccc1O]

Systematic name: (E)-2-cyano-4-(beta-D-glucopyranosyloxy)but-2-en-1-yl 4-hydroxy-3-methoxybenzoate (in the following referred to as "Ribetril D")

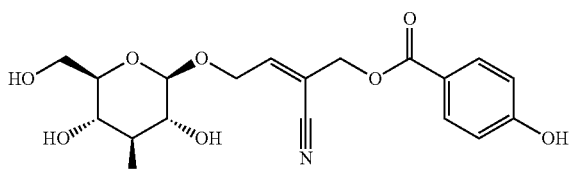

Systematic name: (E)-2-cyano-4-(beta-D-glucopyranosyloxy)but-2-en-1-yl 4-hydroxybenzoate (in the following referred to as "Ribetril E")

Furthermore the alkaloid fractions of the invention may comprise the following previously described indole alkaloids:

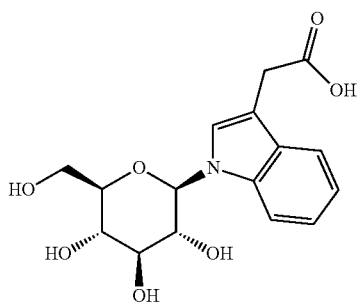 [SMILES: O=C(O)Cc1cn([C@@H]2O[C@H](CO)[C@@H](O)[C@H](O)[C@H]2O)c2ccccc12]

Systematic name: 2-(1-((2R,3R,4S,5S,6R)-3,4,5-trihydroxy-6-(hydroxymethyl)tetrahydro-2H-pyran-2-yl)-1H-indol-3-yl)acetic acid (in the following referred to as "Glucoindol A")

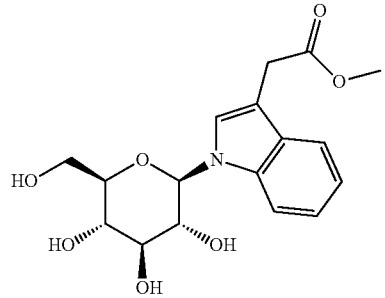 [SMILES: COC(=O)Cc1cn([C@@H]2O[C@H](CO)[C@@H](O)[C@H](O)[C@H]2O)c2ccccc12]

Systematic name: methyl 2-(1-((2R,3R,4S,5S,6R)-3,4,5-trihydroxy-6-(hydroxymethyl)tetrahydro-2H-pyran-2-yl)-1H-indol-3-yl)acetate (in the following referred to as "Glucoindol B")

None of these alkaloids have previously been attributed to medicinal effects or health promoting effects.

As demonstrated in example 1, the alkaloids of the invention are present only in negligible amounts in the *Ribes* berries in the natural form e.g. typically 0-0.8 ppm of Ribetril A and 0.5-1.5 ppm of Ribetrils A, B, C, D and E in total. Similar negligible levels of Glucoindols are found, e.g. typically 3.2-6.9 ppm.

According to the present invention, innovative concentrates or extracts of *Ribes* appear to be necessary to obtain a product that can provide physiologically active levels of the active *Ribes* alkaloids of the invention.

Surprisingly, the present inventors have found that such *Ribes* alkaloid fractions have strong health promoting effects when administered in sufficient amount to mammals in vivo, which the inventors hypothesize are related to the beforementioned inhibitory effects on IKK-β, PDE4 and PDE5, or the stimulating effect on mitochondrial biogenesis and spare respiratory capacity. Accordingly, the inventors have found that the alkaloid fractions of the invention display strong wound healing properties. While existing treatments are predominantly topically applied, the *Ribes* alkaloid fractions appear to be effective systemic wound healing agents, without ruling out topical application.

This is convincingly demonstrated and confirmed in example 11 where an orally administered *Ribes* alkaloid fraction of the invention corresponding to a daily dose of 112 μg/kg of Ribetril A and 492 μg/kg total Ribetrils as well as 240 μg/kg total Glucoindols provided a significantly faster healing of large cutaneous excisional wounds in groups of mice as compared to vehicle treated control mice in two identical experiments with a highly similar outcome. Three days after excisional injury the degree of wound closure was 78% higher in the *Ribes* alkaloid treated group as compared to the vehicle treated group and after 5 days the degree of wound closure was more than twice as high in the *Ribes* alkaloid treated group as compared to the vehicle treated group. In the first experiment, the average time to wound half closure was 5.9 days in the *Ribes* alkaloid treated group as compared to 8.3 days in the control group. In the second experiment the average time to wound half closure was 6.0 days in the *Ribes* alkaloid treated group as compared to 8.2 days in the vehicle treated control group. All of these effects were statistically significant (P<0.05).

In example 12, a dose-response relationship of *Ribes* alkaloids on wound healing was indicated since a high dose alkaloid preparation providing a daily dose of 492 µg/kg total Ribetrils and 240 µg/kg total Glucoindols was compared to an alkaloid preparation of the invention providing 18 µg/kg total Ribetrils as well as 97 µg/kg total Glucoindols. After pretreatment both of these groups provided a statistically significant effect on the average time to wound half closure (7.1 days in the high dose and 7.9 days in the low dose as compared to 9.3 days in the vehicle treated group, indicating a dose-response relationship).

In example 13, a potentially synergistic effect of two different *Ribes* fractions of the invention was indicated, since a 50/50 combination by weight of a *Ribes rubrum* derived concentrate (Glucoindol dominated chemical profile) and a *Ribed nigrum* derived concentrate (Ribetril dominated chemical profile), performed an even more pronounced wound healing effect (average time to wound half closure 6.4 day) than the individual *Ribes* alkaloid concentrates of the invention (the average time to wound half closure 7.2 days and 7.1 days) and the vehicle control (average time to wound half closure 7.9 days).

In example 14, a significant wound healing effect in a model of chronic wounds in diabetic mice was demonstrated by two different *Ribes* alkaloid formulations of the invention. In example 15, it was demonstrated that the wound healing effect of orally administered *Ribes* alkaloid extracts of the invention can be found across species and gender variations. In example 17, it was demonstrated that an impressive, fast onsetting and statistically significant wound healing effect could also be found on acute wounds in a human subject serving as it's own control and receiving an oral nutritive product comprising a *Ribes* alkaloid fraction as prepared in example 16. The degree of wound healing enhancement was comparable to the effect observed in the rodent models.

Thus, the inventors have found that alkaloids of the invention may be used as wound healing agents in acute as well as chronic hard-to-heal wounds, and have the significant advantage of being active upon oral administration. Faster wound healing of acute wounds is highly relevant since the risk of infection and development of hard-to-heal wounds decreases with increasing wound healing speed. Furthermore, faster healing of chronic wounds present a much sought for solution to the major treatment challenge and huge economic burden to the health care system of chronic wound management.

In example 9, a *Ribes* alkaloid composition of the invention was tested for possible hypocholesterolemic effect in hyperlipidemic guinea pigs induced by a high fat diet. The *Ribes* alkaloid fraction at 112 µg/kg of Ribetril A and 492 µg/kg total Ribetrils as well as 240 µg/kg total Glucoindols and the positive reference compound Atorvastatin at 10 mg/kg were administered orally once daily for 28 consecutive days. Blood was drawn on days 1 before the first dosing, 15 and 29 from overnight-fasted animals for measurements of serum total cholesterol, low density lipoprotein (LDL) and triglyceride levels. Surprisingly, after only 15 days the *Ribes* alkaloid treated animals displayed 32% reduction of triglyceride levels ($P<0.05$), which was further increased to a 50% reduction after 29 days of treatment as compared to the vehicle control group ($P<0.05$). Furthermore, the *Ribes* alkaloid treated group displayed a 40% decrease of serum total cholesterol ($P<0.05$) and a 39% decrease of LDL ($P<0.05$) after 29 days of treatment, which was of the same order of magnitude as the positive control Atorvastatin. Taken together, by lowering both triglycride levels and total cholesterol, the *Ribes* alkaloid fraction of the invention was superior to atorvastatin, which did not display a significant decreasing effect on triglyceride levels. This is most likely due to the completely different mechanism of action of the alkaloids of the invention. The significant triglyceride, LDL and total cholesterol lowering effects were convincingly confirmed in a human subject as demonstrated in example 19.

In example 10, a *Ribes* alkaloid composition of the invention was tested for possible hypoglycemic effect in BKS Cg-Lepr db/Lepr db mice, a model of non-insulin dependent diabetes mellitus. Groups of 6-12 mice were treated with a daily dose of 112 µg/kg of Ribetril A and 492 µg/kg total Ribetrils as well as 240 µg/kg total Glucoindols of the *Ribes* alkaloid fraction of the invention or 300 mg/kg of the positive antidiabetic reference compound metformin for 14 consecutive days and compared to a vehicle treated control group. Serum glucose levels and serum insulin were measured before treatment on Day 1, and at 90 min after the daily dosing on Day 7 and Day 14. The *Ribes* alkaloid composition treated group displayed a metformin like bloodsugar reduction at day 14 ($P<0.05$) without affecting insulin levels.

In example 6, two *Ribes* alkaloid compositions of the invention were tested for their ability to enhance mitochondrial biogenesis in cultured muscle cells. In this experiment, it was convincingly demonstrated that 48 hours of incubation with the *Ribes* alkaloid compositions significantly increased mitochondrial biogenesis at physiologically relevant concentrations. Increase of mitochondrial biogenesis in muscle cells is highly relevant when an increased capacity is needed to handle stressful conditions and/or the high energy need in working muscles, or when a decrease in mitochondrial amount and function due to inactivity, illness or age is impairing the functionality of the muscle cells.

In example 7 and 8, three *Ribes* alkaloid fractions of the invention were tested for their ability to increase spare respiratory capacity in cultured muscle cells. Surprisingly, it was demonstrated that the *Ribes* alkaloid fractions of the invention, RAP13, RAP14 and RAP15, significantly increased the spare respiratory capacity of C2C12 cells at physiologically relevant concentrations when the cultivated muscle cells were exposed to a standardized mitochondrial stress test. This is extremely interesting since if the spare respiratory capacity of the cells is not sufficient to provide the required ATP, affected cells will function suboptimally and even risk being driven into senescence or cell death. An increased spare respiratory capacity in muscle cells is therefore extremely valuable to improve endurance in muscle function and capability, resistance to stress as well as counteracting the effects of senescence and inactivity.

It is becoming widely recognized that mitochondria is a main crossroad in the regulation of a many important physiological processes which may deteriorate into pathological conditions if compromised. Furthermore, mitchondria represent the endstation in the energy yielding metabolism, transforming sugars and lipids to ATP. The combined effects of the *Ribes* alkaloid fractions on both mitochondrial biogenesis and spare respiratory capacity offer an entirely new method for optimizing mitochondrial function both in pathological conditions associated with dysfunctional mitochondria, as well as in various areas of health improvement, sports and muscle performance, and energy-requiring conditions. Furthermore, mitochondrial dysfunction and decline of spare respiratory capacity has been linked directly to the deterioration of various physiological functions during aging leading to alopecia, osteoporosis, kyphosis, cardiomyopathy, anemia, gonadal atrophy and sarcopeniea. Additionally, the central nervous system is a highly energy-demanding tissue particularly vulnerable to mitochondrial dysfunction and aging-related decreases in spare respiratory capacity predisposes this tissue for diseases. Hence, mitochondrial dysfunctions occur in patients with various neurodegenerative diseases including Alzheimer's disease where a decline of brain metabolism is detectable as early as a decade before diagnosis. Other neurodegenerative diseases such as Parkinson's disease, ALS motor neuron degeneration and Huntington's are also linked to mitochondrial dysfunction. Regarding all these age-related physiological deteriorations and ailments, the *Ribes* alkaloid fractions of the invention offer a new promising intervention principle.

The application of the *Ribes* alkaloids and alkaloid fractions of the invention within the field of aging and neurodegeneration is strongly supported by example 23 and 27. In example 23, the nutritive product comprising *Ribes* alkaloids of the invention elicited a decreased sense of tiredness and fatigue in a 81 year old man during sports performance, increasing his ability to continue playing tennis 50% longer under standardized conditions as compared to before taking the nutritive product formulation of the *Ribes* alkaloid fraction of the invention. This indicates a significant improving effect on age-related physical and muscular fatigue by the nutritive product comprising *Ribes* alkaloids of the invention.

In example 27, the continuous physical and mental fatigue which had relentlessly persisted during the rehabilitation period of a 75-year old woman who had suffered a traumatic brain haemorrhage, was dramatically decreased within a week of taking the nutritive product comprising *Ribes* alkaloids of the invention. This indicates a major contribution to improvement and normalization of the functioning of the central nervous system by the nutritive product comprising *Ribes* alkaloids of the invention, which was very significant since the subject was able to resume her daily routines and activities at a level comparable to her previous capacity with an amazing speed.

Based on strong existing evidence that improving mitochondrial biogenesis and function is a key aspect in optimizing endurance and sport performance, it is obvious that the markedly improved performances in three athletic test subjects in examples 24, 25 and 26 can be ascribed to the enhanced mitochondrial biogenesis and spare respiratory capacity obtained in muscle cells as demonstrated in example 6, 7 and 8 and that the *Ribes* alkaloid compositions of the invention can be applied in the oral management for enhancing highly relevant aspects of muscle physiology in relation to endurance and sports performance. This is strongly supported by example 24, in which a 16 year old male athlete swimmer after 14 days of taking the nutritive product comprising *Ribes* alkaloids of the invention improved his overall standard swim test time by 6.4% with an even more impressive improvement in the second half of the swim test of 12.1%. This was an exceptional improvement which otherwise would only be obtainable through a highly intensified training regime over a longer period of time, demonstrating the physical performance and endurance enhancing effects of the nutritive product comprising *Ribes* alkaloids of the invention.

In example 25, a 28 year old physically well-trained male long-distance runner obtained an improvement in his calculated VO2 Max of 7.8% in a standard Conconi test after only 7 days of oral administration of the nutritive product of the invention. This was an exceptional improvement, considering the subject's high level of fitness and consequently very high VO2 Max before treatment, which would normally only be obtainable through hard interval training for a longer period of time, demonstrating the enhancing effect on VO2 Max in athletes of the of the nutritive product comprising *Ribes* alkaloids of the invention.

In example 26, after only 4 days of daily oral administration of the nutritive product comprising *Ribes* alkaloids of the invention, a 48 year old physically well-trained man with a well-established anaerobic threshold heart rate of 175 bpm during long distance high intensity cycle training improved his average heart rate 5.7% to 185 bpm for 20 minutes during a long distance high intensity training pass, indicating a fast onset of action and an increased endurance and lactate threshold exerted by the nutritive product comprising *Ribes* alkaloids of the invention.

In example 3 and 4, it was demonstrated that *Ribes* alkaloid fractions of the invention were able to dose-dependently inhibit IKK-β and PDE4, enzymes which are both highly linked to the propagation of various types of inflammation. The physiological relevance of these effects is strongly supported by example 21 in which a 47 year old man who suffered from osteoarthritis in the first carpometacarpal joint of left hand with increasing symptoms of pain, swelling, stiffness and joint dysfunction for more than 2 years had been offered surgery to relieve his condition. The subject initiated an oral treatment with the nutritive product comprising *Ribes* alkaloids of the invention, and gradually, pain and swelling of the afflicted joint decreased so that after taking the nutritive product comprising *Ribes* alkaloids of the invention for 12 weeks all symptoms of osteoarthritis were entirely absent. The subject was able to use his thumb with no restrictions in all kinds of the daily activities and manual tasks without causing pain or any other symptoms from the carpometacarpal joint (pain estimated to be 100% reduced). Since the symptoms of osteoarthritis remained absent during another 8 weeks of treatment, the operation was cancelled.

In example 22, a 43 year old woman with a diagnosis of osteoarthritis in first metatarsophalangeal joint of right foot for 4 years and left foot for 3 years had suffered from increasing pain and reduced joint mobility. After 2 weeks of oral administration of the nutritive product comprising *Ribes* alkaloids of the invention, the pains in the first metatarsophalangeal joint of both feet were reduced by 80% as estimated by the subject and the mobility of the joints were almost back to normal. This pronounced improvement in the symptoms of osteoarthritis remained stable during the next two weeks of treatment, indicating a robust and lasting effect of the treatment. The subject had not experienced an improvement of the condition over the last 4 years; on the contrary the condition had been worsening. Example 21 and 22 clearly indicate an anti-inflammatory activity on osteoarthritis and a promoting effect on joint and cartilage health of the nutritive product comprising a *Ribes* alkaloid fraction of the invention.

Thus, the inventors have found that the alkaloids and *Ribes* alkaloid fractions of the invention comprise a novel bioactive principle for the treatment or prevention of a cardiovascular disease, a dyslipidemic disorder, a pre-diabetic disorder, type 2 diabetes, metabolic syndrome, inflammatory conditions such as arthritis, as well as for the enhancement of cognitive and neuronal health, improvement of age-related decline in physical endurance and perceived energy levels, and endurance, VO2 Max and lactate threshold during sports performance.

Certain aspects and embodiments of the present invention are provided in the items and claims. Additional aspects and embodiments are described herein. Features of the aspects, embodiments and items or claims may be combined.

According to an aspect, the invention concerns the subject-matter of item 1.

According to another aspect, the invention concerns the subject-matter of item 3.

According to an aspect, the invention concerns the subject-matter of item 10.

According to an additional aspect, the invention concerns the subject-matter of item 16.

According to another aspect, the invention concerns the subject-matter of item 39.

According to another aspect, the invention concerns the subject-matter of item 40.

According to another aspect, the invention concerns the subject-matter of item 41.

According to another aspect, the invention concerns the subject-matter of item 42.

According to another aspect, the invention concerns the subject-matter of item 45.

According to another aspect, the invention concerns the subject-matter of item 46.

According to another aspect, the invention concerns the subject-matter of item 59.

According to another aspect, the invention concerns the subject-matter of item 61.

According to another aspect, the invention concerns the subject-matter of item 70.

According to another aspect, the invention concerns the subject-matter of item 84.

DETAILED DESCRIPTION OF THE INVENTION

Figure 1:
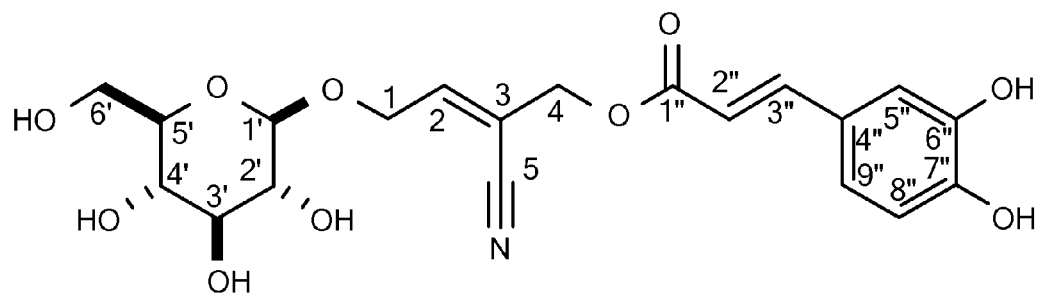
FIG. 1 shows the structure of Ribetril A with the numbering used for assignment of 1H and 13C resonances. Note that the numbering of Ribetril A differs from the strict IUPAC numbering.

The foregoing and other aspects of the present invention will now be described in more detail with respect to other embodiments described herein. It should be appreciated that the invention can be embodied in different forms and should not be construed as limited to the embodiments set forth herein.

Additional embodiments according to the invention are mentioned in the items.

All cited references are incorporated by reference herein.

Unless otherwise defined, all technical and scientific terms used herein have the same meaning as commonly understood by one of ordinary skill in the art to which this invention pertains. The terminology used in the description of the invention herein is for the purpose of describing particular embodiments only and is not intended to be limiting of the invention. As used in the description of the invention and the items or claims set forth herein, the singular forms "a", "an" and "the" are intended to include the plural forms as well unless the text clearly indicates otherwise. The person skilled in the art understands that while the plural or singular form of nouns is used in certain places, the plural may cover the singular, and vice-versa. As used herein, the term "and/or" includes any and all combinations of one or more of the associated listed items.

All systematic chemical names used for the alkaloids of the invention herein have been generated according to the Cahn-Ingold-Prelog rules for stereochemistry by application of the ChemBioDraw Ultra 12.0 software from CambridgeS oft.

For other chemicals, their commonly used names are applied, e.g. in the case of the flavonols, phenolic acids, proanthocyanidins and anthocyanidins occurring in *Ribes*.

The following phrases, terms and definitions are used herein:

The term "*Ribes*" is meant to encompass a *Ribes* species or cultivar thereof suitable for the production of alkaloids and alkaloids fraction of the invention. Non-limiting examples of suitable species and subspecies include *Ribes rubrum, Ribes nigrum, Ribes sativum, Ribes petraeum, Ribes multiflorum, Ribes longeracemosum, Ribes sylvestre, Ribes spicatum, Ribes vulgare, Ribes×pallidum, Ribes×nidigrolaria, Ribes europaeum, Ribes scandinavicum, Ribes sibiricum, Ribes triste, Ribes hudsonianum* Rich and *Ribes americanum* Mill. Non-limiting examples of cultivars are listed in the United States department of Agriculture's overview of all *Ribes* Cultivars and Selections and may be found at the homepage of USDA (www.ars.usda.gov/Main/docs.htm?docid=11353).

The terms "alkaloid fraction" and "*Ribes* alkaloid" is meant to encompass a single isolated alkaloid or a mixture of two, three, four, five, six or all seven alkaloids of the invention. The alkaloids of the invention may be obtained from any available natural source, manufactured by recombinant technology or manufactured synthetically. According to the present invention the alkaloids are defined as the molecules shown in the figures above.

As commonly understood in chemistry, the term "mass fraction" ($W_i$) refers to the ratio of one substance with mass $M_i$ to the mass of the total mixture $M_{tot}$ defined as:

$$Wi = \frac{Mi}{Mtot}$$

Here the mass fraction is typically expressed as percent (%).

The term "therapeutic use" refers to any application of the invention related to "treatment" as defined below.

The term "nutritive product" refers to a food or non-food product that has an alkaloid or alkaloid fraction of the invention added, or alternatively an increased amount of the alkaloid or alkaloid fraction, as compared to the naturally occurring form, to give it a physiological or medical benefit, which may be a therapeutic or non-therapeutic benefit.

A nutritive product in the form of a "food product" in the present context refers to a food designed to provide additional benefits to the organism other than a purely nutritional effect, e.g. a physiological benefit, a medical benefit, a therapeutic benefit or a non-therapeutic benefit as defined above. Non-limiting examples include products commonly referred to as functional foods, food supplements, dietary supplements, nutritional supplements, nutraceuticals or medical foods. The regulatory definition and denomination of such products vary significantly in different parts of the world and is under regular change. Such products may be in the form of specialized food preparations or common foods or beverages.

A nutritive product in the form of a "non-food product" refers to products such as for oral administration, where non-limiting examples are tablets, capsules, powders, chewing gum and lozenges; or products such as for topical administration, where non-limiting examples are ointments, creams, lotions, gels, solutions or shampoos.

The term "pomace" refers to the skins, pulp, seeds, and stems left after pressing for juice of the berries.

A "physiological benefit" refers to the effects of a nutritive product on physiological processes within or without the normal physiological range including:

Maintenance of, contribution to or enhancement of physiological processes or parameters within the normal physiological range, or reduction or enhancement of abnormally high or low physiological processes or parameters, e.g. stabilization or normalization of physiological processes or parameters. Non-limiting examples of physiological benefits are maintenance or improvement of muscle endurance or muscle strength, maintenance or improvement of cognitive function, such a short term memory, maintenance or improvement of healing processes in the body, e.g. healing of wounds or other types of tissue damage, reduction or prevention of the risks of illness and age-related conditions and/or support of the healing process during illness and disease, maintenance or improvement of mitochondrial function or counteraction of aging or signs of aging.

A "medical benefit" refers to the effects of a nutritive product on pathological processes with the purpose of preventing or counteracting a disease or a physiological process potentially leading to a disease. Non-limiting examples of medical benefits are improvement of mitochondrial biogenesis and function in muscle cells counteracting deterioration of muscle mass in sedentary patients, e.g. during hospitalization, counteracting sarcopenia (age related loss of muscle mass) by promoting the endurance necessary to activate the elderly physically. Another medical benefit of a nutritive product could be improvement of cartilage health and prevention of the inflammatory processes driving osteoarthritis, the most common form of arthritis, as well as improving cardiovascular health and counteracting major risk factors, e.g. by reducing unhealthy blood lipids.

A "therapeutic benefit" refers to normalization or counteraction of physiological processes or parameters outside the normal range, e.g. in relation to a disease or disease process.

A "non-therapeutic benefit" refers to normalization or counteraction of physiological processes or parameters within the normal range, optimizing sports endurance, etc, etc.

The term "treat" and "treatment" refers to the application of the present invention resulting in a reduction of the severity of the subject's condition or a least the condition is partially improved or ameliorated and/or that so alleviation, mitigation or decrease of at least one clinical symptom is achieved and/or there is a delay in the progression of the condition and/or prevention or delay of the onset of the condition. Thus, the term "treat" refers to both preventionally and therapeutic treatment regimes.

The term "wound" refers to the following non-limiting classes of wounds:

An acute or chronic dermal wound;

An acute or chronic wound related to body tissue selected among muscles, fat, bones, inner organs, nerve tissue, cartilage, joints, arteries, veins, the gastro-intestinal tract, mucus membranes and eyes;

An acute wound selected among traumatic wounds, surgical wounds, infected wounds, mucus membranes wounds, burn wounds, wounds caused by an underlying condition and corneal ulcers;

A chronic wound selected among surgical wounds, traumatic wounds, burn wounds, infected or contaminated wounds, venous ulcers, arterial ulcers, mixed venous-arterial ulcers, pressure ulcers, diabetic ulcers, neuropathic ulcers, fistulas, immunological ulcers, malignant ulcers, dermatitis ulcers, radiation ulcers, pyoderma gangrenosum and skin graft treated wounds;

A traumatic wound selected among cuts, crushes, punctures, lacerations, contusions, abrasions and avulsions;

A wound which is poor and/or slowly healing;

A wound in a human or animal.

Inhibition of IKK-$\beta$ or PDE4 is measured in vitro according to the methods described in example 3 and example 4. In some embodiments the alkaloid fractions, extracts of *Ribes* or compositions of the invention may have a predominant effect on either IKK-$\beta$ or PDE4, or have an effect which is independent of these mechanisms of action.

The term "reducing", "reduce", "inhibiting" or "inhibitory" refers to a decrease or diminishment in the specified activity of at least about 10%, 25%, 35%, 40%, 50%, 60%, 75%, 80%, 90%, 95% or more. In some embodiments, the reduction results in little or essentially no detectable activity (at most, an insignificant amount, e.g. less than about 10% or even 5%). The term "an effective amount" refers to an amount of the alkaloid fractions, extract, juice or concentrate of *Ribes* or compositions of the present invention that is sufficient to produce the desired effect. The effective amount will vary with the application for which the alkaloid fractions, extract, juice or concentrate of *Ribes* or compositions are being employed, the age and physical condition of the subject, the severity of the condition, the duration of the treatment, the nature of any concurrent treatment, the carrier used, and similar factors within the knowledge and expertise of those skilled in the art.

The term "juice" refers to the liquid that is naturally contained in the *Ribes* such as the berries, stems and/or leaves, and which can be obtained by mechanically squeezing or macerating the *Ribes*.

The term "extract" refers to a mixture of substances obtained from *Ribes* especially the berries, stems and/or leaves by extraction of the *Ribes* with a solvent capable of dissolving the constituents of the extract. The *Ribes* may preferably be extracted fresh or dried. In the present invention various solvents and various extraction techniques may be used, such as percolation or maceration with the solvent, distillation or super critical extraction.

The term "concentrate" refers to a product derived from *Ribes* where the mass fraction of alkaloids is enhanced without carrying out an extraction. Non limiting examples of methods of preparing concentrates are precipitation, condensation, air drying or freeze drying.

The terms "acceptable vehicle", "pharmaceutically acceptable vehicle" or "cosmetically acceptable vehicle" refers to a component such as a carrier, diluent or excipient of a composition that is compatible with the other ingredients of the composition in that it can be combined with the compounds and/or compositions of the present invention without eliminating the biological activity of the compounds or the compositions, and is suitable for use in subjects as provided herein without undue adverse side effects. Non-limiting examples of "acceptable vehicles" include, without limitation, any of the standard pharmaceutical, food or cosmetic carriers such as water, emulsions, liniments, tablets, capsules, powders, etc. This is further meant to define a vehicle in liquid, semi-solid or solid form.

The term "medical device" refers to a device as regulatorily defined.

The term "food composition" refers to any type of liquid or solid form of food or beverage ingredient or finished foods and beverages, including soft drinks, juices, smoothies and dairy products, etc. The term "food composition" further encompasses any type of finished food or beverage, including functional foods, medical foods, dietary supplements and nutraceuticals. The term "support" is used interchangeably with the terms "maintain", "restore" or "preserve". The term "decrease" is used interchangeably with the terms "lower", "counteract", "decrease" or "reduce".

The term "normalize" is used interchangeably with the terms "regulate" or "modulate".

The term "improve" is used interchangeably with the terms "enhance", "promote", "stimulate", "increase" or "raise"

Additional Aspects and Embodiments

The present invention inter alia provides the new highly bioactive nitrile alkaloid Ribetril A according to formula (I):

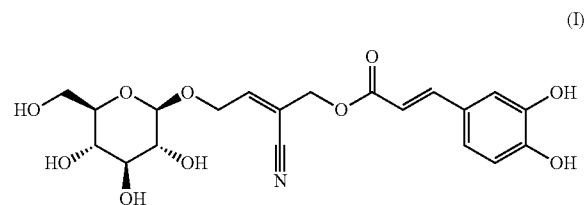 [SMILES: N#C/C(=C\CO[C@@H]1O[C@H](CO)[C@@H](O)[C@H](O)[C@H]1O)COC(=O)/C=C/c1ccc(O)c(O)c1]

(I)

In an other aspect the invention provides an alkaloid fraction derivable from *Ribes*, comprising Ribetril A and optionally:
i) at least one compound according to formula (II):

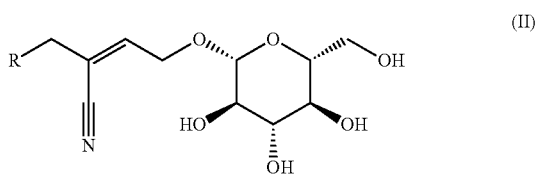

(II)

wherein
R is an acyloxy moiety derived from an acid selected from the group consisting of 4-hydroxy-3-methoxybenzoic acid, 4-hydroxybenzoic acid, (E)-3-(4-hydroxy-3-methoxyphenyl)acrylic acid and (E)-3-(4-hydroxyphenyl)acrylic acid; and/or
ii) at least one compound according to formula (III):

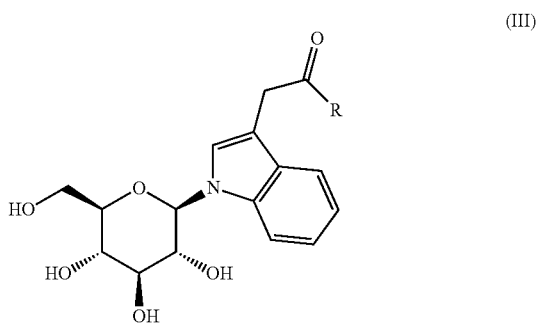

(III)

wherein R is OH or $OCH_3$;
In preferred embodiments the alkaloid fraction is derived from a *Ribes* selected among *Ribes Rubrum* and *Ribes nigrum*. In some embodiments the alkaloid fraction may be preferably derived from a single *Ribes* selected among *Ribes Rubrum* and *Ribes nigrum*. In other embodiments the alkaloid fraction may preferably be derived from two or three *Ribes* selected among *Ribes rubrum, Ribes nigrum* or other species of *Ribes*. Thus, the chemical composition of the alkaloid fraction of the invention may be optimized for specific purposes by the selection of the *Ribes* it is derived from.

In some cases specific cultivars may be preferred.

More specifically the invention provides an alkaloid fraction, wherein the at least one compound according to formula (II) is selected from the group consisting of Ribetril B, Ribetril C, Ribetril D and Ribetril E.

More specifically the invention provides an alkaloid fraction, wherein the at least one compound according to formula (III) is selected from the group consisting of Glucoindol A and Glucoindol B.

As demonstrated in the examples the chemical composition of the alkaloid fraction of the invention may be varied through specific adjustment of the manufacturing process.

In typical embodiments the alkaloid fraction would comprise at least one compound of formula (I) and at least one compound of formula (II) or (III), wherein the weight ratio of the total amount of compounds according to formula (I) and the total amount of compounds according to formula (II) or (III) is between 1:1000 and 1000:1, more preferably between 1:100 and 100:1, more preferably between 1:50 and 50:1 and most preferably between 1:20 and 20:1.

In certain embodiments the alkaloid fraction according to the invention would comprise a total mass fraction of compounds according to formula (I) of 95%-100%.

In other embodiments the alkaloid fraction according to the invention would comprise a total mass fraction of compounds according to formula (II) of 95%-100%.

In additional embodiments the alkaloid fraction according to the invention would comprise a total mass fraction of compounds according to formula (III) of 95%-100%.

The present invention inter alia provides an extract, juice or concentrate of a *Ribes*, preferably selected among *Ribes rubrum* and *Ribes nigrum* and, comprising an increased mass fraction of the alkaloid(s) of the invention. The term "an increased mass fraction" refers to an increase of at least about 20%, 25%, 30%, 40%, 50%, 60%, 75%, 80%, 95%, 120%, 150%, 200%, 300%, 500%, 1000%, 5000%, 10000% or more.

As demonstrated in example 1, the alkaloids of the invention are present only in negligible amounts in the *Ribes* berries in the natural form e.g. typically 0-0.8 ppm of Ribetril A and 0.5-1.5 ppm of Ribetrils A, B, C, D and E in total. Similar negligible levels of Glucoindols are found, e.g. typically 3.2-6.9 ppm.

According to the present invention, innovative concentrates or extracts of *Ribes* are necessary to obtain a product that can provide physiologically active levels of the active *Ribes* alkaloids of the invention.

In some embodiments of the invention the extract, juice or concentrate of *Ribes* further comprises:
i) at least one flavonol selected from the group consisting of quercetin, myricetin, kaempferol and glucosides thereof; and/or
ii) at least one phenolic acid selected from the group consisting of p-hydroxybenzoic acid, vanillic acid, caffeic acid, p-coumaric acid, ferulic acid and glucosides thereof; and/or
iii) at least one proanthocyanidin selected from the group consisting of epicatechin, epigallocatechin and oligomers thereof; and/or
iiii) at least one anthocyanidin selected from the group consisting of cyanidin, delphinidin, and glucosides thereof.

Such additional compounds may improve the galenic properties of the product, increase the stability or even contribute to the beneficial effects of the product.

It is also appreciated by the person skilled in the art that the dosage and dosage form of an alkaloid or alkaloid fraction of the invention will vary depending on the intended use.

Guidance for the preparation of compositions of the invention can be found in:

"Remington: The science and practice of pharmacy", 21st ed. Edition, Pharmaceutical Press (20 Nov. 2011), ISBN-13: 978-0857110428;

Food Science and Technology, edited by Geoffrey Campbell-Platt, illustrated edition (11 Sep. 2009), Wiley-Blackwell, ISBN-13: 978-0632064212

Handbook of Cosmetic Science and Technology, Edited by Marc Paye, 3rd edition (3 Mar. 2009), Informa Healthcare, ISBN-13: 978-1420069631.

In another aspect the invention provides an extract, juice or concentrate of *Ribes*, comprising an increased mass fraction of the alkaloid or alkaloid fraction of the invention, as compared to- *Ribes*:

i) e.g. a mass fraction of Ribetril A of said extract, juice or concentrate of *Ribes* selected among 0.0001%-100%, 0.00025%-90%, 0.0005%-80%, 0.00025%-70%, 0.0005%-60%, 0.00075%-50%, 0.001%-45%, 0.0025%-40%, 0.005%-35%, 0.0075%-30%, 0.01%-25%, 0.025%-20, 0.05%-19%, 0.075%-18%, 0.1%-17%, 0.25%-16%, 0.5%-15%, 0.75%-14%, 1%-13%, 1.5%-12%, 2.0%-11%, 3.0%-10%, 4.0%-9.0%, 5.0%-8.0% and 6.0%-7.0%;

ii) e.g. a total mass fraction of Ribetril A, Ribetril B, Ribetril C, Ribetril D and/or Ribetril E of said extract, juice or concentrate of *Ribes* selected among 0.0002%-100%, 0.0005%-90%, 0.0008%-80%, 0.001%-70%, 0.0025%-60%, 0.005%-50%, 0.0075%-45%, 0.01%-40%, 0.025%-35%, 0.05%-30%, 0.075%-25%, 0.1%-20, 0.25%-19%, 0.5%-18%, 0.75%-17%, 1.0%-16%, 1.5%-15%, 2.0%-14%, 2.5%-13%, 3.0%-12%, 4.0%-11%, 5.0%-10%, 6.0%-9.0% and 7.0%-8.0%.

iii) e.g. a total mass fraction of Glucoindol A and/or Glucoindol B of said extract, juice or concentrate of *Ribes* selected among 0.0008%-100%, 0.001%-90%, 0.0025%-80%, 0.005%-70%, 0.0075%-60%, 0.01%-50%, 0.025%-45%, 0.05%-40%, 0.075%-35%, 0.1%-30%, 0.25%-25%, 0.5%-20, 0.75%-19%, 1.0%-18%, 1.5%-17%, 2.0%-16%, 2.5%-15%, 3.0%-14%, 3.5%-13%, 4.0%-12%, 4.5%-11%, 5.0%-10%, 6.0%-9.0% and 7.0%-8.0%.

As demonstrated in example 1 where pure alkaloids are prepared as well as diverse extracts and concentrates of *Ribes* with highly varying contents of the *Ribes* alkaloids of the invention, there are many potential embodiments of the invention.

The extracts and concentrates of the invention are preferably in liquid, powder or paste form.

In yet another aspect the present invention provides a method for manufacturing an extract or concentrate of *Ribes* comprising an alkaloid or alkaloid fraction according to the invention, comprising the steps:

i) preparing a juice or suspension of the ground berries and/or leaves;

ii) optionally extracting the juice or ground berries and/or leaves with an extraction agent;

iii) optionally removing said extraction agent and/or excessive water;

iiii) concentrating the alkaloid in order to obtain an alkaloid fraction.

In a preferred embodiment the *Ribes* is selected among *Ribes rubrum*, *Ribes nigrum* and/or combinations thereof.

In certain embodiments of the invention the suspension of ground berries may preferably be subjected to enzyme treatment to enhance the yield of the alkaloid fraction. In preferred embodiments the enzyme is selected among cellulase, amylase or pectinase. The amount of enzyme used, the adjustment of pH and/or temperature and the duration of the enzyme treatment to optimize the process would be obvious to a person skilled in the art.

In preferred embodiments of the invention the step of extracting the ground berries and/or leaves with an extraction agent, said extraction agent preferably comprises water, an organic solvent or a mixture thereof. Non-limiting examples of suitable organic solvents are methanol, ethanol, 1-propanol, 2-propanol, 1-butanol, acetone, methyl-ethyl ketone and ethyl acetate, or mixtures thereof. In certain embodiments supercritical extraction may preferably be applied, e.g. employing carbon dioxide as extraction agent.

In certain embodiments of the invention the step of concentrating the alkaloid fraction comprises centrifugation, ultrafiltration, nanofiltration, chromatography, solid-liquid extraction, liquid-liquid extraction and/or drying as demonstrated in Example 1.

In yet another aspect of the invention the alkaloid(s) of the invention may be combined in nutritive products with other active ingredients with well established beneficial health effects. Non-limiting examples of such additional ingredients are alpha-linolenic acid, Beta-glucans, chitosan, hydroxypropyl methylcellulose, pectins, glucomannan, guar gum, linoleic acid, red yeast rice, plant sterols and plant stanols, docosahexaenoic acid, eicosapentaenoic acid, biotin, folate, magnesium, niacin, thiamine, vitamin B12, vitamin C, vitamin B6, iodine, iron, zinc, carbohydrates, copper, potassium, calcium, manganese, vitamin D, protein, amino acids, chromium, pantothenic acid, phosphorus hydroxypropylmethylcellulose, alphacyclodextrin, arabinoxylan produced from wheat endosperm, water, valine, lysine, threonine, leucine, isoleucine, tryptophan, phenylalanine, methionine, cysteine, histidine, glycine, alanine, serine, cysteine, tyrosine, aspartic acid, proline, hydroxyproline, citrulline, arginine, ornithine, hydroxyglutamic acid, glutamine, glutamic acid.

EXAMPLES

Example 1

Objective

The objective of the current series of experiments was to isolate the alkaloids Ribetril A, Ribetril B, Ribetril C, Ribetril D, Ribetril E, Glucoindol A and Glucoindol B from *Ribes* and to prepare extracts, juices and concentrates of *Ribes* comprising an increased mass fraction of the alkaloid fractions of the invention.

Raw Materials, Test Compounds and Chemicals

All chemicals employed were of standard analytical grade from diverse suppliers. In special cases suppliers are specified.

All samples of- *Ribes rubrum* and *Ribes nigrum* were provided by Asiros A/S, Copenhagen, Denmark (commercially grown in Denmark, Poland or Germany) or obtained from the genetic collection Pometet, University of Copenhagen, Denmark.

Preparation of Pure Alkaloids from *Ribes* Berries 500 g of berries (either *Ribes rubrum* or *Ribes nigrum*) were grinded and homogenized followed by extraction twice with 500 ml 2-propanol for 30 minutes under homogenization employing an IKA® T25 Digital Ultraturrax running at 24000 rpm. Before further processing, the crude extract was subjected to filtration on a Buchner funnel with vacuum suction.

The next step comprised removal of the solvent on a rotary evaporator (Büchi Rotavapor R-210 equipped with vacuum controller V-850) under vacuum at 50° C.

Subsequently the extract was dissolved/dispersed in 500 ml water and subjected to liquid-liquid extraction in a separatory funnel with 500 ml heptane twice to remove unwanted lipids. Thereafter the aqueous solution of the extract was subjected to liquid-liquid extraction in a separatory funnel with 500 ml ethylacetate three times and the ethyl acetate extracts were collected.

Subsequently the ethyl acetate was removed on a rotary evaporator (Büchi Rotavapor R-210 equipped with vacuum controller V-850) under vacuum at 50° C. The solvent free ethyl acetate extract was collected and used as raw material for preparative chromatography.

Preparative Chromatography

Isolation of the pure alkaloids according to the invention was performed using a Shimadzu Prominence preparative HPLC system consisting of 2 preparative HPLC pumps (LC-20AP), a preparative manual injector (RH3725), a diode array detector (SPD-M20A), a HPLC fraction collector (FRC-10A) and a system controller. All data were recorded using the Shimadzu Labsolution Multi LC-PDA software. The separation of the compounds was achieved on a Synergy 4u Max-RP 80A column (250×21.20 mm) from Phenomenex. All solvents used were HPLC quality from commercial suppliers. The UV data were acquired as full scan UV spectra at 200-700 nm. The collection of fractions was acquired using 280 nm.

Two different mobile phase setups were used; an isocratic for crude fractionation and a gradient for the final fractionation.

The isocratic mobile phase consisted of 70% v/v water with 0.5% formic acid and 30% v/v acetonitrile with 0.5% formic acid, run time 20 min and a flow-rate of 11 ml/min.

The gradient mobile phase consisted of water with 0.5% formic acid and acetonitrile with 0.5% formic acid using a gradient from 2-90% v/v acetonitrile with 0.5% formic acid (0-125 min) and 90-2% v/v acetonitrile with 0.5% formic acid (125-126 min) and a flow-rate of 11 ml/min.

The following general procedure was used to collect the pure compounds. Between 50 and 200 mg of the crude extract was injected, the fractions were collected using the isocratic method and the fraction or fractions of interest were picked out based on the UV spectra. The purity of the fractions was determined on the analytical system described in the analytical section. If very crude, the fractions were injected again using the isocratic method and if not too crude the fractions were injected again using the gradient method. The purity of the fraction of interest was determined using the analytical system and normally the fraction could be obtained running the isocratic method 2-5 times followed by running the gradient method 2-3 times.

The identity and purity of the isolated alkaloids were verified by HPLC-DAD-MS. The structure of the novel alkaloid Ribetril A was elucidated using 2D 1H NMR and 13C NMR in addition to HPLC-DAD-MS.

Ribetril A

HPLC-DAD-MS performed with an Agilent 1100 system (see analytical section below for details) generated an expected UV-spectrum similar to the primary chromophore (E)-3-(3,4-dihydroxyphenyl)acrylic acid and the expected primary MS-signals (ESI positive-ion mode) m/z 438 [M+H]+ and m/z 276.

For NMR analysis Ribetril A was dissolved in 40 μL methanol-d4 and transferred to 1.7 mm o.d. NMR-tubes. NMR spectra were acquired at 300 K on a 600 MHz Bruker Avance III spectrometer equipped with a cryogenically cooled inverse 1.7 mm probe head. Proton spectra were acquired using a spectral width of 12 kHz, collecting 65 536 ($2^{16}$) time domain data points. The number of added transients was adjusted to give adequate signal-to-noise ratios, typically 512-1024 scans. The water signal was suppressed by presaturation during the relaxation delay (4.0 sec.) using composite pulses [Bax 1985, Magn Reson; 65: 142-145] calibrated to cover 25 Hz. Homonuclear two-dimensional experiments were performed using the same spectral width and carrier frequency as the one-dimensional experiments (collecting 2048 time domain data points), using water signal suppression by excitation sculpting [Hwang 1995, J Magn Reson, Series A; 112:275-279]. Double quantum filtered 1H-1H COSY was acquired with 512 increments, each a sum of 32 scans, with purge pulses before the relaxation delay (1.0 sec.). Phase sensitive NOESY were acquired with 32 scans and 256 increments, mixing time 60 msec., and relaxation delay 2.0 sec.

1H-13C correlated HSQC ([Boyer 2003, J Magn Reson; 165:253-259] and HMBC [Cicero 2001, J Magn Reson; 148: 209-213] experiments were performed using the gradient selected echo-anti echo acquisition schemes, with the same carrier frequency and spectral width as the one-dimensional 1H-experiments. The number of time domain data points was 2048 and the relaxation delays 1.0 sec. Multiplicity-edited HSQC optimized for 1JH, C of 145 Hz, with adiabatic shaped pulses for all 13C inversion pulses, was acquired with 16 scans and 256 increments covering 26 kHz in the indirect dimension. HMBC optimized for 1H-13C couplings of 8 Hz (mixing time 62.5 ms), with a two-fold low-pass filter with the nodes at 125 and 165 Hz, were acquired with 64 scans and 128 increments covering 128 kHz.

Raw time domain data were typically zero-filled or linearly predicted to twice the size before applying suitable window functions (exponential multiplication or squared sine functions) and Fourier transformed to obtain spectra. The methanol-d4 residual solvent signals at 3.31 ppm (1H) and 49.15 ppm (13C) were used to calibrate the frequency axes.

Figure 2:
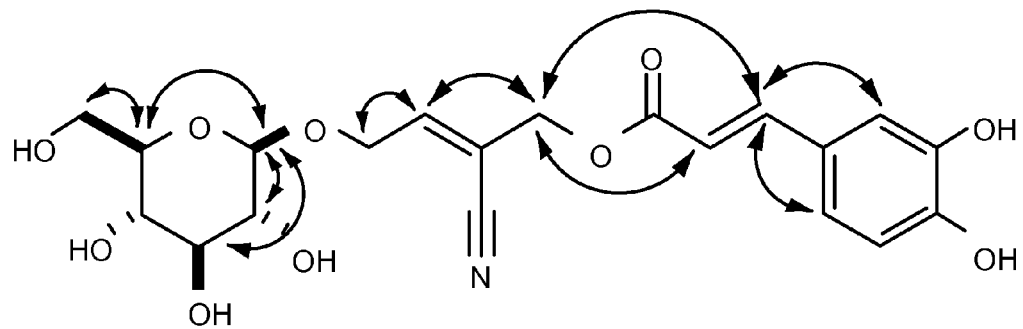
FIG. 2: TOP: Selected NOE correlations (double headed arrows). Bottom: Selected HMBC correlations (arrow pointing from H to C).
Figure 2:
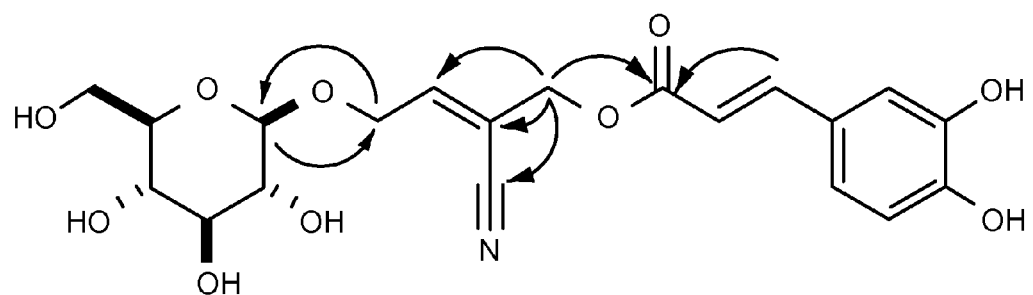

The structure of Ribetril A was further elucidated as follows. Ribetril A was identified as a (E)-3-(3,4-dihydroxyphenyl)acrylic acid analogue of (E)-2-(hydroxymethyl)-4-(((2R, 3R,4S,5S,6R)-3,4,5-trihydroxy-6-(hydroxymethyl) tetrahydro-2H-pyran-2-yl)oxy)but-2-enenitrile. The structure with the numbering used for structure elucidation is shown in FIG. 1; and the 1H NMR spectrum with annotation of all resonances is shown in FIG. 2. Thus, based on the resonance of the anomeric H-1' (δ 4.34, d, J=7.8 Hz), the β-D-glucopyranoside unit was identified as an isolated spin system (H1'-H2'-H3'-H4'-H5'-H6'A/H6'B) in the COSY spectrum. At the same time, the β-configuration of the D-glucoside was established based on the axial-axial coupling (JH1', H2'=7.8 Hz) between H1' and H2'; and thus equatorial position of the glycosidic bond. The diastereotopic proton pair H1A (δ 4.54, dd, JH1A, H2=6.5 Hz) and H1B (δ 4.65, dd, JH1B, H2=6.0 Hz) was identified based on their correlation to C1 (δ 67.98) in the HSQC spectrum and both showed a COSY cross peak to H2 (δ 6.85, t, JH1A, H2≈JH1B, H2≈6.3 Hz). The remaining resonances of the central (E)-4-hydroxy-2-(hydroxymethyl)but-2-enenitrile unit was identified based on HMBC correlations from H4 (δ 4.82, overlapping with water resonance) to C2 (δ 148.8), C3 (δ 112.6) and C5 (δ 115.7); as well as a strong cross peak in the NOESY spectrum to establish the (E) configuration of the double bond (see FIG. 3). The position of the (E)-3-(3,4-dihydroxyphenyl)acrylic acid unit at position 4 was identified based on cross peaks (weak) between H4 and H2" as well as between H4 and H3". In addition, a correlation from H4 to C1" ((E)-3-(3,4-dihydroxyphenyl)acrylic acid 168.0; the carbonyl carbon) was observed in the HMBC spectrum.

FIG. 1 shows the structure of Ribetril A with the numbering used for assignment of 1H and 13C resonances. Note that the numbering of Ribetril A differs from the strict IUPAC numbering.

FIG. 2: TOP: Selected NOE correlations (double headed arrows). Bottom: Selected HMBC correlations (arrow pointing from H to C).

Figure 3:
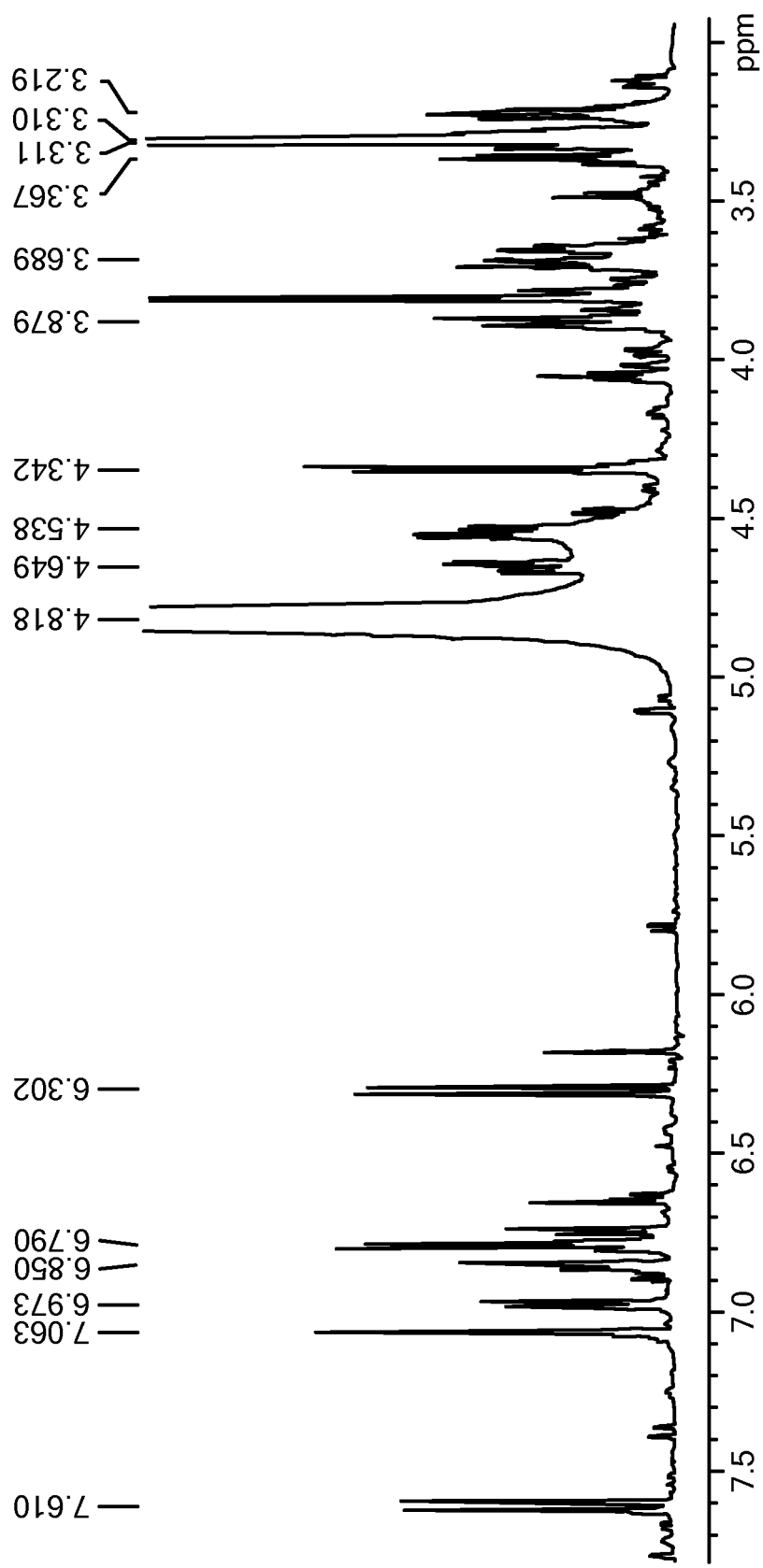
FIG. 3 shows the 1H NMR spectrum with annotation of all 1H resonances of Ribetril A.

FIG. 3 shows the 1H NMR spectrum with annotation of all 1H resonances of Ribetril A.

Assignment of 1H and 13C resonances are given below.

1H NMR (600 MHz, CD3OD), δ 3.22 [dd, 1H, J=7.9, 8.8 Hz, H—C(4')], 3.30 [m, 1H, H—C(5')], 3.31 [m, 1H, H—C(4')], 3.37 [t, 1H, J=8.6 Hz, H—C(3')], 3.69 [dd, 1H, J=5.1, 12.1 Hz, H—C(6a')], 3.88 [dd, 1H, J=2.0, 12.0 Hz, H—C(6b')], 4.34 [d, 1H, J=7.8 Hz, H—C(1')], 4.54 [dd, 1H, J=6.5, 14.6 Hz, H—C(1a)], 4.65 [dd, 1H, J=6.0, 14.6 Hz, H—C(1b)], 4.82 [m, 2H, H—C(4)], 6.30 [d, 1H, J=15.9 Hz, H—C(2")], 6.79 [d, 1H, J=8.2 Hz, H—C(8")], 6.85 [t, 1H, J=6.3 Hz, H—C(2)], 6.97 [dd, 1H, J=1.9, 8.2 Hz, H—C(9")], 7.06 [d, 1H, J=1.9 Hz, H—C(5")], 7.61 [d, 1H, J=15.9 Hz, H—C(3")]; 13C NMR (150 MHz, CD3OD), δ 62.4 [C(6')], 64.1 [C(4)], 68.0 [C(1)], 71.2 [C(4')], 74.7 [C(2')], 77.7 [C(3')], 77.8 [C(5')], 104.0 [C(1')], 112.6 [C(3)], 113.7 [C(2")], 115.0 [C(5")], 115.7 [C(5)], 116.3 [C(8")], 123.0 [C(9")], 127.1 [C(4")], 146.3 [C(6")], 147.8 [C(3"), 148.2 [C(7"), 148.8 [C(2), 168.0 [C(1")].

Ribetril B

HPLC-PDA-MS performed with an Agilent 1100 system (see analytical section below for details) generated an expected UV-spectrum similar to the primary chromophore (E)-3-(4-hydroxy-3-methoxyphenyl)acrylic acid and the expected primary MS-signal (ESI positive-ion mode) m/z 452 [M+H]+ and m/z 290.

Ribetril C

HPLC-PDA-MS performed with an Agilent 1100 system (see analytical section below for details) generated an expected UV-spectrum similar to the primary chromophore (E)-3-(4-hydroxyphenyl)acrylic acid and the expected primary MS-signal (ESI positive-ion mode) m/z 422 [M+H]+ and m/z 290.

Ribetril D

HPLC-PDA-MS performed with an Agilent 1100 system (see analytical section below for details) generated an expected UV-spectrum similar to the primary chromophore 4-hydroxy-3-methoxybenzoic acid and the expected primary MS-signal (ESI positive-ion mode) m/z 426 [M+H]+ and m/z 264.

Ribetril E

HPLC-PDA-MS performed with an Agilent 1100 system (see analytical section below for details) generated an expected UV-spectrum similar to the primary chromophore 4-hydroxybenzoic acid acid and the expected primary MS-signal (ESI positive-ion mode) m/z 396 [M+H]+ and m/z 234.

Glucoindol A

HPLC-PDA-MS performed with an Agilent 1100 system (see analytical section below for details) generated an expected UV-spectrum similar to the primary chromophore 2-(1H-indol-3-yl)acetic acid and the expected primary MS-signal (ESI positive-ion mode) m/z 338 [M+H]+ and m/z 320.

Glucoindol B

HPLC-PDA-MS performed with an Agilent 1100 system (see analytical section below for details) generated an expected UV-spectrum similar to the primary chromophore methyl 2-(1H-indol-3-yl)acetate and the expected primary MS-signal (ESI positive-ion mode) m/z 352 [M+H]+ and m/z 334.

Establishment of the Mass Fraction of Ribetrils and Glucoindols in Ribes.

Ribes juice from commercial sources produced from-Ribes rubrum and Rubes nigrum cultivars was used to establish the naturally occurring level of the alkaloids of the invention in the berries. This is a sound starting material for the determination of the naturally occurring level of alkaloids since all the alkaloids of the invention have a high solubility in water and therefore will be present in levels in the juice that are representative for the amount in the berry.

Applying the quantitative analysis described in the experimental section below, injecting the highest possible amount of dry matter from the juice gave the following mass fraction:

Ribetril A: 0-0.00008%
Total Ribetrils: 0.00005-0.00015%
Total Glucoindols: 0.00032-0.00069% (On this basis a total levels of Glucoindols above 0.0008% is defined as an increased mass fraction as compared to- Ribes.)

Conclusion:

On this basis a mass fraction of Ribetril A above 0.0001% is defined as an increased mass fraction as compared to- Ribes.

On this basis a total levels of Ribetrils above 0.0002% is defined as an increased mass fraction as compared to- Ribes.

On this basis a total levels of Glucoindols above 0.0008% is defined as an increased mass fraction as compared to- Ribes.

Preparation of an Extract, Juice or Concentrate of Ribes Comprising the Alkaloid Fractions of the Invention For the purpose of preparing a variety of alkaloid compositions of the invention from Ribes, the following general steps were applied:

1. Preparing a suspension of the ground berries and/or leaves.

500 g of berries of industrial "juice quality", meaning berries with stalks and to some extent leaves from the Ribes in question were grinded and homogenized. In the last step of homogenization an IKA® T25 Digital Ultraturrax running at 24000 rpm was applied for 30 minutes and up to 500 ml of demineralized water was added to aid the homogenization depending on the water content of the Ribes sample.

To inrease the extractability of the alkaloid fractions of the invention, the suspension in some cases was subjected to enzyme treatment with one of the following cocktails of enzymes provided by Novozymes A/S, Denmark:

a. 0.1-0.5 g Viscozyme L, which is a multienzyme complex with a strong pectolytic activity and a wide range of carbohydrases including arabinase, cellulase, beta-glucanase, hemicellulase and xylanase.

The enzyme treatment was carried out for 4 hours at 50° C. after adjustment of the pH to 4.5 with 0.1 M NaOH.

b. 0.1-0.5 g Pectinex® BE XXL, which is an enzyme with strong pectolytic activity.

2. Optionally extracting the ground berries and/or leaves with an extraction agent.

This step was skipped in the case where a juice product or concentrate was envisaged. This step was carried out by the addition of 500-1500 ml of an extraction agent selected from:

Demineralized water
Methanol

Ethanol
Acetone
1-propanol
2-propanol
Ethyl acetate

All extractions were carried out at 25-70° C. for 1-4 hours.

Subsequent extraction with the same solvent gave higher yields of the alkaloid fractions. It was a general observation that a full extraction of all alkaloids of the invention could be obtained with the different solvents only depending on the number of repeated extractions necessary and the extraction conditions with regards to temperature and time.

The primary difference between the obtained extracts after full extraction of the alkaloids with the different solvents was the co-extraction of other classes of compounds from the different *Ribes*.

Based on the experience from the extraction program carried out, it was concluded that a full extraction of the alkaloids of the invention could likely be obtained with various mixtures of the mentioned solvents and with other solvents, even with relatively varying polarity. As appreciated by a person skilled in the art similar results can be obtained with diverse extraction techniques including maceration, percolation, Soxhlet extraction, super critical extraction, etc. Before further processing the crude extract was subjected to a final step of removing particles of extracted plant material by filtration on a Büchner funnel with vacuum suction.

3. Optionally removing the extraction agent.

This step was carried out on a rotary evaporator (Büchi Rotavapor R-210 equipped with vacuum controller V-850) under vacuum at 50° C. For the purpose of removing residues of organic solvent a step of stripping with up to 500 ml of ethanol was applied.

As appreciated by a person skilled in the art a similar result may be obtained with other drying techniques, such as freeze drying, fluid bed drying, etc.

In some cases this step was superfluous simply because the crude extract could be taken directly to the next step. In the case of a juice taken directly from step 1, this step could be used to make a juice concentrate optionally for further processing.

4. Optionally further concentration of the alkaloid fraction.

Obviously this step was oblivious if the desired concentration of the alkaloids of the invention had been obtained with the preceding processing steps.

This step was carried out using various techniques independently or in combination.

a. Centrifugation

After cooling of the crude extract or resuspending of the dried crude extract in water, a step of centrifugation was in some cases used to remove particulate matter, e.g. precipitated lipids, proteins or polysaccharides.

b. Filtration

In some cases a step of ultrafiltration was applied to move residual macromolecules in solution, which could significantly increase the concentration of the alkaloid fraction of the invention as compared to the concentration in the crude extract.

This step was carried out on a Minimate™ Tangential Flow Filtration System from Pall Corporation, USA. The system was equipped with a polyethersulfone ultrafiltration membrane (Omega™ TFF capsule) with a molecular cut-off of 3000, 10000, 30000 or 100000 Dalton. As appreciated by the person skilled in the art a similar result could be obtained with other filter materials and molecular cut-offs. Furthermore, a step of nanofiltration could advantageously be applied to remove monosaccharides, inorganic ions, and small carboxylic acids.

c. Liquid-Liquid Extraction

In some cases a step of liquid-liquid extraction was applied and carried out in a traditional separating funnel. An aqueous solution of the *Ribes* extract was extracted with a water immiscible organic solvent in which the alkaloids of the invention were soluble. Successful liquid-liquid extractions were carried out with ethyl acetate or 1-butanol.

As appreciated by the person skilled in the art a useful concentration of the alkaloids of the invention may be obtained with various other solvents or mixtures of solvents.

d. Solid-Liquid Extraction

In some cases a step of solid-liquid extraction was applied, where the dried crude extract was redissolved in a solvent preferentially dissolving the alkaloids of the invention. Depending on the crude extract, solid-liquid extraction was successfully carried out with 2-propanol, 1-butanol or ethyl acetate.

As appreciated by the person skilled in the art a useful concentration of the alkaloids of the invention may be obtained with other solvents or mixtures of solvents.

e. Chromatography

To obtain the purified *Ribes* alkaloid fractions of the invention a step of chromatography was applied in some cases.

This step was carried out with solid phase extraction column, Supelco Discovery® DSC-18, 10 g, 60 ml tubes mounted on a Supelco Visiprep 24 TM DL vacuum system. The following standard procedure was applied:

The column was conditioned with 60 ml methanol (MeOH) and equilibrated with 60 ml 25% MeOH in water (vol/vol).

Crude or pre-purified *Ribes* extract corresponding to 1000 mg of dry matter was applied to the column in a volume of 10-25 ml water (depending on the solubility).

The column was eluted with 100 ml water, which was collected as a separate fraction.

The column was eluted with 100 ml 10% MeOH in water (vol/vol), which was collected as a separate fraction.

The column was eluted with 100 ml 20% MeOH in water (vol/vol), which was collected as a separate fraction.

The column was eluted with 100 ml 30% MeOH in water (vol/vol), which was collected as a separate fraction.

The column was eluted with 100 ml 40% MeOH in water (vol/vol), which was collected as a separate fraction.

The column was eluted with 100 ml 50% MeOH in water (vol/vol), which was collected as a separate fraction.

The column was eluted with 100 ml 60% MeOH in water (vol/vol), which was collected as a separate fraction.

The column was eluted with 100 ml 70% MeOH in water (vol/vol), which was collected as a separate fraction.

The column was eluted with 100 ml 80% MeOH in water (vol/vol), which was collected as a separate fraction.

In this manner further concentrated alkaloid fractions according to the invention were collected.

It is appreciated by a person skilled in the art that various column materials and principles of chromatography, such as other types of reversed phase chromatography, normal phase chromatography, ion-exchange chromatography, etc. may be applied to obtain similar results.

f. Drying

Depending on the preceding processing, a final step of drying was optionally applied.

In most cases the drying was carried out on a rotary evaporator (Büchi Rotavapor R-210 equipped with vacuum controller V-850) under vacuum at 50° C. As appreciated by a person skilled in the art a similar result may be obtained with other drying techniques, such as freeze drying, fluid bed drying, spray drying, etc.

Scale Up for Preparative Purposes

In some cases the experimental manufacturing process described above was scaled up to pilot-plant production scale to obtain sufficient quantities of the extract, juice or concentrate of *Ribes* comprising the alkaloid fractions of the invention, e.g. for clinical trials employing the nutritive products of the invention.

Analytical Section

All purified alkaloids according to the invention and extracts, juices or concentrates of *Ribes* comprising them were characterized using an Agilent 1100 HPLC-DAD-MS system consisting of a binary pump, an autosampler, a column oven, a diode array detector (DAD) and an MS quadropole detector equipped with an electrospray ionization source. All data were recorded using the Agilent Chemstation software. The separation of the compounds was achieved on a Poroshell 120 SB-C18 column (3×150 mm, 2.7 µm) from Agilent Technologies. All solvents used were MS quality from commercial suppliers. The mobile phase consisted of water with 0.5% formic acid and acetonitrile with 0.5% formic acid using a gradient from 2-98% v/v acetonitrile with 0.5% formic acid (0-110 min) and 98-2% v/v acetonitrile with 0.5% formic acid (110-120 min) and a flow-rate of 0.5 ml/min. The UV data were acquired as full scan UV spectra at 200-700 nm. The MS data were acquired as full scan mass spectra at m/z 100-1000 (ESI positive-ion mode).

Results

The analysis confirmed the purity of the isolated alkaloids used for bioassays as mentioned above.

The following extracts juices and concentrates of the invention were analyzed:

| *Ribes* alkaloid product number: | RAP1 |
|---|---|
| Starting material: | *Ribes rubrum*- Cultivar: Rondum |
| Extraction agent: | None - juice produced and extraction aided by enzymatic treatment. |
| Method of concentrating the alkaloid fraction: | Centrifugation and filtration followed by drying. |
| Concentration in final product (w/w): | Ribetril A: 0.00101% |
| | Ribetril E: 0.00304% |
| | Total Ribetrils: 0.00405% |
| | Glucoindol A: 0.00634% |
| | Total Glucoindols: 0.00634% |

| *Ribes* alkaloid product number: | RAP2 |
|---|---|
| Starting material: | *Ribes rubrum*- Cultivar: Rovada |
| Extraction agent: | None - juice produced and water added for extended extraction aided by enzymatic treatment. |
| Method of concentrating the alkaloid fraction: | Centrifugation and filtration followed by drying. |
| Concentration in final product (w/w): | Ribetril A: 0.00044% |
| | Ribetril D: 0.00036% |
| | Ribetril E: 0.00330% |
| | Total Ribetrils: 0.00410% |
| | Glucoindol A: 0.02749% |
| | Glucoindol B: 0.00409% |

| *Ribes* alkaloid product number: | RAP3 |
|---|---|
| Starting material: | *Ribes rubrum* - Cultivar: Rondum |
| Extraction agent: | Juice produced and extraction aided by enzymatic treatment. This was followed by extraction with 2-propanol. |
| Method of concentrating the alkaloid fraction: | Centrifugation and filtration followed by drying. |
| Concentration in final product (w/w): | Ribetril A: 0.00072% |
| | Ribetril D: 0.00204% |
| | Ribetril E: 0.01348% |
| | Total Ribetrils: 0.16240% |
| | Glucoindol A: 0.03011% |
| | Total Glucoindols: 0.03011% |

| *Ribes* alkaloid product number: | RAP4 |
|---|---|
| Starting material: | *Ribes rubrum* - Cultivar: Rovada |
| Extraction agent: | 2-propanol |
| Method of concentrating the alkaloid fraction: | Centrifugation and filtration followed by drying. |
| Concentration in final product (w/w): | Ribetril A: 0.00559% |
| | Ribetril D: 0.01267% |
| | Ribetril E: 0.00632% |
| | Total Ribetrils: 0.02458% |
| | Glucoindol A: 0.01200% |
| | Total Glucoindols: 0.01200% |

| *Ribes* alkaloid product number: | RAP5 |
|---|---|
| Starting material: | *Ribes rubrum* - Cultivar: Redpoll |
| Extraction agent: | 2-propanol |
| Method of concentrating the alkaloid fraction: | Centrifugation and filtration followed by drying. |
| Concentration in final product (w/w): | Ribetril A: 0.00656% |
| | Ribetril B: 0.00532% |
| | Ribatril C: 0.01642% |
| | Ribetril D: 0.03511% |
| | Ribetril E: 0.04983% |
| | Total Ribetrils: 0.11324% |
| | Glucoindol A: 0.12078% |
| | Total Glucoindols: 0.12078% |

| *Ribes* alkaloid product number: | RAP6 |
|---|---|
| Starting material: | *Ribes rubrum* - Cultivar: White dutch |
| Extraction agent: | 2-propanol |
| Method of concentrating the alkaloid fraction: | Centrifugation and filtration followed by drying. |
| Concentration in final product (w/w): | Ribetril A: 0.00105% |
| | Ribetril D: 0.00544% |
| | Ribetril E: 0.01714% |
| | Total Ribetrils: 0.02363% |
| | Glucoindol A: 0.12941% |
| | Total Glucoindols: 0.12941% |

| | | | |
|---|---|---|---|
| *Ribes* alkaloid product number: | RAP7 | *Ribes* alkaloid product number: | RAP12 |
| Starting material: | *Ribes rubrum* - Cultivar: Rovada | Starting material: | *Ribes nigrum* - Cultivar: Ben Cannon |
| Extraction agent: | 2-propanol | Extraction agent: | Extraction with ethanol followed by drying, dissolution in water and C18 solid phase extract where the 50% methanol fraction was collected. |
| Method of concentrating the alkaloid fraction: | Centrifugation and filtration followed by drying. | Method of concentrating the alkaloid fraction: | Centrifugation and filtration followed by drying. |
| Concentration in final product (w/w): | Ribetril A: 0.00089%<br>Ribetril D: 0.00191%<br>Ribetril E: 0.00735%<br>Total Ribetrils: 0.01015%<br>Glucoindol A: 0.00762%<br>Glucoindol B: 0.00379%<br>Total Glucoindols: 0.01141% | Concentration in final product (w/w): | Ribetril A: 0.27793%<br>Ribetril B: 0.69995%<br>Ribetril C: 3.02783%<br>Ribetril E: 1.75933%<br>Total Ribetrils: 5.76504% |

| | | | |
|---|---|---|---|
| *Ribes* alkaloid product number: | RAP8 | *Ribes* alkaloid product number: | RAP13 |
| Starting material: | *Ribes rubrum* - Cultivar: Rosetta | Starting material: | *Ribes rubrum* - Cultivar: Rovada |
| Extraction agent: | 2-propanol | Extraction agent: | Juice produced and extraction aided by enzymatic treatment. The juice was concentrated by vacuum drying and subjected to repeated liquid-liquid extraction with ethyl acetate. |
| Method of concentrating the alkaloid fraction: | Centrifugation and filtration followed by drying. | Method of concentrating the alkaloid fraction: | Centrifugation and filtration followed by drying. |
| Concentration in final product (w/w): | Ribetril A: 0.00024%<br>Ribetril E: 0.00234%<br>Total Ribetrils: 0.00258%<br>Glucoindol A: 0.00230%<br>Total Glucoindols: 0.00230% | Concentration in final product (w/w): | Ribetril A: 0.00342%<br>Ribetril B: 0.00251%<br>Ribetril D: 0.00562%<br>Ribetril E: 0.01330%<br>Total Ribetrils: 0.02486%<br>Glucoindol A: 0.06111%<br>Glucoindol B: 0.01800%<br>Total Glucoindols: 0.07911% |

| | | | |
|---|---|---|---|
| *Ribes* alkaloid product number: | RAP9 | *Ribes* alkaloid product number: | RAP14 |
| Starting material: | *Ribes nigrum* - Cultivar: Ben alder | Starting material: | *Ribes nigrum* - Cultivar: Ben alder |
| Extraction agent: | None - juice produced and extraction aided by enzymatic treatment. | Extraction agent: | Juice produced and extraction aided by enzymatic treatment. The juice was concentrated by vacuum drying and subjected to repeated liquid-liquid extraction with ethyl acetate. |
| Method of concentrating the alkaloid fraction: | Centrifugation and filtration followed by drying. | Method of concentrating the alkaloid fraction: | Centrifugation and filtration followed by drying. |
| Concentration in final product (w/w): | Ribetril A: 0.00063%<br>Ribetril C: 0.00345%<br>Ribetril E: 0.00123%<br>Total Ribetrils: 0.00531% | Concentration in final product (w/w): | Ribetril A: 0.01440%<br>Ribetril B: 0.00088%<br>Ribetril C: 0.00499%<br>Ribetril D: 0.00682%<br>Ribetril E: 0.02192%<br>Total Ribetrils: 0.04901%<br>Glucoindol A: 0.01740%<br>Total Glucoindols: 0.01740% |

| | | | |
|---|---|---|---|
| *Ribes* alkaloid product number: | RAP10 | *Ribes* alkaloid product number: | RAP15 |
| Starting material: | *Ribes nigrum* - Cultivar: Ben Lomond | Starting material: | *Ribes rubrum* - Cultivar: Rondum |
| Extraction agent: | Extraction with ethanol followed by drying and solid-liquid extraction with ethyl acetate. | Extraction agent: | Juice produced and extraction aided by enzymatic treatment. The juice was concentrated by vacuum drying and subjected to repeated liquid-liquid extraction with ethyl acetate. |
| Method of concentrating the alkaloid fraction: | Centrifugation and filtration followed by drying. | Method of concentrating the alkaloid fraction: | Centrifugation and filtration followed by drying. |
| Concentration in final product (w/w): | Ribetril A: 0.05637%<br>Ribetril B: 0.24760%<br>Ribetril C: 0.72412%<br>Ribetril E: 0.65570%<br>Total Ribetrils: 1.68379% | Concentration in final product (w/w): | Ribetril A: 0.01765%<br>Ribetril B: 0.00251%<br>Ribetril C: 0.00542%<br>Ribetril D: 0.01827%<br>Ribetril E: 0.1725%<br>Total Ribetrils: 0.21635%<br>Glucoindol A: 0.03448%<br>Glucoindol B: 0.01551%<br>Total Glucoindols: 0.04999% |

| | |
|---|---|
| *Ribes* alkaloid product number: | RAP11 |
| Starting material: | *Ribes nigrum* - Cultivar: : Ben Tron |
| Extraction agent: | Extraction with ethanol followed by drying, dissolution in water and liquid/liquid extraction with ethyl acetate. |
| Method of concentrating the alkaloid fraction: | Centrifugation and filtration followed by drying. |
| Concentration in final product (w/w): | Ribetril A: 0.26511%<br>Ribetril B: 0.61637%<br>Ribetril C: 3.29783%<br>Ribetril E: 0.43318%<br>Total Ribetrils: 4.61249% |

| Ribes alkaloid product number: | RAP16 |
|---|---|
| Starting material: | *Ribes rubrum* - Cultivar: Rovada/Rondum |
| Extraction agent: | None - juice produced, temperature increased and water added for extended extraction aided by enzymatic treatment. |
| Method of concentrating the alkaloid fraction: | Centrifugation and filtration followed by drying. |
| Concentration in final product (w/w): | Ribetril A: 0.00015% |
| | Ribetril B: 0.00009% |
| | Ribetril D: 0.00035% |
| | Ribetril E: 0.00032% |
| | Total Ribetrils: 0.00091% |
| | Glucoindol A: 0.00447% |
| | Glucoindol B: 0.00038% |
| | Total Glucoindols: 0.00485% |

| Ribes alkaloid product number: | RAP17 |
|---|---|
| Starting material: | *Ribes nigrum*- Cultivar: Ben Lomond |
| Extraction agent: | None - juice produced, temperature increased and water added for extended extraction aided by enzymatic treatment. |
| Method of concentrating the alkaloid fraction: | Centrifugation and filtration followed by drying. |
| Concentration in final product (w/w): | Ribetril A: 0.00039% |
| | Ribetril B: 0.00047% |
| | Ribetril D: 0.00040% |
| | Ribetril E: 0.00016% |
| | Total Ribetrils: 0.00142% |
| | Glucoindol A: 0.00105% |
| | Total Glucoindols: 0.00105% |

| Ribes alkaloid product number: | RAP18 |
|---|---|
| Starting material: | Mixture of RAP16 AND RAP17 50:50 (by weight) |
| Extraction agent: | N/A |
| Method of concentrating the alkaloid fraction: | N/A |
| Concentration in final product (w/w): | N/A |

| Ribes alkaloid product number: | RAP19 |
|---|---|
| Starting material: | *Ribes nigrum* - Cultivars: Mixture of Ben Tron, Ben Cannon, Ben Lomond, Ben Alder and Ben Tirran. The pomace was dried before further processing. |
| Extraction agent: | Mixture of ethanol 50-70 % and water (by volume). |
| Method of concentrating the alkaloid fraction: | Centrifugation and filtration followed by drying. |
| Concentration in final product (w/w): | Ribetril A: 0.00247% |
| | Ribetril B: 0.00024% |
| | Ribetril C: 0.00090% |
| | Ribetril D: 0.00118% |
| | Ribetril E: 0.00370% |
| | Total Ribetrils: 0.00849% |
| | Glucoindol A: 0.00849% |
| | Total Glucoindols: 0.00849% |

| Ribes alkaloid product number: | RAP20 |
|---|---|
| Starting material: | *Ribes nigrum* - Cultivars: Mixture of Ben Tron, Ben Cannon, Ben Lomond, Ben Alder and Ben Tirran. The pomace was dried before further processing. |
| Extraction agent: | Mixture of methanol 50-70% and water (by volume). |
| Method of concentrating the alkaloid fraction: | Centrifugation and filtration followed by drying. |
| Concentration in final product (w/w): | Ribetril A: 0.00232% |
| | Ribetril B: 0.00024% |
| | Ribetril C: 0.00086% |
| | Ribetril D: 0.00112% |
| | Ribetril E: 0.00348% |
| | Total Ribetrils: 0.00802% |
| | Glucoindol A: 0.00271% |
| | Total Glucoindols: 0.00271% |

| Ribes alkaloid product number: | RAP21 |
|---|---|
| Starting material: | *Ribes nigrum* - Cultivars: Mixture of Ben Tron, Ben Cannon, Ben Lomond, Ben Alder and Ben Tirran. The pomace was dried before further processing. |
| Extraction agent: | Mixture of acetone 50-70 % and water (by volume). |
| Method of concentrating the alkaloid fraction: | Centrifugation and filtration followed by drying. |
| Concentration in final product (w/w): | Ribetril A: 0.00216% |
| | Ribetril B: 0.00022% |
| | Ribetril C: 0.00080% |
| | Ribetril D: 0.00105% |
| | Ribetril E: 0.00323% |
| | Total Ribetrils: 0.00746% |
| | Glucoindol A: 0.00259% |
| | Total Glucoindols: 0.00259% |

| Ribes alkaloid product number: | RAP22 |
|---|---|
| Starting material: | *Ribes rubrum* - Cultivars: Mixture of Rondum, Rovada and Rosetta. The pomace was dried before further processing. |
| Extraction agent: | 2-propanol |
| Method of concentrating the alkaloid fraction: | Centrifugation and filtration followed by drying. |
| Concentration in final product (w/w): | Ribetril A: 0.00075% |
| | Ribetril B: 0.00060% |
| | Ribetril D: 0.00118% |
| | Ribetril E: 0.00271% |
| | Total Ribetrils: 0.00524% |
| | Glucoindol A: 0.01229% |
| | Glucoindol B: 0.00365% |
| | Total Glucoindols: 0.01594% |

Example 2

Objective

The objective of this study was to test the viability of different proportions of mixtures of concentrates/extracts of *Ribes rubrum* and *Ribes nigrum* by simply testing the stability of such mixtures after 3 months exposure to slightly elevated temperature (40 degrees C.).

Method

RAP16 and RAP17 were prepared in example 1.

10 g of mixtures of RAP16 and RAP17 were prepared in the proportions shown in the table below:

| RAP16% (by weight) | RAP17% (by weight) |
|---|---|
| 5 | 95 |
| 10 | 90 |
| 15 | 85 |
| 20 | 80 |
| 25 | 75 |
| 30 | 70 |
| 35 | 65 |
| 40 | 60 |
| 45 | 55 |
| 50 | 50 |
| 55 | 45 |
| 60 | 40 |
| 65 | 35 |
| 70 | 30 |
| 75 | 25 |
| 80 | 20 |
| 85 | 15 |
| 90 | 10 |
| 95 | 5 |

All samples were stored in sterile glass containers for 90 days at elevated temperature (40 degrees C.).

A chemical profile of all samples was established before and after 90 days storage employing the HPLC-DAD-MS method described in Example 1.

Results

The chemical profiles of each mixture of RAP16 and RAP17 before and after storage at elevated temperature were compared. No differences were observed.

Conclusion

All tested mixtures of RAP16 and RAP17 were found to be stable, thus the differences in chemical profile of *Ribes rubrum* and *Ribes nigrum* had no negative influence on the potential to combine them with regard to stability.

Example 3

Objective

The objective of this study was the investigation of the in vitro inhibitory effect of isolated alkaloids of the invention on IkappaB kinase β (IKK-β).

Background

IKK-β phosphorylates the inhibitory IκB protein associated with NF-κB. Phosphorylation results in the dissociation of IκB from NF-κB, allowing NF-κB to migrate into the cell nucleus where it can activate the transcription of at least 150 genes. The Z9-LYTE™ Kinase Assay Kit—Ser/Thr 5 Peptide is designed to screen for potential IKK-β inhibitory effect using fluorescence resonance energy transfer (FRET) between coumarin and fluorescein for detection by a fluorometer.

Method

The assay was performed according to Z9-LYTE™ KINASE ASSAY KIT—SER/THR 5 PEPTIDE protocol provided by Invitrogen [Invitrogen, Z'-LYTE™ Kinase Assay Kit—Ser/Thr 5 Peptide Protocol, O-062187-r1 US 0405]. Based on the IKK-β certificate of the kit, a kinase concentration of 500 ng/ml was chosen. Km for ATP 9.4 µM was chosen according to an optimization for the LanthaScreen™ kinase assay [http://tools.invitrogen.com/content/sfs/manuals/IKBKB_%28IKK_beta%29_LanthaScreen_Activity.pdf].

Instrument Set-Up

A fluorescence plate reader (Appliskan, Thermo Scientific) was used to detect fluorescence emission signals according to the following parameters:

| Parameter | Specifikation |
|---|---|
| Excitation | 400 nm filter (Bandwith 30 nm) |
| Emission | 520 nm (Bandwith 25 nm) |
| Emission | 445 nm (Bandwith 10 nm) |
| Delay time | 100 µs |
| Integration time | 200 µs |
| Measurement time | 10000 ms |

Test Compounds

Selected alkaloids of the invention prepared in example 1 were tested in 5 times dilutions to establish the 50% inhibitory concentration (IC-50).

Results

| Inhibitory effect on IKK-β | |
|---|---|
| Alkaloid | IC-50 |
| Ribetril A | 0.13 µM |
| Ribetril B | 6.3 µM |
| Ribetril C | 15.3 µM |
| Ribetril D | 0.037 µM |
| Ribetril E | 1.9 µM |

Conclusion

As compared to the two most closely related alkaloids with the same phenyl-acrylic acid backbone Ribetril A was a significantly more potent inhibitor of IKK-β. Thus, Ribetril A displayed a 48 and 118 times lower IC-50 as compared to Ribetril B and Ribetril C, respectively.

In conclusion all of the tested alkaloids of the invention displayed a dose-dependent and significant inhibition of IKK-β at physiologically relevant concentrations.

REFERENCES

1. Rodems 2002, ASSAY Drug Devel Technol; 1:9-19.
2. Kleman-Leyer 2003, Drug Disc Devel; 6:81-2.
3. Zhang 1999, J Biomol Screen; 4:67-73.
4. Davies 2000, Biochem J; 351:95-105.
5. Chijiwa 1990, J Biol Chem; 265:5267-72.

Example 4

Objective

The objective of this study was the investigation of the in vitro inhibitory effect of alkaloids of the invention on phosphodiesterase 4 (PDE4).

Background

PDE4 hydrolyzes cyclic adenosine monophosphate (cAMP) to inactive adenosine monophosphate (AMP). Inhibition of PDE4 blocks hydrolysis of cAMP, thereby increasing levels of cAMP. The PDE4A1A Assay Kit is designed for identification of PDE4A1A inhibitors using fluorescence polarization. The assay is based on the binding of fluorescent AMP generated by PDE4A1A to the binding agent.

Method

The assay was performed according to the protocol of the PDE4A1A assay provided by BSP Bioscience [BSP Bioscience, Data sheet PDE4A1A Assay Kit, Catalog #60340].

Instrument Set Up

A fluorescence plate reader (Appliskan, Thermo Scientific) was used to detect fluorescence emission signals according to the following parameters:

| Parameter | Specifikation |
|---|---|
| Excitation | 485 nm filter |
| Emission | 530 nm (Bandwith 9 nm) |
| Measurement time | 500 ms |

Test Compounds

Selected alkaloids of the invention prepared in example 1 were tested in 5 times dilutions to establish the 50% inhibitory concentration (IC-50).

Results

| Inhibitory effect on PDE4 | |
|---|---|
| Alkaloid | IC-50 |
| Ribetril A | 2.95 µM |
| Ribetril B | 14.0 µM |
| Ribetril C | 59.7 µM |
| Ribetril D | 0.23 µM |
| Ribetril E | 3.5 µM |
| Glucoindol A | 86.1 µM |
| Glucoindol B | 45.6 µM |

Conclusion

As compared to the two most closely related alkaloids with the same phenyl-acrylic acid backbone Ribetril A was a significantly more potent inhibitor of PDE4. Thus, Ribetril A displayed a 5 and 20 times lower IC-50 as compared to Ribetril B and Ribetril C, respectively.

In conclusion all of the tested alkaloids of the invention displayed a significant and dose-dependent inhibition of PDE4 at physiologically relevant concentrations.

REFERENCES

Goldhoff 2008, Clin Cancer Res; 14(23):7717-25.

Example 5

Objective

The objective of this study was the investigation of the in vitro inhibitory effect of alkaloids of the invention on phosphodiesterase 5A (PDE5).

Background

PDE5 hydrolyzes cyclic guanosine monophosphate (cGMP) to inactive 5'-GMP. Inhibition of PDE5 blocks hydrolysis of cGMP, thereby increasing levels of cGMP. The PDE5A Assay Kit is designed for identification of PDE5A inhibitors using fluorescence polarization. The assay is based on the binding of a fluorescent nucleotide monophosphate generated by PDE5A to the binding agent.

Method

The assay was performed according to the protocol of the PDE5A assay provided by BSP Bioscience [BSP Bioscience, Data sheet PDE5A Assay Kit, Catalog #60350].

Instrument Set Up

A fluorescence plate reader (Appliskan, Thermo Scientific) was used to detect fluorescence emission signals according to the following parameters:

| Parameter | Specifikation |
|---|---|
| Excitation | 485 nm filter |
| Emission | 530 nm (Bandwith 9 nm) |
| Measurement time | 500 ms |

Test Compounds

Selected alkaloids of the invention prepared in example 1 were tested in 5 times dilutions to establish the 50% inhibitory concentration (IC-50).

Results

| Inhibitory effect on PDE5 | |
|---|---|
| Alkaloid | IC-50 |
| Ribetril A | 2.1 µM |
| Ribetril B | 5.4 µM |
| Ribetril C | 17.2 µM |
| Ribetril D | <0.04 µM |
| Ribetril E | 3.4 µM |

Conclusion

As compared to the two most closely related alkaloids with the same phenyl-acrylic acid backbone Ribetril A was a significantly more potent inhibitor of PDE5. Thus, Ribetril A displayed a 3 and 8 times lower IC-50 as compared to Ribetril B and Ribetril C, respectively.

In conclusion all of the tested alkaloids of the invention displayed a significant and dose-dependent inhibition of PDE5 at physiologically relevant concentrations.

REFERENCES

Maurice 2005, Front Biosci; 10:1221-8.

Example 6

Objective

The objective of this study was the investigation of the effect of two Ribes alkaloid fractions of the invention, RAP13 and RAP14 on mitochondrial biogenesis in mouse C2C12 myotubes. The C2C12 cell is a mouse myoblast cell line that can be differentiated into myotubes that have a high aerobic capacity resembling working muscles that have a high energy need.

Method

RAP13 and RAP14 were prepared in example 1 and comprised the following alkaloids of the invention:

RAP13-Alkaloids
Ribetril A: 3.3%
Ribetril B: 2.4%
Ribetril D: 5.4%
Ribetril E: 12.8%
Glucoindol A: 58.8%
Glucoindol B: 17.3%
RAP14-Alkaloids
Ribetril A: 21.7%
Ribetril B: 1.3%
Ribetril C: 7.5%
Ribetril D: 10.3%
Ribetril E: 33.0%
Glucoindol A: 26.2%

For dosing in cell medium RAP13-alkaloids and RAP14-alkaloids were dissolved in 10% ethanol (vol) and 1% volume added to obtain the desired concentration and a final concentration of ethanol of 0.1% (non-cytotoxic) in the incubation medium. Undifferentiated C2C12 cells (myoblasts) were cultivated in basal cell culture medium (Dulbecco's Modified Eagle's Medium—high glucose (Sigma Aldrich, D0819), with 4500 mg/L glucose, L-alanyl-glutamine and sodium bicarbonate, without sodium pyruvate with 10% FBS (Lot: 0739L), 100 unit/ml penicillin, 100 µg/ml streptomycin. The cell cultures were incubated at 37° C. in an atmosphere of 95% humidity and 5% CO2. 30,000 cells were seeded in 3.5 cm dishes and exposed to 25 or 50 ng/mL of RAP13-alkaloids or RAP14-alkaloids in double/triple determinations on the following day and incubated for 48 hours. For comparison, untreated controls and positive controls (resveratrol 30 µM and 50 mM pyruvate) were also incubated. After incubation, the cells were released from the dishes and were trypsinized, washed in media and resuspended in Hank's buffered saline solution with 0.06 µM Mito Tracker Green (MTG). The cells were incubated with MTG for 30 min at room temperature. The fluorescence was determined using FACS (Fluorescence-activated cell sorting). The fluorescence level was estimated as the geometric mean of the mean of signal subtracted the auto-fluorescence (estimated from unstained controls). Statistical analysis was performed with a Students t-test.

Results

Figure 4:
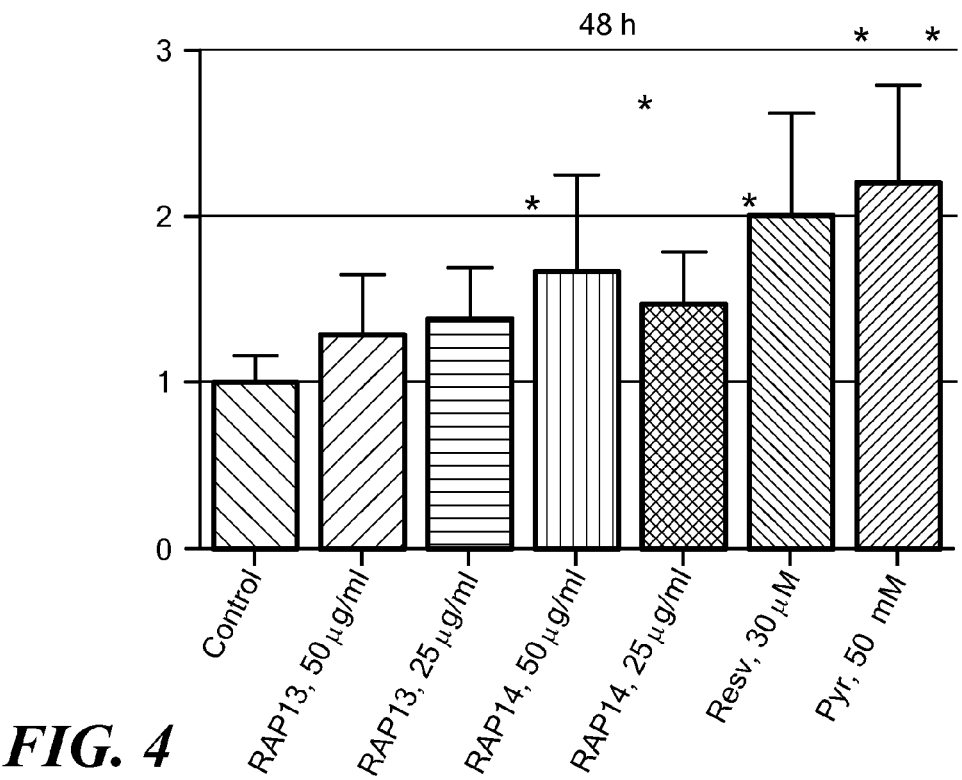
FIG. 4 shows a graph summarizing the results of exposing C2C12 cells to RAP13 alkaloids or RAP14 alkaloids.

Using MTG, an increased level of mitochondria was found in C2C12 cells exposed to RAP13-alkaloids or RAP14-alkaloids at 25 and 50 ng/mL for 48 hours compared to the untreated control. The difference was statistically significant ($p<0.05$) for 25 ng/mL of RAP13-alkaloids and statistically significant ($p<0.05$) for 25 ng/mL and 50 ng/mL of RAP14-alkaloids. The results are summarized in the FIG. 4.

Conclusion

In C2C12 myotubes RAP13-alkaloids and RAP14-alkaloids were able to significantly increase mitochondrial biogenesis at physiologically relevant concentrations. Increase of mitochondrial biogenesis in muscle cells is highly relevant when an increased capacity is needed to handle stressful conditions and/or the high energy need in working muscles, or when a decrease in mitochondrial amount and function due to inactivity, illness or age is impairing the functionality of the muscle cells.

Example 7

Objective

The objective of this study was to evaluate the effect of two *Ribes* alkaloid fractions of the invention, RAP13 and RAP14 on the spare respiratory capacity in mouse C2C12 myotubes exposed to a standardized mitochondrial stress test. The model provides valuable information regarding the functionality of the mitochondria in muscle cells by quantification of the mitochondrial ability to increase ATP-production above the basic level under maximally stressful conditions.

Method

RAP13 and RAP14 was prepared in example 1 and comprised the following alkaloids of the invention:

RAP13 Alkaloids
Ribetril A: 3.3%
Ribetril B: 2.4%
Ribetril D: 5.4%
Ribetril E: 12.8%
Glucoindol A: 58.8%
Glucoindol B: 17.3%
RAP14 Alkaloids
Ribetril A: 21.7%
Ribetril B: 1.3%
Ribetril C: 7.5%
Ribetril D: 10.3%
Ribetril E: 33.0%
Glucoindol A: 26.2%

For dosing in cell medium the RAP14-alkaloids and RAP14-alkaloids were dissolved in 10% ethanol (vol) and 1% volume added to obtain the desired concentration and a final concentration of ethanol of 0.1% (non-cytotoxic) in the incubation medium. The C2C12 cells were propagated in cell culture medium for 6 days with Asiros compounds included in the cell culture medium. Both the RAP13-alkaloids and the RAP14-alkaloids were tested in four concentrations (50 ng/ml, 16.7 ng/ml, 5.6 ng/ml and 1.9 ng/ml) in eight replicates. Basal cell culture medium consisted of Dulbecco's Modified Eagle's medium—no glucose (DMEM, Life Technologies, 11966) supplemented with 10% fetal bovine serum, 100 unit/ml penicillin, 100 µg/ml streptomycin, 1 mM sodium pyruvate and 1 g/1 of d-glucose. All cell cultures were incubated at 37° C. in an atmosphere of 95% humidity and 5% CO2. The medium was changed every 48 h (with fresh addition of test compounds at every medium change). On day 6 of the culture, the cells were replated into Seahorse assay plates (8 replicates per compound) at a density of 12,000 cells per well. On the day of the Seahorse measurement (day 7), the medium was changed to the XF assay medium (HCO free modified DMEM, Seahorse Bioscience), which was supplemented with 4 mM L-glutamine and 1 mM pyruvate. The pH of the media was adjusted to 7.4 at 37° C. The XF Cell Mito Stress Test was performed on a XF96 Extracellular Flux Analyzer (Seahorse Bioscience) by sequential additions of 1 µM oligomycin, 0.4 µM FCCP and 1 µM rotenone/antimycin A, according to the Seahorse BioScience XF Cell Mito Stress Test Kit User Manual XF96 Instructions. One way ANOVA followed by Dunnett's test was applied for test of difference between the vehicle group and the test groups. Differences are considered significant at $P<0.05$. Outliers were excluded from the analysis.

Results

The RAP13-alkaloids significantly increased the spare respiratory capacity of C2C12 cells exposed to a standardized mitochondrial stress test at all tested doses (50 ng/ml, 16.7 ng/ml, 5.6 ng/ml and 1.9 ng/ml) compared to the vehicle treated control. For the RAP14-alkaloids, there was a clear tendency towards elevated spare respiratory capacity at all tested doses, with a significant elevation at the two highest doses (50 ng/ml and 16.7 ng/ml).

The results are summarized in the tables below:

| Spare respiratory capacity (RAP13) | | | | | |
|---|---|---|---|---|---|
| Treatment | n | Mean | 95% CI | SE | SD |
| Control | 7 | 101.721 | 90.538 to 112,905 | 4.5705 | 12.0924 |
| RAP13 - 50 ng/ml | 8 | 124.310* | 115.093 to 133,527 | 3.8978 | 11.0245 |
| RAP13 - 16.7 ng/ml | 8 | 123.388* | 113.866 to 132,909 | 4.0266 | 11.3890 |
| RAP13 - 5.6 ng/ml | 8 | 124.891* | 117.758 to 132,025 | 3.0167 | 8.5324 |
| RAP13 - 1.9 ng/ml | 8 | 122.189* | 103.596 to 140,781 | 7.8627 | 22.2391 |

*$P < 0.05$

| Spare respiratory capacity (RAP14) | | | | | |
|---|---|---|---|---|---|
| Treatment | n | Mean | 95% CI | SE | SD |
| Control | 7 | 101.721 | 90.538 to 112.905 | 4.5705 | 12.0924 |
| RAP14 - 50 ng/ml | 8 | 120.474* | 110.607 to 130.340 | 4.1726 | 11.8020 |
| RAP14 - 16.7 ng/ml | 8 | 121.323* | 109.361 to 133.284 | 5.0586 | 14.3078 |
| RAP14 - 5.6 ng/ml | 8 | 111.145 | 102.695 to 119.595 | 3.5733 | 10.1069 |
| RAP14 - 1.9 ng/ml | 7 | 117.294 | 110.660 to 123.929 | 2.7114 | 7.1738 |

*$P < 0.05$

Conclusion

In C2C12 myotubes RAP13-alkaloids and RAP14-alkaloids were able to significantly increase mitochondrial spare respiratory capacity at low physiologically relevant concentrations. The C2C12 myotubes have a high aerobic capacity resembling the physiology in working muscles. Under certain conditions a tissue can require a sudden burst of additional cellular energy in response to stress or increased workload and this response depends on the spare respiratory capacity of the tissue. If the spare respiratory capacity of the cells is not sufficient to provide the required ATP, affected cells will function suboptimally and even risk being driven into senescence or cell death. An increased spare respiratory capacity in muscle cells is therefore extremely valuable to improve endurance in muscle function and capability, resistance to stress as well as counteracting the effects of senescence and inactivity.

Example 8

Objective

The objective of this study was to evaluate the effect of the Ribes alkaloid fraction of the invention, RAP15 on the spare respiratory capacity in mouse C2C12 myotubes exposed to mitochondrial stress.

Method

RAP15 was prepared in example 1 and comprised the following alkaloids of the invention:

RAP15-Alkaloids

Ribetril A: 16.0%

Ribetril B: 2.3%

Ribetril C: 4.9%

Ribetril D: 16.4%

Ribetril E: 15.5%

Glucoindol A: 31.0%

Glucoindol B: 13.9%

All procedures were identical to the method described in example 7. RAP15-alkaloids were tested in two concentrations, 20 ng/ml and 4 ng/ml, both in eight replicates. One way ANOVA followed by Dunnett's test was applied for test of difference between the vehicle group and the test groups. Differences are considered significant at $P<0.05$. Outliers were excluded from the analysis.

Results

The RAP15-alkaloids, significantly increased the spare respiratory capacity of C2C12 cells exposed to a standardized mitochondrial stress test at the tested doses compared to controls.

The results are summarized in the table below:

Spare Respiratory Capacity (RAP15)

| Spare respiratory capacity (RAP15) | | | | | |
|---|---|---|---|---|---|
| Treatment | n | Mean | 95% CI | SE | SD |
| Control | 6 | 138.862 | 130.180 to 147.544 | 3.3774 | 8.273 |
| RAP15-20 ng/ml | 8 | 169.114* | 160.519 to 177.709 | 3.6349 | 10.281 |
| RAP15-4 ng/ml | 8 | 181.275* | 158.437 to 204.113 | 9.6581 | 27.317 |

* $P < 0.05$

Conclusion

In C2C12 myotubes RAP15-alkaloids were able to significantly increase mitochondrial spare respiratory capacity at physiologically relevant concentrations comparable to previously tested doses of similar Ribes alkaloid fractions according to the invention.

Example 9

Objective

The objective of this study was the investigation of the hypocholesterolemic effect of two different Ribes alkaloid compositions of the invention, RAP2 and RAP4, in hyperlipidemic guinea pigs induced by high fat diet.

Test Compounds and Chemicals

The Ribes alkaloid concentrate RAP2 and the Ribes alkaloid extract RAP4 were produced in example 1. RAP2 and RAP4 were dissolved/suspended in 0.5% methylcellulose by sonicating for 20 minutes on a water bath at 50° C. Atorvastatin was used as the hypocholesterolemic reference compound. The vehicle was 0.5% methylcellulose Experimental Procedure Male Dunkin-Hartley guinea pigs weighing 300+/−30 g were acclimated one week before the in-life phase of the experiment. The study diet (Research Diets Inc, New Brunswick, N.J., USA) contained 15% corn oil and 0.25% cholesterol. A daily oral dose of 2000 mg/kg of RAP2 corresponding 9 µg/kg of Ribetril A and 82 µg/kg total Ribetrils as well as 632 µg/kg total Glucoindols was administered orally at a dosing volume of 10 mL/kg. A daily oral dose of 2000 mg/kg of RAP4 corresponding to 112 µg/kg of Ribetril A and 492 µg/kg total Ribetrils as well as 240 µg/kg total Glucoindols was administered orally at a dosing volume of 10 mL/kg. The positive control atorvastatin (10 mg/kg) and vehicle (0.5% methylcellulose) were each administered orally at a dosing volume of 10 mL/kg. The test compounds, reference compound or vehicle was administered by oral gavage to groups of 6 animals once daily for 28 consecutive days.

After fasting overnight, blood samples were obtained from the retro-orbital sinus of each animal 5 min before initial test substance and/or vehicle administration (pre-treatment) and 24 hours after dosing on days 14 and 28 (post-treatment). The serum total cholesterol (TC), low density lipoprotein cholesterol (LDL-C), high density lipoprotein cholesterol (HDL-C) and triglycerides (TG) were determined by an enzymatic method (Wako total cholesterol, LDL-C, HDL-C & TG diagnostic kit and Toshiba Automatic Analyzer Model TAB-120FR).

Results

After 28 days of treatment the RAP2 treated animals displayed a 45% reduction of triglyceride levels ($P<0.05$), a 36% decrease of serum total cholesterol ($P<0.05$) and a 35% decrease of LDL ($P<0.05$) as compared to the vehicle treated group. After only 15 days the RAP4 treated animals displayed a 32% reduction of triglyceride levels ($P<0.05$), which was further increased to a 50% reduction after 28 days of treatment as compared to the vehicle control group ($P<0.05$). Surprisingly, the RAP4 treated group displayed a 40% decrease of serum total cholesterol ($P<0.05$) and a 39% decrease of LDL ($P<0.05$) after 28 days of treatment, which was of the same order of magnitude as the positive control atorvastatin.

Conclusion

In terms of triglyceride reduction, both RAP2 and RAP4 were entirely superior to atorvastatin by displaying a fast onset and significant triglyceride reduction while atorvastatin did not significantly reduce triglycerides. Furthermore, both RAP2 and RAP4 were comparable to Atorvastatin in their considerable reducing effects on total cholesterol and LDL after 28 days of treatment. The faster onset of action and higher effect of RAP4 as compared to RAP2 could be due to its significantly higher content of Ribetril A since the total content of alkaloids was almost the same in the compositions of the invention.

REFERENCES

1. Aoki 2001, Arzneim-Forsch./Drug Res; 51(I) 197-203, 2001.
2. Van 2001, Diabetes; 50:1330-1335.
3. Bensch 1999, J Pharmacol Exp Ther; 289: 85-92.
4. Daggy 1997, J Lipid Res; 38: 491-502.

Example 10

Objective

The objective of this study was the investigation of the hypoglycemic effect of the *Ribes* alkaloid composition of the invention RAP4 in BKS Cg-Lepr db/Lepr db mice, a model of non-insulin dependent diabetes mellitus (NIDDM).

Test Compounds and Chemicals

The *Ribes* alkaloid extract RAP4 was produced in example 1. RAP4 was dissolved/suspended in 2% Tween 80 by sonication for 20 minutes on a water bath at 50° C. Metformin was used as the antidiabetic reference compound.

Experimental Procedure

Male non-insulin dependent diabetic mellitus (NIDDM) mice (BKS Cg-Lepr db/Lepr db) weighing 50+/−5 g were used at age of 12-13 weeks. A daily oral dose of 2000 mg/kg of RAP4 corresponding to corresponding to 112 μg/kg of Ribetril A and 492 μg/kg total Ribetrils as well as 240 μg/kg total Glucoindols was administered orally at a dosing volume of 10 mL/kg to 12 animals for a total of 14 consecutive days. The positive control of metformin (300 mg/kg) and vehicle (2% Tween 80) were each administered orally at a dosing volume of 10 mL/kg to groups of 6 animals once daily for a total of 14 consecutive days. Serum glucose levels were measured by means of an automated analyzer (TBA-120FR, Toshiba) and serum insulin by ELISA at zero min (pre-treatment) on Day 1, and at 90 min after the daily dosing (post-treatment) on Day 7 and Day 14.

Results

Oral administration of RAP4 for 14 consecutive days was associated with a significant decrease in serum glucose levels on day 14 post dosing, relative to the vehicle control in the Lepr db mouse model ($P<0.05$), which was also the case with the positive control metformin at 300 mg/kg ($P<0.05$). No decrease in insulin levels was observed.

Conclusion

The data show that the *Ribes* alkaloid composition of the invention was able to induce a significant reduction in blood sugar at day 14 ($P<0.05$) without affecting insulin levels.

REFERENCES

Johnson 1993, Diabetes; 42: 1179-1186, 1993.

Example 11

Objective

The objective of this study was the investigation of the effect of a *Ribes* alkaloid composition of the invention on wound healing in normal ICR mice with excisional cutaneous injury in two identical but independent studies.

Test Compounds and Chemicals

The *Ribes* alkaloid extract RAP4 was produced in example 1. RAP4 was dissolved/suspended in 0.5% carboxymethyl-cellulose (CMC) by sonicating for 20 minutes on a water bath at 50° C.

Experimental Procedure

Groups of 6 male ICR mice weighing 24+/−2 g were used. The animals were pretreated with vehicle (0.5% CMC) and 2000 mg/kg of RAP4 corresponding to 112 μg/kg of Ribetril A and 492 μg/kg total Ribetrils as well as 240 μg/kg total Glucoindols by gavage for seven consecutive days prior to excisional cutaneous injury (Day 1). The animals were housed in individual cages throughout the study. Under isoflurane gas anesthesia, the shoulder and back region of each animal was shaved. A sharp punch biopsy knife (ID 12 mm) was applied to remove the skin including panniculus carnosus and adherent tissues. The wound area, traced onto clear plastic sheets, was measured by use of an Image analyzer ProPlus (Media Cybernetics, Version 4.5.0.29) on Days 1, 3, 5, 7, 9 and 11. RAP4 and vehicle (0.5% CMC) were administered by oral gavage 1 hour before injury and once daily thereafter for a total of 10 consecutive days. The percent closure of the wound (%) was calculated, and wound half-closure time (CT50) was analyzed by linear regression using Graph-Prism (Graph Software USA). Unpaired Student's t-test was applied for comparison between the treated and vehicle groups at each measurement time point. Differences are considered significant at $P<0.05$.

Results

Oral administration of RAP4 significantly promoted wound healing in mice with excisional cutaneous injury with an early onset of action, resulting in significant reduction in CT50 value relative to the vehicle control. CT50 was 5.9 days for RAP4 and 8.3 days for the vehicle treated group. Three days after excisional injury the degree of wound closure was 78% higher in the *Ribes* treated group as compared to the vehicle treated group and after 5 days the degree of wound closure was more than twice as high in the *Ribes* treated group as compared to the vehicle control.

The results are summarized in the table below:

| Treatment | Route | Dose | | Day 1 | Day 3 | Day 5 | Day 7 | Day 9 | Day 11 | Wound Closure (%) CT50 (Days) |
|---|---|---|---|---|---|---|---|---|---|---|
| Vehicle | PO | 10 mL/kg × 17 | Mean | 0.0 | 19.9 | 19.0 | 42.1 | 59.9 | 69.3 | 8.3 |
| (0.5% CMC) | | | SEM | 0.0 | 3.0 | 4.3 | 3.6 | 3.2 | 5.2 | 0.5 |
| RAP4 | PO | 2000 mg/kg × 17 | Mean | 0.0 | 35.4* | 45.8* | 63.1* | 76.5* | 87.0* | 5.9* |
| | | | SEM | 0.0 | 3.6 | 3.6 | 3.4 | 3.5 | 1.8 | 0.3 |

*$P < 0.05$

The study was repeated with exactly the same study design. The results were very similar to the previous study as summarized in the table below:

|  |  |  | | Wound Closure (%) | | | | | CT50 |
|---|---|---|---|---|---|---|---|---|---|
| Treatment | Route | Dose | | Day 1 | Day 3 | Day 5 | Day 7 | Day 9 | Day 11 | (Days) |
| Vehicle | PO | 10 mL/kg × 17 | Mean | 0.0 | 18.0 | 27.1 | 42.2 | 60.6 | 67.1 | 8.2 |
| (0.5% CMC) | | | SEM | 0.0 | 2.6 | 2.3 | 3.4 | 4.7 | 4.2 | 0.5 |
| RAP4 | PO | 2000 mg/kg × 17 | Mean | 0.0 | 34.2* | 43.7* | 62.0* | 77.9* | 84.6* | 6.0* |
| | | | SEM | 0.0 | 2.0 | 2.9 | 1.8 | 3.1 | 1.4 | 0.2 |

*$P < 0.05$

Conclusion

The results of the present experiments convincingly confirmed the wound healing promoting effect of an orally administered *Ribes* alkaloid composition of the invention.

REFERENCES

Montesinos 1997, J Exp Med; 186:1615-1620, 1997.

Example 12

Objective

The objective of this study was the investigation of the effect of two *Ribes* alkaloid compositions of the invention, RAP4 and RAP16, on the wound healing in normal ICR mice with excisional cutaneous injury. The study set up was similar to the study design was similar to example 7 investigating a potential dose response and whether pretreatment influenced the result.

Experimental Procedure

The *Ribes* alkaloid extracts RAP4 and RAP 16 were produced in example 1. RAP4 and RAP16 were dissolved/suspended in 0.5% carboxymethylcellulose (CMC) by sonicating for 20 minutes on a water bath at 50° C. The test substances (RAP4: 2000 mg/kg corresponding to 112 µg/kg of Ribetril A and 492 µg/kg total Ribetrils as well as 240 µg/kg total Glucoindols), (RAP16: 2000 mg/kg corresponding to 3 µg/kg of Ribetril A and 18 µg/kg total Ribetrils as well as 97 µg/kg total Glucoindols) and vehicle (0.5% CMC) were administered by oral gavage to normal male ICR mice once daily starting 7 days before through 10 days after a 12 mm skin punch for a total of 17 consecutive days. A separate group was treated with RAP4 for 10 days without 7 days dosing prior to wounding. Percent closure of the wound (%) on Days 3, 5, 7, 9 and 11, and the wound half closure time (CT50) were determined. One way ANOVA followed by Dunnett's test was applied for test of difference between the vehicle group and the test groups. Differences are considered significant at $P<0.05$.

Results

Oral administration of RAP4 significantly promoted wound healing in mice pretreated for 7 days prior to excisional cutaneous injury with an early onset of action, resulting in significant reduction in CT50 value relative to the vehicle control. CT50 was 7.1 days for RAP4 and 9.3 days for the vehicle treated group. The group of mice that did not receive pretreatment with RAP4 also displayed a significantly faster wound healing (CT50 7.2), which was similar to the pretreated group, demonstrating that pretreatment is not necessary to obtain the wound healing promoting effect of the *Ribes* alkaloid composition RAP4. Another group of mice received another *Ribes* alkaloid composition RAP16. This group also displayed a significantly enhanced wound healing with a CT50 value of 7.9 days, demonstrating the effect of another *Ribes* alkaloid formulation of the invention on wound healing. However the effect of RAP16 was significantly lower than the effect of RAP4 corresponding to the much lower levels of *Ribes* alkaloids in RAP16 as compared to RAP4 indicating a dose-response of the *Ribes* alkaloids of the invention.

The results are summarized in the table below:

|  |  |  | | Wound Closure (%) | | | | | CT50 |
|---|---|---|---|---|---|---|---|---|---|
| Treatment | Route | Dose | | Day 1 | Day 3 | Day 5 | Day 7 | Day 9 | Day 11 | (Days) |
| Vehicle | PO | 10 mL/kg | Mean | 0.0 | 13.1 | 13.7 | 30.9 | 48.2 | 67.7 | 9.3 |
| (0.5% CMC) | | qd × 17 | SEM | 0.0 | 1.7 | 2.6 | 3.1 | 3.3 | 3.6 | 0.3 |
| RAP16 | PO | 2000 mg/kg | Mean | 0.0 | 18.1 | 28.8* | 39.2 | 60.2* | 73.5 | 7.9* |
| | | qd × 17 | SEM | 0.0 | 2.3 | 2.3 | 2.8 | 1.7 | 1.7 | 0.2 |
| RAP4 | PO | 2000 mg/kg | Mean | 0.0 | 21.2 | 37.4* | 47.8* | 63.2* | 79.6* | 7.1* |
| | | qd × 17 | SEM | 0.0 | 2.1 | 2.1 | 2.0 | 2.4 | 1.4 | 0.1 |
| RAP4 | PO | 2000 mg/kg | Mean | 0.0 | 20.1 | 37.1* | 48.8* | 65.3* | 80.6* | 7.0 |
| | | qd × 10 | SEM | 0.0 | 2.8 | 4.3 | 1.4 | 1.5 | 1.5 | 0.2 |

*$P < 0.05$

Conclusion

The results of the present experiment demonstrated the wound healing promoting effect of two different formulations of orally administered *Ribes* alkaloid compositions of the invention. The results indicated a dose-response dependent on the level/dosage of the alkaloids of the invention. Furthermore, it was clearly demonstrated that pretreatment prior to wound healing is not necessary to obtain a significant wound healing effect of an orally administered *Ribes* alkaloid composition of the invention.

REFERENCES

Montesinos 1997, J Exp Med; 186:1615-1620, 1997.

Example 13

Objective

The objective of this study was the investigation of the wound healing effect of three *Ribes* alkaloid compositions of the invention, RAP16, RAP17 and, RAP18 which is 50:50 mixture (by weight) of RAP-16 and RAP-17, in normal, male ICR mice with excisional cutaneous injury. The study procedure was similar to the study set up in example 11.

Experimental Procedure

The *Ribes* alkaloid compositions RAP16, RAP 17 and RAP18 were produced in example 1. RAP16, RAP 17 and RAP18 were dissolved/suspended in 0.5% carboxymethylcellulose (CMC) by sonicating for 20 minutes on a water bath at 50° C. The test substances (RAP16: 2000 mg/kg corresponding to 3 μs/kg of Ribetril A and 18 μg/kg total Ribetrils as well as 97 μg/kg total Glucoindols), (RAP17: 2000 mg/kg corresponding to 8 μg/kg of Ribetril A and 28 μg/kg total Ribetrils as well as 21 μg/kg total Glucoindols), (RAP18: 2000 mg/kg corresponding to 6 μg/kg of Ribetril A and 23 μg/kg total Ribetrils as well as 59 μg/kg total Glucoindols) and vehicle (0.5% CMC) were administered by oral gavage to normal male ICR mice once daily starting 7 days before through 10 days after a 12 mm skin punch for a total of 17 consecutive days. Percentage of the wound closure (%) on Days 3, 5, 7, 9 and 11 were recorded, and the wound half-closure time (CT50) was determined. One way ANOVA followed by Dunnett's test was applied for test of difference between the vehicle group and the test groups. Differences are considered significant at $P<0.05$. Differences are considered significant at $P<0.05$.

Results

Oral administration of RAP16 with the highest content of Glucoindols significantly promoted wound healing in mice pretreated for 7 days prior to excisional cutaneous injury, resulting in significant reduction in CT50 value (CT50 7.2 days) relative to the vehicle control (CT50 7.9 days). Oral administration of RAP17 with the highest content of Ribetriles promoted wound healing significantly and to a similar degree as seen with RAP16 (CT50 7.1 days) in another group of mice pretreated for 7 days prior to excisional cutaneous injury. Interestingly, RAP18 (50:50 mixture of RAP16 and RAP17) obviously had a more balanced content of Ribetrils and Glucoindols had a clearly more pronounced wound healing effect (CT50 6.4 days) compared to RAP16 and RAP17, indicating a synergistic effect between the Glucoindols primarily in RAP16 (derived from- *Ribes rubrum*) and the Ribetriles primarily in RAP17 (derived from- *Ribes nigrum*). This is further emphasized by the fact that the degree of wound closure as compared to the vehicle control was statistically significant on all 5 days of measurement for RAP18 ($p<0.05$) while RAP16 and RAP17 only obtain significant effect on 2 and 1 days, respectively.

The results are summarized in the table below:

Conclusion

The results of the present experiment convincingly demonstrated the wound healing promoting effect of two different orally administered *Ribes* alkaloid compositions of the invention with a high content of Ribetrils and Glucoindols, respectively. Furthermore, a significantly higher effect was observed with the 50:50 combination, indicating an enhanced and potentially synergistic effect when combining Ribetrils. This result forms a strong rationale for making alkaloid compositions of the invention based on combinations of- *Ribes rubrum* and *Ribes nigrum* due to their complementary alkaloid profile.

REFERENCES

Montesinos 1997, J Exp Med; 186:1615-1620, 1997.

Example 14

Objective

The objective of this study was the investigation of the wound healing effect of two formulations of orally administered *Ribes* alkaloid compositions of the invention, RAP4 and RAP16, in diabetic db/db mice, which is the diabetic mouse strain with the hardest to heal wounds.

Experimental Procedure

The experimental procedure was almost identical to the procedure described in example 7. In short, non-insulin dependent diabetic mellitus (NIDDM) male db/db mice (C57BLKS/J Iar-+Leprdb/+Leprdb), weighing 50+/−5 g (~10 weeks of age), provided by Institute for Animal Reproduction (IAR, Japan) were used. These animals exhibit hyperglycemia, and were used between 12-13 weeks of age. The *Ribes* alkaloid extracts RAP4 and RAP 16 were produced in example 1. RAP4 and RAP16 were dissolved/suspended in 0.5% carboxymethylcellulose (CMC) by sonicating for 20 minutes on a water bath at 50° C. The test substances (RAP4: 2000 mg/kg corresponding to 112 μs/kg of Ribetril A and 492 μg/kg total Ribetrils as well as 240 μg/kg total Glucoindols), (RAP16: 2000 mg/kg corresponding to 3 μg/kg of Ribetril A and 18 μg/kg total Ribetrils as well as 97 μg/kg total Glucoindols) or vehicle (0.5% CMC) were administered by oral gavage once daily starting 7 days before (pretreatment), and continuing until 15 days after a skin punch biopsy of 12 mm in diameter (skin biopsy day designated as Day 1) for a total of 22 consecutive days. Percent closure of the wound on Days 1, 2, 4, 6, 8, 10, 12, 14 and 16 and wound half-closure time (CT50) were determined. One way ANOVA followed by Dunnett's test was applied for test of difference between the vehicle group and the test groups. Differences are considered significant at $P<0.05$.

| Treatment | Route | Dose | | | Day 1 | Day 3 | Day 5 | Day 7 | Day 9 | Day 11 | Wound Closure (%) CT50 (Days) |
|---|---|---|---|---|---|---|---|---|---|---|---|
| Vehicle | PO | 10 mL/kg | | Mean | 0.0 | 18.9 | 23.1 | 41.6 | 59.5 | 74.9 | 7.9 |
| (0.5% CMC) | | qd × 17 | | SEM | 0.0 | 3.7 | 3.0 | 1.2 | 2.2 | 2.3 | 0.2 |
| RAP16 | PO | 2000 mg/kg | | Mean | 0.0 | 24.0 | 27.2 | 43.4 | 67.7* | 82.3* | 7.2* |
| | | qd × 17 | | SEM | 0.0 | 3.7 | 3.4 | 3.9 | 2.6 | 1.6 | 0.3 |
| RAP17 | PO | 2000 mg/kg | | Mean | 0.0 | 28.5 | 31.8 | 50.8* | 64.9 | 76.9 | 7.1* |
| | | qd × 17 | | SEM | 0.0 | 2.0 | 2.4 | 1.2 | 2.2 | 1.7 | 0.2 |
| RAP18 | PO | 2000 mg/kg | | Mean | 0.0 | 33.1* | 38.8* | 57.3* | 71.7* | 82.7* | 6.4* |
| | | qd × 17 | | SEM | 0.0 | 2.0 | 1.2 | 0.8 | 1.5 | 0.8 | 0.1 |

*$P < 0.05$

Results

Oral administration of RAP4-alkaloids and RAP16-alkaloids at 2000 mg/kg qd for 15 days with 7 days pretreatment significantly promoted wound healing in diabetic mice with excisional cutaneous injury on days 8, 10 or 16, resulting in significant reduction in the CT50 value for RAP4 of 9.6 days and RAP16 of 9.5 days relative to the vehicle control (CT50 10.7 days). The results are summarized in the table below:

|  |  |  |  | Wound Closure (%) | | | | | | | | CT50 |
|---|---|---|---|---|---|---|---|---|---|---|---|---|
| Treatment | Route | Dose |  | Day 2 | Day 4 | Day 6 | Day 8 | Day 10 | Day 12 | Day 14 | Day 16 | (Days) |
| Vehicle | PO | 10 mL/kg | Mean | 13.7 | 11.6 | 8.4 | 25.9 | 41.6 | 63.4 | 74.6 | 83.7 | 10.7 |
| (0.5% CMC) |  | qd × 22 | SEM | 2.6 | 1.8 | 1.6 | 1.5 | 2.7 | 3.4 | 1.8 | 1.8 | 0.3 |
| ASP-1268 | PO | 2000 mg/kg | Mean | 19.1 | 10.3 | 15.0 | 36.9* | 54.8* | 67.1 | 80.0 | 89.1 | 9.6* |
|  |  | qd × 22 | SEM | 3.4 | 3.4 | 3.4 | 3.1 | 2.5 | 2.1 | 2.6 | 2.1 | 0.3 |
| ASP-1269 | PO | 2000 mg/kg | Mean | 16.0 | 9.5 | 12.6 | 35.6* | 55.9* | 68.3 | 81.4 | 91.0* | 9.5* |
|  |  | qd × 22 | SEM | 2.1 | 2.8 | 2.7 | 1.6 | 1.6 | 1.1 | 2.1 | 1.0 | 0.2 |

*P < 0.05

Conclusion

The results of the present experiment convincingly demonstrated the wound healing promoting effect of two different orally administered *Ribes* alkaloid compositions of the invention in diabetic mice. The observed effect is convincing in a mouse strain resembling chronic hard to heal wounds.

REFERENCES

1. Montesinos 1997, J Exp Med; 186:1615-1620, 1997.
2. Botusan 2008, Proc Natl Acad Sci; 105: 19426-19431, 2008.

Example 15

Objective

The objective of this study was the investigation of the wound healing effect of two different formulations of orally administered *Ribes* alkaloid fractions of the invention, RAP4 and RAP16, in punch biopsy wounds in a different mouse species characterized by naked skin and performed at a different locations that the previous experiments in mice.

Experimental Procedure

The *Ribes* alkaloid compositions RAP4 and RAP16 were produced in example 1. RAP4 and RAP16 were formulated in demineralized water at a concentration of 250 mg/ml. Vehicle Control was demineralized water. Female C3.Cg TifBomTac (Taconic, Ry, Denmark) hairless but immunocompetent 12-14 weeks old mice (average weight 25 g) were randomly allocated to treatment or vehicle groups, each of 10 mice. Under light Hyponorm Dormicum anesthesia, two 8-mm full thickness punch biopsies were made to remove the skin including panniculus carnosus and adherent tissues on the dorsum. One biopsy was placed on each side of the dorsum. Test substances (RAP4: 2000 mg/kg corresponding to 112 μg/kg of Ribetril A and 492 μg/kg total Ribetrils as well as 240 μg/kg total Glucoindols), (RAP16: 2000 mg/kg corresponding to 3 μg/kg of Ribetril A and 18 μg/kg total Ribetrils as well as 97 μg/kg total Glucoindols) or vehicle was administered once daily by oral gavage. After excisional injury all groups were treated for a total of 14 consecutive days including the day of cutaneous injury designated Day 1. Under light Hyponorm Dormicum anesthesia, the wounds were measured 3 times a week. The edge of the wound was traced onto a glass microscope slide with a fine tipped permanent marker. The tracings were scanned digitally and the wound areas are analyzed and quantified digitally (blinded by treatment group) with ImageJ 1.47q (the US National Institutes of Health). One way ANOVA followed by Dunnett's test as well as Mann-Whitney non-parametric test was applied for test of difference between the vehicle group and the test groups. Differences are considered significant at P<0.05.

Results

Oral administration RAP4 and RAP16 at 2000 mg/kg/day in female hairless mice for 14 days with 7 days pretreatment significantly promoted wound healing compared to the control group. The observed difference was highly statistically significant for both *Ribes* alkaloid compositions at all time points from Day 3 to Day 8 (Mann-Whitney non-parametric test p<0.0001) and significant at Day 10: RAP4: p=0.028; RAP16: p=0.029. At day 8, the wounds in the treatment groups were almost entirely closed (89%) compared to 69% in the Vehicle group. One way ANOVA also demonstrated significance at D 3, 5 and 8.

Figure 5:
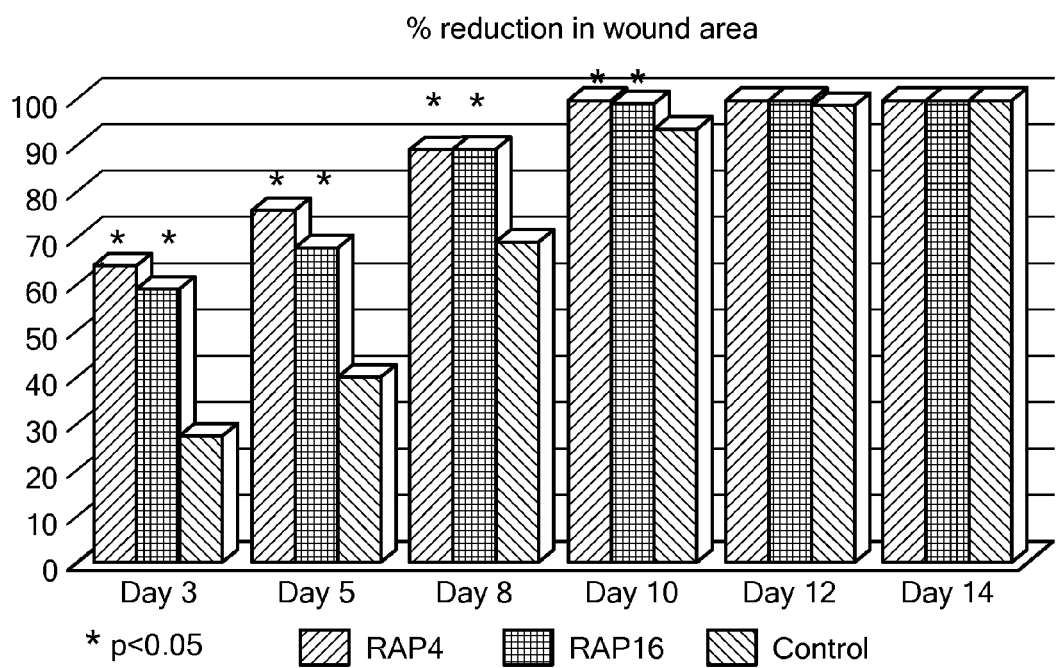
FIG. 5 shows the results of oral administration of RAP4 and RAP16 to mice to promote wound healing.

The results are shown in FIG. 5.

Conclusion

The results of the present experiment demonstrated a significant wound healing promoting effect of orally administered *Ribes* alkaloid compositions in hairless female mice. The experiment confirms the results on wound healing previously demonstrated in several studies in male ICR mice and diabetic mice performed at a different location and with a different study design, demonstrating that the wound healing effect of orally administered *Ribes* alkaloid compositions of the invention can be found across species and gender variations and independent of study location and study design.

Example 16

This example concerns the preparation of a nutritive product according to the invention (referred to as NP1 in the following).

Objective

To prepare a nutritive product composition for oral administration comprising a *Ribes* alkaloid concentrate of the invention.

Test Compounds and Chemicals

The *Ribes* alkaloid concentrate of the invention was RAP16 produced in example 1.

Experimental Procedure

The composition was prepared by dissolving 2000 g of RAP16 in purified water adjusted to a total volume of 4000 ml after addition of 2.0 g potassium sorbate as preservative.

Results

An easily administrable liquid formulation NP1 was obtained, stable and suitable for daily consumption.

Example 17

Objective

The objective of this study was to investigate the effect of an orally administered nutritive product produced in example 16, NP1 comprising *Ribes* alkaloids of the invention, on the healing of acute wounds in a human pilot study.

Materials and Procedure

The *Ribes* alkaloid composition NP1 was produced in example 1 and formulated for oral intake as a clear, red fluid, stored at 4° C. A daily dose of 25 ml NP1 twice daily (morning and evening) corresponding to 30 g RAP16 corresponding to 45 µg Ribetril A, 273 µg total Ribetrils and 1455 µg total Glucoindols.

The study was performed as an open cross over study with two sequential wound periods. A 45 year old, healthy man with normal skin and no history of impaired wound healing had eight 3 mm full thickness skin punch biopsies performed under local anesthesia as a horizontal line in the gluteal region just above crena anei. Hemorrhage was stopped with Spongostan and the wounds were covered with Mepilex Border Lite foam dressing. The wounds were photographed on the day of biopsy, designated day 1. Once daily for the next 10 days the wounds were photographed and 20 µl 0.5% carboxymethylcellulose, pH 3.5 was applied for 20 minutes before the wounds were covered with Mepilex. After 7 days pretreatment with orally administered NP1, which was initiated 3 weeks after the first wound incisions, eight new 3 mm full thickness skin punch biopsies were performed 1 cm above the previous biopsies. The wound incision day was designated as day 1. The study subject was treated with orally administered NP1 for 10 consecutive days after the biopsies. The wounds were treated and documented as in the control wound period.

Measurements and statistics: On the computer screen, the photographed wounds were standardized to a photographed measurement scale and the wound margins were traced onto clear glass microscope slides and scanned digitally. The wound areas were measured digitally with ImageJ 1.47q (National Institutes of Health, USA) and percent closure of the wound (%) on Days 2, 3, 4, 5, 6, 7, 8, 9 and 10 compared to Day 1 was calculated. The Student's t-test was used to determine significant difference between untreated and treated wounds. Significant difference is established at $P<0.05$ level.

Results

Orally administered NP1 in a healthy 45 year old man with normal skin for 10 days with 7 days pretreatment significantly promoted the healing of acute wounds. The healing was promoted with an early onset, speeding up the healing process from day 2.

The results are summarized in the table below:

| Day | Subject untreated (control) Wound Closure (%) | SEM | Subject treated with orally administered NP1 Wound Closure (%) | SEM |
|---|---|---|---|---|
| 1 | 0 | 0 | 0 | 0 |
| 2 | 14.8 | 2.1 | 30.9* | 4.3 |
| 3 | 19.3 | 7.2 | 54.8** | 4.1 |
| 4 | 31.4 | 5.1 | 74.0** | 2.9 |
| 5 | 43.1 | 4.0 | 79.5** | 2.1 |
| 6 | 61.2 | 4.9 | 84.3** | 2.7 |
| 7 | 63.1 | 3.8 | 85.2** | 2.6 |
| 8 | 65.0 | 3.8 | 86.2** | 2.1 |
| 9 | 65.7 | 4.6 | 90.8** | 2.1 |
| 10 | 70.6 | 5.4 | 92.7* | 1.8 |

*$P \leq 0.01$
**$P \leq 0.001$

Conclusion

The results of the present experiment demonstrated a significant wound healing promoting effect of an orally administered nutritive product comprising *Ribes* alkaloids of the invention, NP1, in a human subject. The fast onset of promotion of wound healing was similar to the effects observed in mouse studies of acute wound healing. The study demonstrates the relevance of the invention in the promotion of wound healing in humans.

REFERENCE

Montesinos 1997, J Exp Med; 186:1615-1620, 1997.
Example 18

This example concerns the preparation of a nutritive product according to the invention (referred to as NP2 in the following).

Objective

To prepare a nutritive product composition for oral administration comprising a *Ribes* alkaloid concentrate of the invention.

Test Compounds and Chemicals

The *Ribes* alkaloid concentrate of the invention was RAP4 produced in example 1.

Experimental Procedure

The composition was prepared by dissolving 1000 g of RAP4 in purified water adjusted to a total volume of 4000 ml after addition of 2.0 g potassium sorbate as preservative and 2.0 g Tween 80 as emulsifier.

Results

An easily administrable liquid formulation NP2 was obtained, stable and suitable for daily consumption.

Example 19

Objective

This example concerns the treatment of a human subject suffering from dyslipidemia and elevated BMI with a *Ribes* composition, comprising an increased amount of the alkaloid fraction of the invention in the form of the functional food composition produced in Example 18.

Procedure

A 44 year old man with a family history of hyperlipidemia had a stable elevated serum total cholesterol (TC) of 6.6, a low density lipoprotein (LDL) level of 4.8 and a triglyceride level of 1.86. His body weight was 81.8 kg on the day of the start of the treatment period, corresponding to a BMI of 25.3. From this starting point the subject initiated a twice daily oral administration of the functional food formulation NP2 produced in example 18. The total daily dose was 100 ml of NP2 corresponding to 25 g RAP4 was administered daily for the entire treatment period of 8 weeks. The daily dose of RAP4 corresponded to 1398 µg Ribetril A, 6145 µg total Ribetrils and 3000 µg total Glucoindols. There were no changes in food intake, life style, exercise or medication for the duration of the treatment period of 8 weeks.

Results

After four weeks of treatment the TC was reduced by 23% to 5.1, the LDL reduced by 27% to 3.5 and the triglyceride was reduced by 32% to 1.26. Furthermore the body weight was reduced by 2.0 kg to 79.8 and the BMI was reduced to 24.7.

After 8 weeks of treatment the TC was reduced by 26% to 4.9, the LDL reduced by 35% to 3.1 and the triglyceride level was reduced by 31% to 1.29. Furthermore the body weight was reduced by 2.7 kg to 79.1 and the BMI to 24.4.

Conclusion

In conclusion the orally administered nutritive product in the form of a food formulation comprising a *Ribes* alkaloid extract of the invention normalized the subject's blood lipid profile and aided in obtaining a normal BMI.

Example 20

This example concerns the preparation of a nutritive product according to the invention (referred to as NP3 in the following).

Objective

To prepare a nutritive product composition for oral administration comprising a combination of *Ribes* alkaloid concentrate of the invention derived from- *Ribes rubrum* in combination with *Ribes* alkaloid concentrate of the invention derived from *Ribes nigrum*.

| Test compounds and chemicals | |
|---|---|
| NP3 is composed of the following components (proportion by weight %): | |
| RAP16 (prepared in example 1) | 40.00% |
| RAP17 (prepared in example 1) | 40.00% |
| Water, purified | 16.505% |
| Magnesium sulphate heptahydrate | 2.027% |
| Potassium hydroxide | 1.300% |
| Potassium sorbate | 0.100% |
| Sucralose | 0.068% |

Experimental Procedure

NP3 is mixed sequentially without heating. The resulting product is stable and pourable for convenient administration.

The daily dose of 25 ml corresponds to 30 g of NP3 and is taken once daily diluted in water 1:4 resulting in a pleasantly tasting berry drink.

The daily dose provides 65 µg Ribetril A, 336 µg total Ribetrils and 708 µg total Glucoindols.

Example 21

Objective

This example concerns the health benefits obtained in a human subject in relation to joint health—by the daily oral intake of a nutritive product of the invention comprising an increased amount of *Ribes* alkaloids of the invention in the form of NP3 produced in example 20.

Subject

A 47 year old man (76) kg in a general good health with no medical conditions suffered from osteoarthritis in the first carpometacarpal joint of left hand with increasing symptoms of pain, swelling, stiffness and joint dysfunction for more than 2 years before diagnosis by a hand surgeon based on x-ray. After diagnosis, he had repeated intra-articular injection of corticosteroid every three months for one year, however, corticosteroid injections gave only transient relief and even the slightest use of the thumb would cause severe pain, which made many manually requiring tasks extremely painful. The symptoms finally became so severe and debilitating that he was offered surgery intended to make the joint functional and pain free. In the waiting period before the operation, the subject had a daily oral intake of the nutritive product of the invention. A daily dose of 25 ml (30 g) of NP3 once daily was used.

Procedure

The subject initiated a once daily oral administration of 30 g of the nutritive product of the invention NP3 produced in example 20. The daily intake lasted for 20 weeks. There were no changes in food intake, life style, exercise or medication for the duration of the treatment period.

Results

During the first 6 weeks of treatment the subject experienced a gradual decrease in the pain and intermittent swelling of the first carpometacarpal joint and at this point the subject estimated the pain to be 60% reduced. After 12 weeks of treatment, all symptoms including pain and swelling of the afflicted joint were entirely absent and the subject was able to use his thumb with no restrictions in all kinds of daily activities and manual tasks without causing pain or any other symptoms from the carpometacarpal joint (pain estimated to be 100% reduced). Over the next 8 weeks of treatment, the improvement remained stable and the operation of the joint was therefore cancelled. The subject has been able to resume all manual work tasks employing his left hand including playing the guitar to his great delight.

Conclusion

In conclusion, the orally administered nutritive product comprising *Ribes* alkaloids of the invention entirely removed the severe symptoms of osteoarthritis of the first carpometacarpal joint of the subject, making the joint functional and pain free and thereby eliminating the need for a planned operation of the joint. This convincingly demonstrates the ameliorating effects of the nutritive product of the invention on health deficits caused by excessive inflammatory processes in the body. It also indicates a beneficial effect on cartilage health which is a main factor in osteoarthritis.

Example 22

Objective

This example concerns the health benefits obtained in a human subject in relation to joint health—by the daily oral intake of a nutritive product of the invention comprising an increased amount of *Ribes* alkaloids of the invention in the form of the nutritive product produced in Example 20, NP3.

Subject

A 43 year old woman had suffered from increasing pain and reduced joint mobility in the first metatarsophalangeal joint of right foot for 4 years and left foot for 3 years. She had a diagnosis of osteoarthritis as evaluated by an orthopedic surgeon and by x-ray, causing increasing stiffness and joint pain on a daily basis with a marked worsening during the year before treatment was initiated. She was offered surgery but with no promise of relief of the pain. The symptoms of pain and reduced joint mobility were particularly troublesome for the subject during and in particular after activities that put stress or pressure on her big toes, including wearing high heels or if she performed fitness activities such as running. She feared for her future mobility.

Procedure

The subject initiated a once daily oral administration of 30 g of the nutritive product of the invention NP3 produced in example 20. The daily intake lasted for 4 weeks. There were no changes in food intake, life style, exercise or medication for the duration of the treatment period.

Results

After 2 weeks of treatment the pains in the first metatarsophalangeal joint of both feet were reduced by 80% as estimated by the subject and the mobility of the joints were almost back to normal. The subject was able to walk in high heels without pain and could even perform fitness activities such as running without pain and with no worsening afterwards. This pronounced improvement in the symptoms of osteoarthritis remained stable during the next two weeks of treatment, indicating a robust and lasting effect of the treatment. The subject had not experienced an improvement of the condition over the last 4 years; on the contrary the condition had been worsening. She was therefore very relieved to experience a reduction of the symptoms to such a pronounced degree. She decided to continue the treatment after the initial 4 weeks results.

Conclusion

In conclusion, an orally administered nutritive product comprising a *Ribes* alkaloid fraction of the invention improved the subject's symptoms of osteoarthritis in the metatarsophalangeal joints of the big toes to such a degree that she obtained almost normal joint-mobility and no longer suffered from significant pain and stiffness during activities that would have caused pain and worsening of the symptoms before treatment. This example clearly indicates an anti-inflammatory activity on osteoarthritis of the nutritive product comprising a *Ribes* alkaloid fraction of the invention.

Example 23

Objective

This example concerns the health benefits obtained in a human subject by the daily oral intake of a nutritive product of the invention comprising an increased amount of a *Ribes* alkaloids of the invention in the form of the food product produced in Example 20, NP3. The human subject was suffering from general age-related fatigue in relation to physically demanding exercise.

Subject

An 81 year old man (body weight 72 kg) in good general health had performed a regular training schedule of playing tennis for 2 hours twice a week (double with the same tennis partners) for many years. Even though he had this regular training schedule, over the years the subject experienced a gradual reduction in energy during training and increasing fatigue after the training sessions which he ascribed to his increasing age. Hence, he would always be too exhausted to continue playing another round after having played the scheduled two hours of tennis-double.

Procedure

The subject initiated a once daily oral administration of 30 g of the nutritive product of the invention NP3 produced in example 20. The daily intake lasted for 4 weeks. There were no changes in food intake, life style, exercise or medication for the duration of the treatment period.

Results

After 2 weeks of treatment the subject experienced a marked decrease in fatigue after 2 hours tennis double compared to before treatment initiation. He felt so full of energy and strength that he was able to play for one more hour before finishing the double. Furthermore, he felt no more tired after this prolonged session than he usually did after only two hours of playing tennis double. This pattern of decreased fatigue and ability to endure longer periods of playing tennis than habitually was repeated throughout the next two weeks of treatment, enabling the subject to continue playing for approximately 50% longer time than before treatment before reaching the same level of fatigue and physical exhaustion.

Conclusion

In conclusion, the orally administered nutritive product comprising a *Ribes* alkaloid fraction of the invention decreased the subject's general fatigue and level of exhaustion in relation to prolonged physical performance. The fatigue was ascribed to an age-related generally decreased threshold for endurance and decrease in muscle strength and function. After 2 weeks of treatment with the nutritive product comprising a *Ribes* alkaloid fraction of the invention these age-related symptoms of reduced energy and increased fatigue diminished impressively and considerably extended the period the subject was able to perform physical activity before exhaustion under standardized conditions.

Example 24

Objective

This example concerns the health benefits obtained in a healthy young athlete regarding physical performance and endurance by the daily oral intake of nutritive product of the invention comprising an increased amount of a *Ribes* alkaloids of the invention in the form of the food product produced in Example 20, NP3.

Subject

A 16 year old man (78 kg) was a physically well-trained subject with a stable training schedule of 5 sessions a week consisting of swimming and dry-land training. The swim training was a mixture of all 4 disciplines with both max and endurance passes in the weekly training. Dry-land training consisted of several high intensity exercises mainly focusing on strengthening the core and upper body. The subject's obtained level of fitness and endurance was well-established and stable and quantified regularly as part of the subject's training regime.

Procedure

A swim test was performed on the evening before treatment was initiated. The test was performed as a max-test focusing on how fast the subject could swim each of three passes in free style with a 15 second pause between each pass. The three passes were as follows:

First pass: 100 m.
Second pass: 50 m.
Third pass: 50 m.

After the test, the subject initiated a once daily oral administration of 30 g of the nutritive product of the invention NP3 produced in example 20. The daily intake lasted for 14 days. There were no changes in food intake, life style, exercise or medication for the duration of the treatment period.

After 7 days of treatment the subject performed another swim test identical to the one performed before initiation of the treatment.

After further 14 days of treatment without any changes in the subject's training regime, a third swim test was performed.

Results

The overall time for the compiled 200 m distance freestyle swim test was 143.14 seconds before treatment compared to 133.33 seconds after treatment. This is an improvement of 9.21 seconds, corresponding to a 6.4% improvement. The improved times were solely obtained in the last two passes of the test i.e. a total improvement of 12.1% in the last two passes of the second test. After further 14 days, the overall time for the compiled 200 m distance freestyle swim test was similar to the results of the second swim test (134.62 second). Again, the improved overall time was ascribable to improvements in the last to passes of the swim test. The young man described a "surplus of power" felt during the tests and was very impressed when presented the results.

The results are presented in the table below:

| Distance (meters) | Time (seconds) | Time (seconds) | Time (seconds) |
|---|---|---|---|
| 100 meters | 66.64 | 66.69 | 66.36 |
| 50 meters | 37.88 | 33.94 | 34.09 |
| 50 meters | 38.62 | 33.30 | 34.17 |
| Total 200 meters | 143.14 | 133.93 | 134.62 |

Conclusion

After 7 days of oral administration of a nutritive product of the invention comprising an increased amount of a *Ribes* alkaloid fraction to a young, fit male swimmer with stable times in his training passes, a pronounced improvement in the overall swim test time of 6.4% was obtained with an impressive improvement in the second half of the swim test of 12.1%, demonstrating an increase in the subject's endurance performance. This was an exceptional improvement which otherwise would only be obtainable through a highly intensified training regime over a longer period of time. As demonstrated by the results from the third swim test, the results were very robust indicating that the subject had reached a new higher plateau of endurance and performance, demonstrating the physical performance and endurance enhancing effects of the nutritive product of the invention comprising an increased amount of a *Ribes* alkaloid fraction.

Example 25

Objective

This example concerns the health benefits obtained in a young athlete indicated by the level of VO2 Max based on a Conconi test after daily oral intake of a nutritive product of the invention comprising an increased amount of a *Ribes* alkaloids of the invention in the form of the food product produced in Example 20, NP3.

Subject

A 28 year old man (73 kg) was a physically well-trained subject with a well-known level of fitness in the area of triathlon with a stable training schedule of 5 sessions a week consisting of long distance running and mountain biking. The subjects obtained level of fitness and endurance was well-known and stable and quantified regularly by the Conconi test as part of the subject's training regime. The test was well-known to the subject.

Procedure

A Conconi test was performed on the morning before treatment was initiated. The Conconi test is used mainly in endurance sports to determine the anaerobic threshold and calculate the VO2 Max. It consists in subjecting the subject to a progressively increasing workload while measuring the subject's heart rate. In the present case, the subject was running on a tread mill and the speed was increased by 0.5 km/hour every 200 meters until the subject could no longer maintain the speed. The heart rate was monitored and recorded every 5 seconds. Speed versus heart rate was then plotted on a graph from which the subject's VO2 Max could be calculated. A higher VO2

Max enables an athlete to tolerate higher intensity exercise for longer periods of time. After the test, the subject initiated a once daily oral administration of 30 g of the nutritive product of the invention NP3 produced in example 20. The daily intake lasted for 7 days. There were no changes in exercise regime, food intake, life style or medication for the duration of the treatment period.

After 7 days of treatment the subject performed another Conconi test identical to the one performed before initiation of the treatment.

Results

Based on the measurements of the Conconi test performed before initiation of oral administration of a nutritive product of the invention a VO2 Max of 55.27 ml/kg/min was calculated. After 7 days of oral administration of the nutritive product of the invention, a VO2 Max of 59.56 ml/kg/min was calculated based on the measurements of the Conconi test. The difference in VO2 Max was 4.27 ml/kg/min, an improvement of 7.8%.

The subject described a feeling of excess energy during the last test despite running to his maximum limit (speed).

The results are presented in the table below:

| Conconi-test VO2 Max (ml/kg/min) | |
| --- | --- |
| Before oral administration of Ribes alkaloid composition, NP3 | 55.27 |
| After 7 days administration of Ribes alkaloid composition, NP3 | 59.56 |
| Difference | 4.27 (7.8%) |

Conclusion

After only 7 days of oral administration of the nutritive product of the invention to a young, fit male long-distance runner with stable times in his training passes, an improvement in the calculated VO2 Max of 7.8% was obtained without any changes in the subject's training regime during the treatment period. This was an exceptional improvement, considering the subject's high level of fitness and consequently very high VO2 Max before treatment, which would normally require hard interval training for a longer period of time to improve notably.

Example 26

Objective

This example concerns the health benefits obtained in a male athlete regarding physical endurance and lactate threshold after daily oral intake of a nutritive product of the invention comprising an increased amount of a *Ribes* alkaloids of the invention in the form of the food product produced in Example 20, NP3.

Subject

A 48 year old man (80 kg) was a physically well-trained subject with a stable training schedule of average 5 sessions a week (5 hours biking/week). The subject's obtained level of fitness, endurance and average heart rate during long distance high speed training passes was well-known throughout years of training and races. Hence, the maximum heart rate during long distance high speed training passes was never above 175 bpm (i.e. an anaerobic threshold of 175 bpm).

Procedure

The subject initiated a once daily oral administration of 30 g of the nutritive product of the invention NP3 produced in example 20. The daily intake lasted for 7 days. There were no changes in exercise regime, food intake, life style or medication for the duration of the treatment period.

Results

After 4 days of treatment the subject was tested in a road race in Southern France in the mountains. The subject used a GPS unit measuring heart rate, time and speed. During a long climb and a succeeding high pace speed ridge it was surprisingly observed that the heart rate was stable around 185 bpm during approximately 20 minutes which was 5.7% higher than his previously known anaerobic threshold, indicating a significantly higher anaerobic threshold than previously obtained.

Conclusion

Average heart rate during long distance high intensity training is an indicator of the anaerobic threshold and endurance capability. In this example, after only 4 days of daily oral administration of the nutritive product of the invention, a 48 year old physically well-trained man with a well-established anaerobic threshold heart rate of 175 bpm during long distance high intensity cycle training improved his average heart rate 5.7% to 185 bpm for 20 minutes during a long distance high intensity training pass, indicating a fast onset of action and an increased endurance and lactate threshold exerted by the *Ribes* alkaloids of the invention.

Example 27

Objective

This example concerns the health benefits obtained in a human subject by the daily oral intake of a nutritive product of the invention comprising an increased amount of a *Ribes* alkaloids in the form of the food product produced in Example 19. The subject suffered from persisting physical and mental fatigue in the rehabilitation period after a severe brain trauma.

Subject

A 75-year old woman (57) kg with no medical conditions and a general good health and physical constitution was in a reconstitutional phase after a traumatic intracranial hemorrhage (fall-accident) 3 months earlier, which had put her into a coma and necessitated an acute surgical evacuation of the hemorrhage to relieve pressure on the brain tissue. Intracranial epidural hematoma is considered to be the most serious complication of head injury. After the accident, as a consequence of the impact of hemorrhage and concussion on the brain tissue, she suffered from expressive aphasia in the earliest phase, and was feeling physically weak and easily exhausted both mentally and physically with a markedly increased need for sleep. She gradually and steadily recovered over the next months but suffered from severe fatigue and slept 1½ hours longer in the morning and went to bed and slept 2 hours earlier than before the accident. In total her need for sleep was 3½ hours longer than before the accident. She did not have the energy to go for her usual daily walk either. Even though she was on a routine physical rehabilitation program which improved her physical ability her severe fatigue remained her biggest challenge.

Procedure

The subject initiated a once daily oral administration of 30 g of the nutritive product of the invention NP3 produced in example 19. The daily intake lasted for 4 weeks. There were no changes in food intake, life style, exercise or medication for the duration of the treatment period.

Results

After 1 week of treatment the subject experienced a pronounced increase in her general feeling of physical and mental energy. She was now able to rise from bed at seven o'clock as before the accident (1½ hour earlier) and even perform the domestic duties she had always performed before the accident without becoming tired. She was able to carry on during the day with a feeling of a surplus of energy and go to bed at 22 pm, 1 hours later than before initiating the daily intake of the nutritive product of the invention, which corresponded to a 71% reduction of her additional need for sleep caused by the trauma.

After 2 weeks of treatment the subject felt a further surplus energy and had a 100% reduction of the additional need for sleep and was also able to take a daily walk again because of her regained energy. The convincing improvement of her positive mental and physical exhaustion threshold was not preceded by any changes in her training schedule or other changes in her physical or mental circumstances and were so considerable that she felt close to being back to her physical and mental condition before the accident. This improvement was stable throughout the rest of treatment period.

Conclusion

In conclusion, the continuous physical and mental fatigue which had relentlessly persisted during the rehabilitation period was dramatically decreased within a week of taking a nutritive product comprising a *Ribes* alkaloid fraction of the invention. This indicates a major contribution to improvement and normalization of the functioning of the central nervous system, which was very significant since the subject was able to resume her daily routines and activities at a level comparable to her previous capacity with an amazing speed.

ITEMS

1. A alkaloid compound according to formula (I):

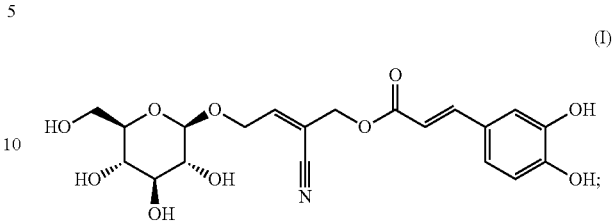

2. The alkaloid compound according to item 1, wherein the compound is (E)-(E)-2-cyano-4-(((2R,3R,4S,5S,6R)-3,4,5-trihydroxy-6-(hydroxymethyl)tetrahydro-2H-pyran-2-yl)oxy)but-2-en-1-yl 3-(3,4-dihydroxyphenyl)acrylate ("Ribetril A").

3. An alkaloid fraction obtainable from *Ribes*, said fraction comprising an increased mass fraction of at least one compound selected among the compounds of formula (I) and item 2 and the compounds of formula (II) and formula (III), as compared to *Ribes*;
wherein the compounds of formula (II) are:

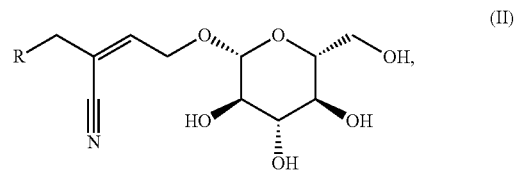

wherein R is an acyloxy moiety derived from an acid selected from the group consisting of 4-hydroxy-3-methoxybenzoic acid, 4-hydroxybenzoic acid, (E)-3-(4-hydroxy-3-methoxyphenyl)acrylic acid and (E)-3-(4-hydroxyphenyl)acrylic acid;
and wherein the compounds of formula (III) are:

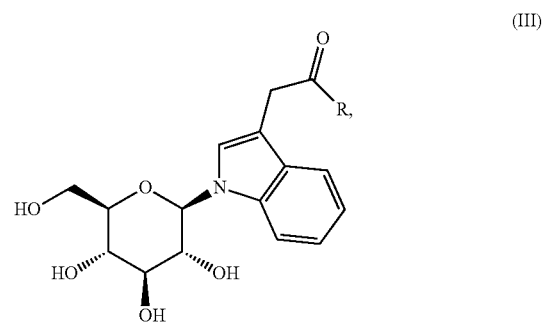

wherein R is OH or OCH3.

4. The alkaloid fraction according to item 3, wherein said at least one compound according to formula (II) is selected from the group consisting of:
(E)-(E)-2-cyano-4-(β-D-glucopyranosyloxy)but-2-en-1-yl 3-(4-hydroxy-3-methoxyphenyl)acrylate ("Ribetril B");
(E)-(E)-2-cyano-4-(β-D-glucopyranosyloxy)but-2-en-1-yl 3-(4-hydroxyphenyl)acrylate ("Ribetril C");
(E)-2-cyano-4-(β-D-glucopyranosyloxy)but-2-en-1-yl 4-hydroxy-3-methoxybenzoate ("Ribetril D");

(E)-2-cyano-4-(β-D-glucopyranosyloxy)but-2-en-1-yl 4-hydroxybenzoate ("Ribetril E").

5. The alkaloid fraction according to item 3, wherein said at least one compound according to formula (III) is selected from the group consisting of:
1-β-D-glucopyranosyl-1H-indole-3-acetic acid ("Glucoindol A"); and
1-β-D-glucopyranosyl-1H-indole-3-acetic acid methyl ester ("Glucoindol B").

6. The alkaloid fraction according to item 3, wherein said at least one compound is selected among the compounds of formula (I) and formula (II).

7. The alkaloid fraction according to any one of items 3-6, comprising at least one compound of formula (I) and at least one compound of formula (II) or formula (III), wherein the weight ratio of the total amount of compounds according to formula (I) and the total amount of compounds according to formula (II) or (III) is between 1:100 and 100:1, more preferably between 1:20 and 20:1, more preferably between 1:10 and 10:1 and most preferably between 1:5 and 5:1.

8. The alkaloid fraction according to any one of items 3-7, wherein the mass fraction of compounds according to formula (I) constitutes 50%-99% of the total amounts of alkaloids in said fraction.

9. The alkaloid fraction according to any one of items 3-8, wherein the mass fraction of compounds according to formula (II) constitutes 50%-99% of the total amounts of alkaloids in said fraction.

10. An extract, juice or concentrate of- *Ribes*, comprising an increased mass fraction of the alkaloid or alkaloid fraction according to any one of items 3-9, as compared to *Ribes*.

11. The extract, juice or concentrate according to item 10, wherein the *Ribes* is selected among *Ribes rubrum* or- *Ribes nigrum*.

12. The extract, juice or concentrate of *Ribes* according to item 10 or 11, further comprising:
i) at least one flavonol selected from the group consisting of quercetin, myricetin, kaempferol and glucosides thereof; and/or
ii) at least one phenolic acid selected from the group consisting of p-hydroxybenzoic acid, vanillic acid, caffeic acid, p-coumaric acid, ferulic acid and glucosides thereof; and/or
iii) at least one proanthocyanidin selected from the group consisting of epicatechin, epigallocatechin and oligomers thereof; and/or
iiii) at least one anthocyanidin selected from the group consisting of cyanidin, delphinidin, and/or glucosides thereof.

13. The extract, juice or concentrate of *Ribes* according to any of the items 10-12, wherein the mass fraction of Ribetril A of said extract, juice or concentrate of *Ribes* is selected among 0.0001%-100%, 0.00025%-90%, 0.0005%-80%, 0.00025%-70%, 0.0005%-60%, 0.00075%-50%, 0.001%-45%, 0.0025%-40%, 0.005%-35%, 0.0075%-30%, 0.01%-25%, 0.025%-20, 0.05%-19%, 0.075%-18%, 0.1%-17%, 0.25%-16%, 0.5%-15%, 0.75%-14%, 1%-13%, 1.5%-12%, 2.0%-11%, 3.0%-10%, 4.0%-9.0%, 5.0%-8.0% and 6.0%-7.0%.

14. The extract, juice or concentrate of *Ribes* according to any of the items 10-12, wherein the total mass fraction of Ribetril A, Ribetril B, Ribetril C, Ribetril D and/or Ribetril E of said extract, juice or concentrate of *Ribes* is selected among 0.0002%-100%, 0.0005%-90%, 0.0008%-80%, 0.001%-70%, 0.0025%-60%, 0.005%-50%, 0.0075%-45%, 0.01%-40%, 0.025%-35%, 0.05%-30%, 0.075%-25%, 0.1%-20, 0.25%-19%, 0.5%-18%, 0.75%-17%, 1.0%-16%, 1.5%-15%, 2.0%-14%, 2.5%-13%, 3.0%-12%, 4.0%-11%, 5.0%-10%, 6.0%-9.0% and 7.0%-8.0%.

15. The extract, juice or concentrate of *Ribes* according to any of the items 10-12, wherein the total mass fraction of Glucoindol A and/or Glucoindol B of said extract, juice or concentrate of *Ribes* is selected among 0.0008%-100%, 0.001%-90%, 0.0025%-80%, 0.005%-70%, 0.0075%-60%, 0.01%-50%, 0.025%-45%, 0.05%-40%, 0.075%-35%, 0.1%-30%, 0.25%-25%, 0.5%-20, 0.75%-19%, 1.0%-18%, 1.5%-17%, 2.0%-16%, 2.5%-15%, 3.0%-14%, 3.5%-13%, 4.0%-12%, 4.5%-11%, 5.0%-10%, 6.0%-9.0% and 7.0%-8.0%.

16. A nutritive product obtainable by providing a food or non-food product and adding or increasing the amount of at least one alkaloid or alkaloid fraction according to any of items 1-9.

17. The nutritive product according to item 16, wherein said nutritive product comprises an increased amount of said at least one alkaloid or alkaloid fraction, as compared to the amount of said alkaloid occurring in nature.

18. The nutritive product according to any of the items 16-17, wherein the mass fraction of Ribetril A of said nutritive product is selected among 0.0001%-100%, 0.00025%-90%, 0.0005%-80%, 0.00025%-70%, 0.0005%-60%, 0.00075%-50%, 0.001%-45%, 0.0025%-40%, 0.005%-35%, 0.0075%-30%, 0.01%-25%, 0.025%-20, 0.05%-19%, 0.075%-18%, 0.1%-17%, 0.25%-16%, 0.5%-15%, 0.75%-14%, 1%-13%, 1.5%-12%, 2.0%-11%, 3.0%-10%, 4.0%-9.0%, 5.0%-8.0% and 6.0%-7.0%.

19. The nutritive product according to any of the items 16-17, wherein the total mass fraction of Ribetril A, Ribetril B, Ribetril C, Ribetril D and/or Ribetril E of said nutritive product is selected among 0.0002%-100%, 0.0005%-90%, 0.0008%-80%, 0.001%-70%, 0.0025%-60%, 0.005%-50%, 0.0075%-45%, 0.01%-40%, 0.025%-35%, 0.05%-30%, 0.075%-25%, 0.1%-20, 0.25%-19%, 0.5%-18%, 0.75%-17%, 1.0%-16%, 1.5%-15%, 2.0%-14%, 2.5%-13%, 3.0%-12%, 4.0%-11%, 5.0%-10%, 6.0%-9.0% and 7.0%-8.0%.

20. The nutritive product according to any of the items 16-17, wherein the total mass fraction of Glucoindol A and/or Glucoindol B of said nutritive product is selected among 0.0008%-100%, 0.001%-90%, 0.0025%-80%, 0.005%-70%, 0.0075%-60%, 0.01%-50%, 0.025%-45%, 0.05%-40%, 0.075%-35%, 0.1%-30%, 0.25%-25%, 0.5%-20, 0.75%-19%, 1.0%-18%, 1.5%-17%, 2.0%-16%, 2.5%-15%, 3.0%-14%, 3.5%-13%, 4.0%-12%, 4.5%-11%, 5.0%-10%, 6.0%-9.0% and 7.0%-8.0%.

21. The nutritive product according to any of the items 16-18, allowing provision of a single dosage of an alkaloid or alkaloid fraction according to any of items 1-9 selected among 0.01-5000 mg, 0.05-4000 mg, 0.1-3000 mg, 0.25-2000, 0.5-1750 mg, 0.75-1500 mg, 1-1250 mg, 1.5-1000 mg, 2-900 mg, 2.5-800 mg, 3-700 mg, 4-600 mg, 5-500 mg, 7.5-400 mg, 10-350 mg, 15-300 mg, 20-250 mg, 30-200 mg, 40-150 mg, 50-125 mg and 75-100 mg.

22. The nutritive product according to any of the items 16-21, wherein said at least one alkaloid or alkaloid fraction is used as a nutritive product per se, optionally with the addition of one or more additional components or ingredients, such as a preservative.

23. The nutritive product according to any of the items 16-22, wherein said nutritive product has been labeled to inform about the physiological or medical benefit of said nutritive product.

24. The nutritive product according to any of the items 16-23, for supporting, normalizing or improving muscle function, athletic performance, mitochondrial function, neurological function, mental function, skin function, metabolic function, cardiovascular function, joint function or for decreasing at least one physiological sign of aging.

25. The nutritive product according to any of the items 16-24 comprising an extract, juice or concentrate of *Ribes* according to any of the items 10-13.

26. The nutritive product according to item 25 comprising an extract, juice or concentrate of *Ribes rubrum* and an extract, juice or concentrate of- *Ribes nigrum*, wherein the weight ratio between *Ribes rubrum* and *Ribes nigrum* is selected among 1:20-20:1, 1:15-15:1, 1:10-10:1, 1:9-9:1, 1:8-8:1, 1:6-6:1, 1:5-5:1, 1:4-4:1, 1:3-3:1, 1:2-2:1 and 1:1.

27. The nutritive product according to any of the items 16-26 further comprising at least one additional active compound, said active compound preferably being selected from the group consisting of alpha-linolenic acid, Beta-glucans, chitosan, hydroxypropyl methylcellulose, pectins, glucomannan, guar gum, linoleic acid, red yeast rice, plant sterols and plant stanols, docosahexaenoic acid, eicosapentaenoic acid, biotin, folate, magnesium, niacin, thiamine, vitamin B12, vitamin C, vitamin B6, iodine, iron, zinc, carbohydrates, copper, potassium, calcium, manganese, vitamin D, protein, amino acids, chromium, pantothenic acid, phosphorus hydroxypropylmethylcellulose, alphacyclodextrin, arabinoxylan produced from wheat endsperm, water, valine, lysine, threonine, leucine, isoleucine, tryptophan, phenylalanine, methionine, cysteine, histidine, glycine, alanine, serine, cysteine, tyrosine, aspartic acid, proline, hydroxyproline, citrulline, arginine, ornithine, hydroxyglutamic acid, glutamine, glutamic acid.

28. A nutritive product according to any of the items 16-27, for supporting general well being.

29. A nutritive product according to any of the items 16-27, for supporting or improving at least one aspect of mitochondrial physiology, said aspect selected from the group consisting of mitochondrial function, mitochondrial biogenesis and mitochondrial spare respiratory capacity.

30. A nutritive product according to any of the items 16-27, for regulating at least one aspect of skin physiology, said aspect preferably being selected among supporting skin integrity, normalizing or improving skin function and structure, contributing to the maintenance of normal skin, contributing to the maintenance of normal formation of connective tissue and contributing to the maintenance of normal mucous membranes.

31. A nutritive product according to any of the items 16-27, for regulating at least one aspect of aging physiology, said aspect preferably being selected among supporting healthy aging, decrease age-related loss of muscle mass, decrease age-related loss of muscle strength, decrease age-related loss of heart muscle function, decrease age-related deterioration of skin structure, decrease age-related loss of skin regeneration, decrease age-related deterioration of bone formation, decrease age-related loss of endocrine function, decrease age-related loss of neuronal function, decrease age-related deterioration of mitochondrial function, decrease age-related deterioration of mitochondrial biogenesis, decrease age-related deterioration of mitochondrial spare respiratory capacity, decrease age-related loss of vision function, decrease age-related loss of memory function, decrease age-related loss of mental function, decrease age-related loss of physical endurance, decrease age-related decline in muscle function, supporting muscle function in the elderly and improving muscle endurance in the elderly.

32. A nutritive product according to any of the items 16-27, for regulating at least one aspect of muscle physiology, said aspect preferably being selected among counteracting sedentary decline in muscle function, improving muscle function decreased by inactivity, supporting muscle function decreased by inactivity, contributing to normal muscle function, contributing to the maintenance normal muscle function, contributing to growth in muscle mass, contributing to the maintenance in muscle mass and contributing to the normal function of the heart.

33. A nutritive product according to any of the items 16-27, for regulating at least one aspect of endurance and sports physiology, said aspect preferably being selected among improving athletic performance, supporting muscle function during sports performance, supporting muscle function during endurance performance, improving endurance during sports performance, contributing to the maintenance of endurance performance during prolonged endurance exercise, increasing physical performance in successive bursts of short-term, high intensity exercise, improving anaerobic threshold in athletes, improving VO2max in athletes, improving mitochondrial spare respiratory capacity, supporting normal function of the mitochondria, empowering the mitochondria, improving mitochondrial biogenesis, counteracting tiredness and fatigue, contributing to reduction of tiredness and fatigue and contributing to normal energy-yielding metabolism.

34. A nutritive product according to any of the items 16-27, for regulating at least one aspect of joint physiology, said aspect preferably being selected among supporting cartilage and joint function and supporting the flexibility of joints.

35. A nutritive product according to any of the items 16-27, for regulating at least one aspect of cognitive and mental function, said aspect preferably being selected among improving absentmindedness, supporting mental function, supporting a healthy mental function, counteracting forgetfulness, improving memory function, contributing to normal psychological function, contributing to maintenance of normal brain function, contributing to normal cognitive function, contributing to normal functioning of the nervous system and contributing to normal neurotransmission.

36. A nutritive product according to any of the items 16-27, for regulating at least one aspect of blood lipid physiology, said aspect preferably being selected among contributing to the maintenance of normal blood cholesterol levels, contributing to the maintenance of normal blood triglyceride levels, lowering or reducing blood cholesterol and lowering or reducing blood triglyceride levels.

37. A nutritive product according to any of the items 16-27, for regulating at least one aspect of blood glucose physiology, said aspect preferably being selected among contributing to the maintenance of normal blood glucose levels.

38. A nutritive product according to any of the items 16-27, for improving the healing of a wound. 39. A kit of parts comprising a nutritive product according to any of the items 16-38, and instructions for use, including information about the medical or physiological benefit of said at least one alkaloid.

40. A non-therapeutic use of a nutritive product according to any of the items 16-38, for supporting, normalizing or improving muscle function, athletic performance, mitochondrial function, neurological function, mental function, skin function, metabolic function, cardiovascular function, joint function or for decreasing at least one physiological sign of aging.

41. An alkaloid for use as a medicament selected among the group comprising the compounds of formula (I), (II) and (III), preferably selected from the group consisting of Ribetril A, Ribetril B, Ribetril C, Ribetril D, Ribetril E, Glucoindol A and Glucoindol B.

42. Use of an alkaloid selected among the group comprising the compounds of formula (I), (II) and (III), preferably selected from the group consisting of Ribetril A, Ribetril B, Ribetril C, Ribetril D, Ribetril E, Glucoindol A and Glucoindol B, for preparing a medicament.

43. The use according to item 42, wherein said medicament is for the treatment or prevention of a disease selected among the group consisting of a dermatological disease, a cardiovascular disease, a dyslipidemic disorder, a pre-diabetic disorder, type 2 diabetes, metabolic syndrome, obesity, frailty, sarcopenia, osteoarthritis, an inflammatory disease and diseases associated with mitochondrial dysfunction.

44. The use according to item 42, wherein said medicament is for the treatment or prevention of a wound.

45. An alkaloid for use in or as a nutritive product, said alkaloid being selected among the group comprising the compounds of formula (I), (II) and (III), preferably selected among Ribetril A, Ribetril B, Ribetril C, Ribetril D, Ribetril E, Glucoindol A and Glucoindol B.

46. A use of an alkaloid selected among the group comprising the compounds of formula (I), (II) and (III), preferably selected from the group consisting of Ribetril A, Ribetril B, Ribetril C, Ribetril D, Ribetril E, Glucoindol A and Glucoindol B, for preparing a nutritive product.

47. The use according to item 46 for a nutritive product for supporting, normalizing or improving muscle function, athletic performance, mitochondrial function, neurological function, mental function, skin function, metabolic function, cardiovascular function, joint function or for decreasing at least one physiological sign of aging.

48. The use according to item 46 for a nutritive product for supporting general well being.

49. The use according to item 46 for a nutritive product for supporting or improving at least one aspect of mitochondrial physiology, said aspect selected from the group consisting of mitochondrial function, mitochondrial biogenesis and mitochondrial spare respiratory capacity.

50. The use according to item 46 for a nutritive product for regulating at least one aspect of skin physiology, said aspect preferably being selected among supporting skin integrity, normalizing or improving skin function and structure, contributing to the maintenance of normal skin, contributing to the maintenance of normal formation of connective tissue, and contributing to the maintenance of normal mucous membranes.

51. The use according to item 46 for a nutritive product for regulating at least one aspect of aging physiology, said aspect preferably being selected among supporting healthy aging, decrease age-related loss of muscle mass, decrease age-related loss of muscle strength, decrease age-related loss of heart muscle function, decrease age-related deterioration of skin structure, decrease age-related loss of skin regeneration, decrease age-related deterioration of bone formation, decrease age-related loss of endocrine function, decrease age-related loss of neuronal function, decrease age-related deterioration of mitochondrial function, decrease age-related deterioration of mitochondrial biogenesis, decrease age-related deterioration of mitochondrial spare respiratory capacity, decrease age-related loss of vision function, decrease age-related loss of memory function, decrease age-related loss of mental function, decrease age-related loss of physical endurance, decrease age-related decline in muscle function, supporting muscle function in the elderly and improving muscle endurance in the elderly.

52. The use according to item 46 for a nutritive product for regulating at least one aspect of muscle physiology, said aspect preferably being selected among counteracting sedentary decline in muscle function, improving muscle function decreased by inactivity, supporting muscle function decreased by inactivity, contributing to normal muscle function, contributing to the maintenance normal muscle function, contributing to growth in muscle mass, contributing to the maintenance in muscle mass, and contributing to the normal function of the heart.

53. The use according to item 46 for a nutritive product for regulating at least one aspect of endurance and sports physiology, said aspect preferably being selected among improving athletic performance, supporting muscle function during sports performance, supporting muscle function during endurance performance, improving endurance during sports performance, contributing to the maintenance of endurance performance during prolonged endurance exercise, increasing physical performance in successive bursts of short-term, high intensity exercise, improving anaerobic threshold in athletes, improving VO2max in athletes, improving mitochondrial spare respiratory capacity, supporting normal function of the mitochondria, empowering the mitochondria, improving mitochondrial biogenesis, counteracting tiredness and fatigue, contributing to reduction of tiredness and fatigue, and contributing to normal energy-yielding metabolism.

54. The use according to item 46 for a nutritive product for regulating at least one aspect of joint physiology, said aspect preferably being selected among supporting cartilage and joint function and supporting the flexibility of joints.

55. The use according to item 46 for a nutritive product for regulating at least one aspect of cognitive and mental function, said aspect preferably being selected among improving absentmindedness, supporting mental function, supporting a healthy mental function, counteracting forgetfulness, improving memory function, contributing to normal psychological function, contributing to maintenance of normal brain function, contributing to normal cognitive function, contributing to normal functioning of the nervous system, and contributing to normal neurotransmission.

56. The use according to item 46 for a nutritive product for regulating at least one aspect of blood lipid physiology, said aspect preferably being selected among contributing to the maintenance of normal blood cholesterol levels, contributing to the maintenance of normal blood triglyceride levels, lowering or reducing blood cholesterol, and lowering or reducing blood triglyceride levels.

57. The use according to item 46 for a nutritive product for regulating at least one aspect of blood glucose physiology, such as contributing to the maintenance of normal blood glucose levels.

58. The use according to item 46 for a nutritive product for improving the healing of a wound.

59. A composition comprising:
i) an alkaloid or alkaloid fraction according to any one of items 1-9; and
ii) a suitable vehicle.

60. The composition according to item 59, wherein the composition is a pharmaceutical, a medical device or a nutritive product.

61. A composition comprising an alkaloid or alkaloid fraction according to any one of items 1-9 for use as a medicament.

62. The composition according to any of the items 59-61 for the treatment or prevention of a dermatological disease, a cardiovascular disease, a dyslipidemic disorder, a pre-diabetic disorder, type 2 diabetes, metabolic syndrome, obesity, frailty, sarcopenia, osteoarthritis, an inflammatory disease, and diseases associated with mitochondrial dysfunction.

63. The composition according to any of the items 59-61 for the treatment or prevention of a wound.

64. The composition according to any of the items 59-63, wherein the total mass fraction of Ribetril A of said composition is selected among 0.0001%-100%, 0.00025%-90%, 0.0005%-80%, 0.00025%-70%, 0.0005%-60%, 0.00075%-50%, 0.001%-45%, 0.0025%-40%, 0.005%-35%, 0.0075%-30%, 0.01%-25%, 0.025%-20, 0.05%-19%, 0.075%-18%, 0.1%-17%, 0.25%-16%, 0.5%-15%, 0.75%-14%, 1%-13%, 1.5%-12%, 2.0%-11%, 3.0%-10%, 4.0%-9.0%, 5.0%-8.0% and 6.0%-7.0%.

65. The composition according to any of the items 59-63, wherein the total mass fraction of Ribetril A, Ribetril B, Ribetril C, Ribetril D and/or Ribetril E of said composition is selected among 0.0002%-100%, 0.0005%-90%, 0.0008%-80%, 0.001%-70%, 0.0025%-60%, 0.005%-50%, 0.0075%-45%, 0.01%-40%, 0.025%-35%, 0.05%-30%, 0.075%-25%, 0.1%-20, 0.25%-19%, 0.5%-18%, 0.75%-17%, 1.0%-16%, 1.5%-15%, 2.0%-14%, 2.5%-13%, 3.0%-12%, 4.0%-11%, 5.0%-10%, 6.0%-9.0% and 7.0%-8.0%.

66. The composition according to any of the items 59-63, wherein the total mass fraction of Glucoindol A and/or Glucoindol B of said composition is selected among 0.0008%-100%, 0.001%-90%, 0.0025%-80%, 0.005%-70%, 0.0075%-60%, 0.01%-50%, 0.025%-45%, 0.05%-40%, 0.075%-35%, 0.1%-30%, 0.25%-25%, 0.5%-20, 0.75%-19%, 1.0%-18%, 1.5%-17%, 2.0%-16%, 2.5%-15%, 3.0%-14%, 3.5%-13%, 4.0%-12%, 4.5%-11%, 5.0%-10%, 6.0%-9.0% and 7.0%-8.0%.

67. The composition according to any of the items 59-64, allowing provision of a single dosage of an alkaloid or alkaloid fraction according to any of items 1-9 selected among 0.01-5000 mg, 0.05-4000 mg, 0.1-3000 mg, 0.25-2000, 0.5-1750 mg, 0.75-1500 mg, 1-1250 mg, 1.5-1000 mg, 2-900 mg, 2.5-800 mg, 3-700 mg, 4-600 mg, 5-500 mg, 7.5-400 mg, 10-350 mg, 15-300 mg, 20-250 mg, 30-200 mg, 40-150 mg, 50-125 mg and 75-100 mg.

68. The composition according to any one of items 59-67, wherein the alkaloid fraction is synthetic or produced by recombinant technology.

69. The composition according to any of the items 59-68, wherein the alkaloid fraction is derived from a natural source.

70. A method of treating a subject by administering an alkaloid fraction, extract, juice or concentrate of *Ribes*, nutritive product or a composition according to any of the preceeding items to said subject.

71. The method according to item 70 for the treatment or prevention of a dermatological disease, a cardiovascular disease, a dyslipidemic disorder, a pre-diabetic disorder, type 2 diabetes, metabolic syndrome, obesity, frailty, sarcopenia, osteoarthritis, an inflammatory disease and diseases associated with mitochondrial dysfunction.

72. The method according to item 70 for the treatment or prevention of a wound.

73. The method according to item 70 for supporting, normalizing or improving muscle function, athletic performance, mitochondrial function, neurological function, mental function, skin function, metabolic function, cardiovascular function, joint function or for decreasing at least one physiological sign of aging.

74. The method according to item 70 for supporting general well being.

75. The method according to item 70 for supporting or improving at least one aspect of mitochondrial physiology, said aspect selected from the group consisting of mitochondrial function, mitochondrial biogenesis and mitochondrial spare respiratory capacity.

76. The method according to item 70 for regulating at least one aspect of skin physiology, said aspect preferably being selected among supporting skin integrity, normalizing or improving skin function and structure, contributing to the maintenance of normal skin, contributing to the maintenance of normal formation of connective tissue and contributing to the maintenance of normal mucous membranes.

77. The method according to item 70 for regulating at least one aspect of aging physiology, said aspect preferably being selected among supporting healthy aging, decrease age-related loss of muscle mass, decrease age-related loss of muscle strength, decrease age-related loss of heart muscle function, decrease age-related deterioration of skin structure, decrease age-related loss of skin regeneration, decrease age-related deterioration of bone formation, decrease age-related loss of endocrine function, decrease age-related loss of neuronal function, decrease age-related deterioration of mitochondrial function, decrease age-related deterioration of mitochondrial biogenesis, decrease age-related deterioration of mitochondrial spare respiratory capacity, decrease age-related loss of vision function, decrease age-related loss of memory function, decrease age-related loss of mental function, decrease age-related loss of physical endurance, decrease age-related decline in muscle function, supporting muscle function in the elderly and improving muscle endurance in the elderly.

78. The method according to item 70 for regulating at least one aspect of muscle physiology, said aspect preferably being selected among counteracting sedentary decline in muscle function, improving muscle function decreased by inactivity, supporting muscle function decreased by inactivity, contributing to normal muscle function, contributing to the maintenance normal muscle function, contributing to growth in muscle mass, contributing to the maintenance in muscle mass, and contributing to the normal function of the heart.

79. The method according to item 70 for regulating at least one aspect of endurance and sports physiology, said aspect preferably being selected among improving athletic performance, supporting muscle function during sports performance, supporting muscle function during endurance performance, improving endurance during sports performance, contributing to the maintenance of endurance performance during prolonged endurance exercise, increasing physical performance in successive bursts of short-term, high intensity exercise, improving anaerobic threshold in athletes, improving VO2max in athletes, improving mitochondrial spare respiratory capacity, supporting normal function of the mitochondria, empowering the mitochondria, improving mitochondrial biogenesis, counteracting tiredness and fatigue, contributing to reduction of tiredness and fatigue, and contributing to normal energy-yielding metabolism.

80. The method according to item 70 for regulating at least one aspect of joint physiology, said aspect preferably being selected among supporting cartilage and joint function and supporting the flexibility of joints.

81. The method according to item 70 for regulating at least one aspect of cognitive and mental function, said aspect preferably being selected among improving absentmindedness, supporting mental function, supporting a healthy mental function, counteracting forgetfulness, improving memory function, contributing to normal psychological function, contributing to maintenance of normal brain function, contributing to normal cognitive function, contributing to normal functioning of the nervous system and contributing to normal neurotransmission.

82. The method according to item 70 for regulating at least one aspect of blood lipid physiology, said aspect preferably being selected among contributing to the maintenance of normal blood cholesterol levels, contributing to the maintenance of normal blood triglyceride levels, lowering or reducing blood cholesterol, and lowering or reducing blood triglyceride levels.

83. The method according to item 70 for regulating at least one aspect of blood glucose physiology, such as contributing to the maintenance of normal blood glucose levels.

84. A method for manufacturing an extract, juice or concentrate of *Ribes* comprising an alkaloid fraction according to any of the items 1-9, comprising the steps:

i) preparing a juice or suspension of the ground berries and/or leaves;

ii) optionally extracting the juice or ground berries and/or leaves with an extraction agent;

iii) optionally removing said extraction agent and/or excessive water;

iiii) concentrating the alkaloid in order to obtain an alkaloid fraction.

85. The method according to item 84, wherein the *Ribes* is selected among *Ribes rubrum* and/or *Ribes nigrum*.

86. The method according to item 84 or 85, wherein the juice or the suspension of the ground berries and/or leaves are subjected to at least one enzyme, preferably selected among cellulases, amylases and pectinases.

87. The method according to any of the items 84-86, comprising the step of extracting the ground berries and/or leaves with an extraction agent, said extraction agent comprises water, an organic solvent or a mixture thereof.

88. The method according to any of the items 84-87, wherein the step of concentrating the alkaloid fraction comprises centrifugation, ultrafiltration, nanofiltration, chromatography, solid-liquid extraction, liquid-liquid extraction and/or drying.

The invention claimed is:

1. A method to aid in the treatment of a disease or condition selected from the group consisting of a dermatological disease, a cardiovascular disease, a dyslipidemic disorder, a pre-diabetic disorder, a wound, type 2 diabetes, metabolic syndrome, obesity, frailty, sarcopenia, osteoarthritis, an inflammatory disease, and diseases associated with mitochondrial dysfunction, the method comprising the step of administering to a subject having said disease or condition a composition comprising a juice or concentrate obtainable from *Ribes rubrum* and a juice or concentrate obtainable from *Ribes nigrum*.

2. The method according to claim 1, wherein said juice or concentrate comprises an alkaloid compound of formula (I), (II), or (III), or a combination thereof:

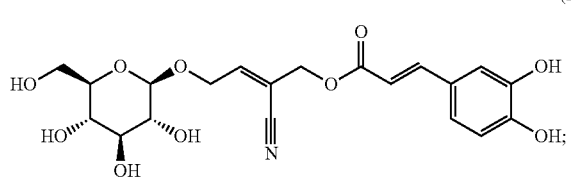

(I)

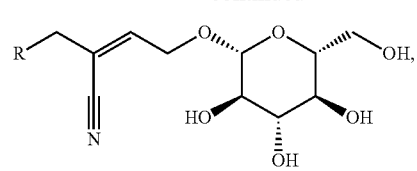

(II)

wherein R is an acyloxy moiety derived from an acid selected from the group consisting of 4-hydroxy-3-methoxybenzoic acid, 4-hydroxybenzoic acid, (E)-3-(4-hydroxy-3-methoxyphenyl)acrylic acid and (E)-3-(4-hydroxyphenyl)acrylic acid; and

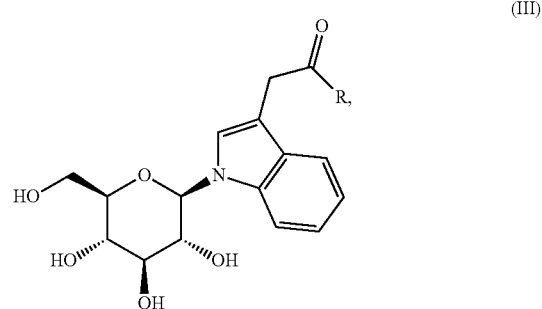

(III)

3. The method according to claim 2, wherein the alkaloid compound is selected from the group consisting of (E)-(E)-2-cyano-4-(((2R,3R,4S,5S,6R)-3,4,5-trihydroxy-6-(hydroxymethyl)tetrahydro-2H-pyran-2-yl)oxy)but-2-en-1-yl 3-(3,4-dihydroxyphenyl)acrylate (Ribetril A), (E)-(E)-2-cyano-4-(13-D-glucopyranosyloxy)but-2-en-1-yl 3-(4-hydroxy-3-methoxyphenyl)acrylate (Ribetril B), (E)-(E)-2-cyano-4-(13-D-glucopyranosyloxy)but-2-en-1-yl 3-(4-hydroxyphenyl)acrylate (Ribetril C), (E)-2-cyano-4-(13-D-glucopyranosyloxy)but-2-en-1-yl 4-hydroxy-3-methoxybenzoate (Ribetril D), (E)-2-cyano-4-(13-D-glucopyranosyloxy)but-2-en-1-yl 4-hydroxybenzoate (Ribetril E), 1-13-D-glucopyranosyl-1H-indole-3-acetic acid (Glucoindol A), and 1-13-D-glucopyranosyl-1H-indole-3-acetic acid methyl ester (Glucoindol B).

4. The method according to claim 1, wherein said juice or concentrate has been subjected to treatment with at least one enzyme selected from the group consisting of cellulases, amylases, and pectinases.

5. The method according to claim 1, wherein said juice or concentrate has been obtained by a process comprising concentrating a composition obtained from said *Ribes* species by centrifugation, ultrafiltration, nanofiltration, chromatography, solid-liquid extraction, liquid-liquid extraction, and/or drying.

6. The method according to claim 1, wherein said composition is a medicament or a nutritive product.

7. The method according to claim 1, that aids in wound repair.

8. The method according to claim 1, that aids in supporting, normalizing or improving a condition selected from the group consisting of muscle function, athletic performance, mitochondrial function, neurological function, mental function, skin function, cardiovascular function, metabolic function, joint function, and physiological parameters associated with aging.

9. The method according to claim 1 that supports general well-being.

10. The method according to claim 1, whereby at least one aspect of skin physiology is regulated, said aspect selected from the group consisting of skin integrity, skin regeneration, skin function and structure, formation of connective tissue, and maintenance of mucous membranes.

11. The method according to claim 1, whereby at least one aspect of aging physiology is regulated, said aspect selected from the group consisting of age-related loss of muscle mass, age-related loss of muscle strength, age-related loss of heart muscle function, age-related deterioration of skin structure, age-related loss of skin regeneration, age-related deterioration of bone formation, age-related loss of endocrine function, age-related loss of neuronal function, age-related deterioration of mitochondrial function, age-related deterioration of mitochondrial biogenesis, age-related deterioration of mitochondrial spare respiratory capacity, age-related loss of vision function, age-related loss of memory function, age-related loss of mental function and age-related loss of physical endurance.

12. The method according to claim 1, whereby at least one aspect of muscle physiology is regulated, said aspect selected from the group consisting of sedentary decline in muscle function, loss of muscle function caused by inactivity, growth in muscle mass, maintenance of muscle mass, and cardiac physiology, mitochondrial function, mitochondrial biogenesis, and mitochondrial spare respiratory capacity.

13. The method according to claim 1, whereby at least one aspect of endurance or sports physiology is regulated, said aspect selected from the group consisting of athletic performance, muscle function during sports performance, muscle function during endurance performance, endurance during sports performance, endurance performance during prolonged endurance exercise, physical performance during successive bursts of short-term high intensity exercise, anaerobic threshold in athletes, $VO_2$max in athletes, mitochondrial spare respiratory capacity, function of the mitochondria, mitochondrial biogenesis, tiredness, fatigue, and energy-yielding metabolism.

14. The method according to claim 1, whereby at least one aspect of joint physiology is regulated, said aspect selected from the group consisting of joint function, joint flexibility, and maintenance of cartilage.

15. The method according to claim 1, whereby at least one aspect of cognitive and mental function is regulated, said aspect selected from the group consisting of memory function, cognitive function, neurotransmission, neuronal mitochondrial function, neuronal mitochondrial biogenesis, and neuronal mitochondrial spare respiratory capacity.

16. The method according to claim 1, whereby at least one aspect of mitochondrial physiology is regulated, said aspect selected from the group consisting of mitochondrial function, mitochondrial biogenesis, and mitochondrial spare respiratory capacity.

17. The method according to claim 1, whereby at least one aspect of metabolic syndrome physiology is regulated, said aspect selected from the group consisting of blood cholesterol levels, blood triglyceride levels, and blood glucose levels.

* * * * *